US007579004B2

(12) United States Patent
Poland et al.

(10) Patent No.: US 7,579,004 B2
(45) Date of Patent: Aug. 25, 2009

(54) NATURALLY PROCESSED MEASLES VIRUS PEPTIDES ELUTED FROM CLASS II HLA MOLECULES

(75) Inventors: Gregory A. Poland, Rochester, MN (US); Inna G. Ovsyannikova, Rochester, MN (US); David C. Muddiman, Raleigh, NC (US); Kenneth L. Johnson, Rochester, MN (US)

(73) Assignee: Mayo Foundation for Medical Education, Rochester, MN (US)

( * ) Notice: Subject to any disclaimer, the term of this patent is extended or adjusted under 35 U.S.C. 154(b) by 276 days.

(21) Appl. No.: 11/266,957

(22) Filed: Nov. 4, 2005

(65) Prior Publication Data

US 2006/0127410 A1 Jun. 15, 2006

Related U.S. Application Data

(63) Continuation-in-part of application No. 11/116,682, filed on Apr. 28, 2005, now abandoned.

(60) Provisional application No. 60/566,899, filed on Apr. 30, 2004.

(51) Int. Cl.
*A61K 39/38* (2006.01)
*A61K 38/00* (2006.01)
*G01N 33/53* (2006.01)

(52) U.S. Cl. .............. 424/184.1; 424/186.1; 424/211.1; 424/185.1; 530/324; 435/7.1

(58) Field of Classification Search ........................ None
See application file for complete search history.

(56) References Cited

OTHER PUBLICATIONS

Davidkin, Irja and Valle, Martti. "Vaccine-induced measles virus antibodies after two doses of combined measles, mumps and rubella vaccine: a 12-year follow-up in two cohorts". Vaccine. 1998, 16: 2052-2057.*
Ovysyannikova IG et al "Variation in vaccine response in normal populations". Pharmacogenomics. Jun. 2004;5(4):417-27.*
Caillat-Zueman et al. "Distinct HLA class II alleles determine antibody response to vaccination with hepatitis B surface antigen". Kidney Int. Jun. 1998;53(6):1626-30.*
Schenke et al. "Binding specificity of a class II-restricted hepatitis B epitope by DR molecules from responder and nonresponder vaccine recipients."0 Human Immunology. 1998, 59(12):783-93.*
Obeid et al "dentification of helper T cell antigenic sites in mice from the haemagglutinin glycoprotein of measles virus" J. Gen Virology, 74:2549-2557, 1993.*
Black S, et al., "Efficacy, Safety and Immunogenicity of Heptavalent Pneumococcal Conjugate Vaccine in Children. Northern California Kaiser Permanente Vaccine Study Center Group," Pediatr. Infect. Dis. J. 19:187-195 (2000).
Booy R, et al., "Vaccine Failures After Primary Immunisation with Haemophilus influenza Type-B Conjugate Vaccine without Booster," Lancet 349:1197-1202 (1997).
Gerlich W & Bruss V, "Functions of Hepatitis B Virus Proteins and Molecular Targets for Protective Immunity" in Hepatitis B Vaccines in Clinical Practice, 41-82 (Ellis R, ed. 1993).
Jonsdottir I, et al., "Functional Activity of Antibodies Elicited by Octavalent Pneumococcal Polysaccharide Conjugate Vaccines, PncT and PncD," [Abstract G-90]. In: 37th Interscience Conference on Antimicrobial Agents and Chemotherapy, Toronto, Canada, Sep. 28 to Oct. 1, 1997.
Jonsdottir I, et al., "Pneumococcal Conjugate Vaccine Induces Protective Immunity in Toddlers," [Abstract 43]. Presented at the 40th Interscience Conference on Antimicrobial Agents and Chemotherapy, Toronto, Canada, Sep. 17-20, 2000.
Konishi E & Fujii A, "Dengue Type 2 Virus Subviral Extracellular Particles Produced by a Stably Transfected Mammalian Cell Line and Their Evaluation for a Subunit Vaccine," Vaccine 20:1058-1067 (2002).
Lottenbach K, et al., "Safety and Immunogenicity of Haemophilus influenzae type B Polysaccharide or Conjugate Vaccines in an Elderly Adult Population," J. Am. Geriatr. Soc. 52:1883-1887 (2004).
Milch D, "Application of Synthetic Peptide Technology to Experimental HBV Vaccine Design" in Hepatitis B Vaccines in Clinical Practice, 351-381 (Ellis R, ed. 1993).
Nemchinov L, et al., "Development of a Plant-derived Subunit Vaccine Candidate Against Hepatitis C Virus," Arch. Virol. 145:2557-2573 (2000).
Potter A & Babiuk L, "New Approaches for Antigen Discovery, Production and Delivery: Vaccines for Veterinary and Human Use," Curr. Drug Targets Infect. Dis. 1:249-262 (2001).
Plotkin S, "Immunologic correlates of protection induced by vaccination," Pediatr. Infect. Dis. J. 20:63-75 (2001).
Sala F, et al., "Vaccine Antigen Production in Transgenic Plants: Strategies, Gene Constructs and Perspectives," Vaccine 21:803-808 (2003).
Ovsyannikova I, et al., "Naturally processed measles virus peptide eluted from class II HLA-DRB1 *03 recognized by T lymphocytes from human blood," Virology 312:495-506 (2003).
Ovsyannikova I, et al., "Identification and characterization of novel, naturally processed measles virus class II HLA-DRB1 peptides," J Virol. 78:42-51 (2004).
Poland G, et al., "Identification of an association between HLA class II alleles and low antibody levels after measles immunization," Vaccine 20:430-438 (2001).

* cited by examiner

*Primary Examiner*—Bo Peng
(74) *Attorney, Agent, or Firm*—Quarles & Brady LLP

(57) ABSTRACT

A preparation of peptides eluted from class II HLA molecules is disclosed. Methods of decreasing measles infections comprising inoculating human patients with a vaccine comprising one or more of the peptides and methods of diagnosing measles infections or immunity comprising analyzing human patients for the presence of one or more of the peptides or antibodies to the peptide(s) are also disclosed.

8 Claims, 12 Drawing Sheets

NATURALLY PROCESSED MEASLES VIRUS PEPTIDES ELUTED FROM CLASS II HLA MOLECULES

CROSS-REFERENCE TO RELATED APPLICATION

This application is a continuation-in-part of U.S. patent application Ser. No. 11/116,682, filed Apr. 28, 2005 now abandoned, and thereby claims priority to U.S. Patent Application Ser. No. 60/566,899, filed Apr. 30, 2004. Each of these applications is incorporated by reference as if fully set forth herein.

STATEMENT REGARDING FEDERALLY SPONSORED RESEARCH OR DEVELOPMENT

This invention was made with United States government support awarded by NIH AI33144. The United States government has certain rights in this invention.

BACKGROUND OF THE INVENTION

The World Health Organization has targeted measles for worldwide eradication, requiring an immunogenic vaccine for the genetically heterogeneous outbred population. Although well controlled by vaccination programs in industrialized countries, measles virus (MV) infection continues to be one of the major causes of childhood morbidity and mortality in developing countries The requirement for a cold chain (storage), the induction of low seroconversion rates in the presence of maternal antibodies, the vaccine failure rate, and the inability to use the vaccine in immuno-compromised persons are the major drawbacks of the live attenuated measles vaccine (El Kasmi, et al., *J. Gen. Virol.* 81:729-735, 2000; Albrecht, et al., *J. Pediatr.* 91:715-718, 1977). The limitations of the live vaccine combined with inadequate coverage in developing countries leads to approximately one million measles-related deaths annually (Jaye, et al, *J. Clin. Invest.* 102: 1969-1977, 1998; Sabin, *Eur. J. Epidemiol.* 7:1-22, 1991). Thus, there is a need to develop alternative vaccines that are thermostable, safe and designed to avoid recognition and neutralization by passive maternal antibodies (El Kasmi, et al., *Vaccine* 17:2436-2445, 1999; Jaye, et al., supra, 1998). Such vaccines should induce long lasting cell-mediated and humoral immune responses. For this reason, the development of a candidate peptide-based vaccine, based on immunologically relevant information on naturally processed and presented measles virus-derived peptides eluted from HLA class I and class II antigen-presenting molecules, would have a significant impact.

Defining peptide epitopes recognized by CD8+ and CD4+ T lymphocytes involved in immune responses has generated tremendous interest (Germain, *Cell* 76:287-299, 1994a). We previously demonstrated that humoral immune responses to measles-encoded proteins are strongly associated with the human leukocyte antigen (HLA) class I and class II genes (Poland, et al., *Vaccine* 17:1719-1725, 1999). In particular, HLA-DRB1*03 (DR3) alleles are significantly associated with measles vaccine seronegativity and play an important role in the immune response to MV (Poland, et al., *Vaccine* 20:430-438, 2001a). Identification and comparison of the repertoire of measles-derived peptides that bind to class II HLA-DR3 molecules in poor- and high-responders to measles vaccine is important for design of more effective vaccines against measles. The HLA class I and class II antigen-processing pathways play a critical role in the activation of measles-specific T-lymphocytes by presenting peptide epitopes derived from viral proteins (Pamer, *Clin. Infect. Dis.* 28:714-716, 1999). The HLA class II molecules bind and present exogenous measles antigens for recognition by CD4+ T-helper cells and play an important role in the immune response to measles (Germain, *Int. J. Technol. Assess. Health Care* 10:81-92, 1994b; Germain, *Ann. NY Acad. Sci.* 754: 114-125, 1995; Pamer, supra, 1999). Alternatively, class II molecules can also use the endogenous pathway of measles virus antigen presentation (Nuchtern, et al., *Nature* 343:74-76, 1990; Sekaly, et al., *Proc. Natl. Acad. Sci. USA* 85:1209-1212, 1988). Identification of such immunogenic measles epitopes, which are recognized by T- and B-lymphocytes would advance peptide-base therapies and vaccine development (Poland, et al., *Vaccine* 19:2692-2700, 2001b). However, a potential obstacle to the development of a peptide-based measles vaccine is the high degree of human HLA gene polymorphism (Doolan, et al, *J. Immunol.* 1123-1137, 2000).

HLA molecules bind antigenic peptides and display them to T cell receptors on the surface of helper T cells (Garcia, et al., *Annu. Rev. Immunol.* 17:369-397, 1999; Brown, et al., *Nature* 332:845-850, 1988; Stern, et al., *Nature* 368:215-221, 1994). Adoptive immune responses are therefore limited by the spectrum of immunogenic peptides displayed to T cells. Limitations in identifying class II peptides include the difficulty in detecting pathogen-derived peptides eluted from HLA class II-peptide complexes and the lack of knowledge regarding HLA class II presentation of measles virus peptides, as only a few human measles virus class I peptides and HLA class II-restricted cytotoxic T lymphocytes (CTL) responses are described in the literature (Herberts, et al., *J. Gen. Virol.* 82:2131-2142, 2001; van Els, et al., *Eur. J. Immunol.* 30:1172-1181, 2000; van Binnendijk, et al., *J. Virol.* 67:2276-2284, 1993; Jacobson, et al., *J. Virol.* 63:1756-1762, 1989). However, the rapid characterization of defined peptides that are critical to viral immunity, including measles, has been significantly enhanced by mass spectrometry (MS), which provides peptide sequence information at the femtomole level of sensitivity.

Although direct sequencing of naturally processed peptides bound to HLA Class I and II molecules by liquid chromatography mass spectrometry (LC-MS) is established (Dongre, et al., *Eur. J. Immunol.* 31:1485-1494, 2001; de Jong, *Mass Spectrom. Rev.* 17:311-335, 1998), identification of pathogen-derived peptides presents a formidable challenge due to the diverse range of low abundance peptides presented by HLA molecules. Strategies to reduce the complexity of the mixture prior to introduction into the mass spectrometer have often relied on multiple steps of reversed phase (RP) liquid chromatography. However, this approach does not effectively increase the peak capacity because the separation mechanisms of each RP chromatography step are not orthogonal.

Needed in the art of measles diagnosis and vaccine development are diagnostic and therapeutic methods that depend on the isolation of naturally processed measles virus peptides eluted from class II HLA molecules.

BRIEF SUMMARY OF THE INVENTION

In one embodiment, the present invention is a preparation of an HLA class II binding peptide selected from the group consisting of SEQ ID NOs:1-13 and functional variants thereof. Preferably, the peptide is SEQ ID NO:1 or functional variant thereof or SEQ ID NO:2 or functional variant thereof.

In another embodiment, the present invention is a nucleic acid molecule encoding the peptides described above.

In another embodiment, the present invention is a method of decreasing measles infection comprising inoculating a human patient with a vaccine comprising or encoding a peptide selected from the group consisting of SEQ ID NOs:1-13 or functional variants thereof.

Preferably, the method comprises inoculating a human patient with a vaccine comprising or encoding at least two peptides selected from the group consisting of SEQ ID NOs: 1-13 or functional variants thereof.

In another embodiment, the present invention is a method of diagnosing measles infection or immunity comprising analyzing a human patient for the presence of a peptide selected from the group of SEQ ID NOs:1-13 or antibodies to peptides SEQ ID NOs:1-13.

Other features, advantages or methods of the present invention will become apparent to one of skill in the art after examination of the specification, claims and drawings.

BRIEF DESCRIPTION OF THE SEVERAL VIEWS OF THE DRAWINGS

FIG. 2A illustrates a naturally processed peptide (inset shows an expansion of the m/z range 720 to 920). FIG. 2B shows a synthetic peptide having SEQ ID NO:2 (inset shows an expansion of the m/z range 720 to 920).

FIG. 3A illustrates a naturally processed peptide with targeted data dependant analysis and increased loading as compared to the data shown in FIG. 2A (inset shows the selected ion current for m/z=689.67±0.5 over a 15 minute RP retention time window.) FIG. 3B shows a naturally processed peptide spiked with 500 femtomoles of the synthetic peptide (inset shows the selected ion current for m/z=689.67±0.5 over a 15 minute RP retention time window). The peak tailing in FIG. 3B clearly indicates we have overloaded the column in the standard additions experiment; however, the retention times in FIGS. 3A and 3B are still within 5% of each other.

DETAILED DESCRIPTION OF THE INVENTION

In General

We have adopted an approach, developed in the field of proteomics, to resolve the profound biological complexity presented in investigations of peptides bound to HLA class II molecules. The approach is based on two truly orthogonal separation techniques, namely, (1) strong cation exchange (SCX) chromatography, which separates peptides based on their charge, and (2) nano-scale reversed phase liquid chromatography which uses hydrophobicity (Link, et al., *Nat. Biotechnol.* 17:676-682, 1999; Washburn, et al., *Nat. Biotechnol.* 19:242-247, 2001). This fully automated, multi-dimensional chromatography-MS approach affords a geometric increase in the overall peak capacity that dramatically increases the effective dynamic range and the number of peptides which can be dissociated (sequenced using data-dependent tandem-MS) for any given sample.

Figure 1:
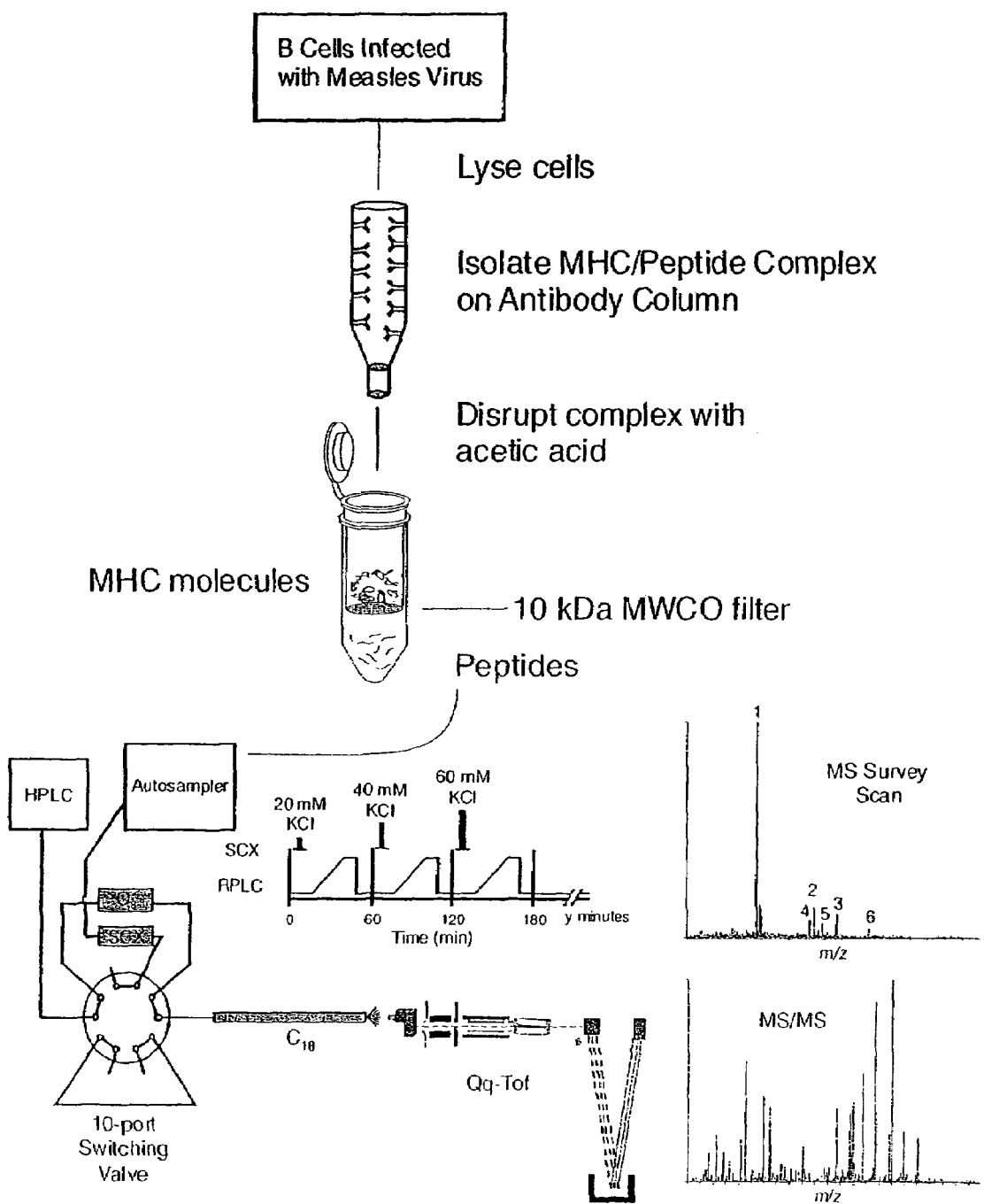
FIG. 1 is an overview of the analytical method for isolating and sequencing MHC Class II peptides. B cells infected with measles virus are lysed and MHC molecule/peptide complexes are isolated on an antibody column. Dissociated peptides were loaded onto an automated 2D-LC-MS system. Peptides were eluted from the SCX column by salt steps introduced by the autosampler. Data dependent MS/MS experiments were conducted during the subsequent reversed phase nano-LC separations.

An overview of the methodology we developed for identifying MHC Class II peptides originating from measles virus is shown in FIG. 1. This methodology provides a powerful tool for the identification of pathogen-derived HLA class II peptides that in turn can be evaluated as potential subunit vaccine candidates. We describe naturally processed measles phosphoprotein (P)-derived peptide and nucleoprotein (N)- derived peptide which were isolated and sequenced from class II HLA-DR3 molecules of measles virus infected EBV-transformed B (EBV-B) cell lines by mass spectrometry in Examples 1-3. We also describe 11 additional class II HLA-DR3 peptides in Example 4.

Isolated Peptides

In one embodiment, the present invention is a preparation comprising one of the peptides described below and in Table 10, SEQ ID NOs:1-13. These peptides are defined by their amino acid composition as follows:

```
From measles phosphoprotein:
ASDVETAEGGEIHELLRLQ         (SEQ ID NO:2)
ASDVETAEGGEIHELLR           (SEQ ID NO:3)
ASDVETAEGGEIHELLRLQSR       (SEQ ID NO:4)
GFRASDVETAEGGEIHELLRLQ      (SEQ ID NO:5)

TLNVPPPPDPGR                (SEQ ID NO:6)
TLNVPPPPDPGRASTSGTPIKK      (SEQ ID NO:7)

KMSSAVGFVPDTGPASR           (SEQ ID NO:8)

From measles nucleoprotein:
SAGKVSSTLASELG              (SEQ ID NO:1)
SAGKVSSTLASELGITAEDARLVS    (SEQ ID NO:9)

AVGPRQAQVSF                 (SEQ ID NO:10)

LLEVVQSDQSQSGLTFASR         (SEQ ID NO:11)

HLPTGTPLDIDTATESSQDPQDSR    (SEQ ID NO:12)

From measles hemagglutinin:
SLSTNLDVTNSIEHQVKDVLTPLFK   (SEQ ID NO:13)
```

By "preparation" we mean any concentration of the peptide that is enhanced or purified relative to its natural occurrence. Preferably, the preparation is substantially pure or is combined with other ingredients into a pharmaceutical preparation. A preparation of the present invention will likely include adjuvants or carriers that might be coupled to the peptide sequence.

Each of these peptides was directly eluted out of class II human HLA molecules after natural processing and presentation. The implication of this is that these peptides are exactly what is presented to, and seen by, the human immune system. To our knowledge, this has never before been reported for class II-bound measles peptides or proteins. The immune system then initiates a variety of immune responses to these peptides. In turn, this suggests several useful applications for these peptides.

The present invention also includes functional variants of the peptides disclosed in SEQ ID NOs:1-13. One of skill in the art of molecular biology would understand that the N-1 peptide and the P-1 peptide (SEQ ID NOs:1 and 2) and peptides SEQ ID NOs:3-13 could be modified in trivial or conservative ways and yet still retain their biological activity. For example, while we have demonstrated that N-I and P-1 peptides are indeed immunogenic and initiate long-term memory or "recall" immune responses in human cells previously exposed to measles virus, it is also extremely likely that variations of these peptide sequences are also immunogenic. These measles-derived peptides are bound in HLA allele peptide binding grooves (indeed, we directly eluted these peptides out of the peptide binding grooves). Once in these grooves, the peptide is presented to T cells, which then triggers a cascade of events—ultimately leading to a spectrum of immune responses to the peptide.

It is well known that certain and specific amino acids within the peptide sequence are crucial to proper binding (for both electrical charge and space-filling reasons) within the HLA molecule's peptide binding groove. In turn, such peptide binding conforms to "pockets" or "anchors" within the peptide binding grooves that bind these crucial amino acids which in part compose the peptide(s) of interest. In the case of the class II HLA molecules we are discussing herein, the binding groove is approximately 9 amino acids long. It has been demonstrated that an unusual feature of the class II binding groove is that only 2-3 of the 4-5 possible anchors have to be occupied by the usually proscribed amino acid. In turn, this implies that as long as the crucial amino acids are in place, the remaining amino acids may be more promiscuous—allowing different amino acid combinations to be present or absent.

The importance of the preceding discussion is that it is quite likely that "trimming" these identified peptides by 1-3 or more amino acids on either end of the peptide would not adversely impact the ability of these peptides to be bound within the peptide binding groove and the significance or immunogenicity of these peptides. In fact, peptides as small as 8 amino acids are known to contain functional epitopes.

Conversely, amino acids could be added without ill effect as both ends of the class II peptide binding groove are open, and peptides as long or longer than 24 amino acids have been identified. Nonetheless, the amino acid binding cleft contains only a 9 amino acid length, usually with 2-8 amino acid residues on both ends (so called "ragged ends") to enhance affinity.

Therefore, as noted above, the invention embraces functional variants of the class II binding peptides SEQ ID NOs:1-13. As used herein, a "functional variant" or "variant" of a HLA class II binding peptide is a peptide which contains one or more modifications to the primary amino acid sequence of the HLA class II binding peptide and yet retains the HLA class II and T cell receptor binding properties disclosed herein. One would preferably use the procedures disclosed below in Examples 1-4 to determine whether a peptide retains HLA class II and T cell receptor binding properties. Preferably, the peptide of SEQ ID NOs:1-13 would be modified at 1, 2, 3, 4 or 5 amino acid residues.

For example, in the process of verifying these sequence from the Genbank database, we found that SEQ ID NO:12 from measles nucleoprotein also exists as an additional form (or variant) of the nucleoprotein where the " . . . ATES . . . " portion of SEQ ID NO:12 is " . . . ASES . . . " (substitution of an S for a T). Both sequences exist in the database. In our work, we have identified the form containing " . . . ATES . . . . " The " . . . ASES . . . " form of SEQ ID NO:12 is a suitable functional variant of the present invention.

Modifications which create an HLA class II binding peptide functional variant can be made (1) to enhance a property of a HLA class II binding peptide, such as peptide stability in an expression system or the stability of protein-protein binding such as HLA-peptide binding; (2) to provide a novel activity or property to a HLA class II binding peptide, such as addition of an antigenic epitope or addition of a detectable moiety; or (3) to provide a different amino acid sequence that produces the same or similar T cell stimulatory properties. Modifications to the HLA class II binding peptides of SEQ ID NOs:1-13 can be made to nucleic acids which encode the peptide and can include deletions, point mutations, truncations, amino acid substitutions and additions of amino acids. Alternatively, modifications can be made directly to the polypeptide, such as by cleavage, addition of a linker molecule, addition of a detectable moiety, such as biotin, addition of a fatty acid, substitution of one amino acid for another and the like. Preferably the substitutions are not made at anchor residues of a HLA binding epitope. Lipids may be attached as possible modifiers, (see Jackson, et al.'s report of a synthetic vaccine of generic structure that targets Toll-like receptor 2 on dendritic cells and promotes antibody or cytotoxic T cell responses. Jackson, et al., *Proc. Natl. Acad. Sci. USA* 101: 15440-15445, 2004).

Variants also can be selected from libraries of peptides, which can be random peptides or peptides based on the sequence of peptides SEQ ID NO:1-13 including substitutions at one or more positions (preferably 1-5). For example, a peptide library can be used in competition assays with complexes of peptides bound to HLA class II molecules (e.g. dendritic cells loaded with the peptides). Peptides which compete for binding of the peptide to the HLA class I molecule can be sequenced and used in other assays (e.g. CD4 lymphocyte proliferation) to determine suitability as a peptide functional variant.

In another embodiment, the present invention is a peptide or use of a peptide comprising SEQ ID NO:1, 3 or 6. These peptides are shorter versions of other peptides disclosed in Examples 1-4 and represent "core" sequences. For example, peptide SEQ ID NO:3 is shorter at either end than SEQ ID NO:2 or SEQ ID NOs:4 or 5. One of skill in the art would understand that SEQ ID NO:3, for example, could have additional residues (preferably 1-5) added at either end and still be functional as a class II HLA molecule.

To obtain the peptides of the present invention, one would most easily chemically synthesize the peptides. Of course, other methods in the art would be appropriate. A variety of methods are available now and in the future to obtain the peptides of interest. The easiest and most obvious is simple chemical synthesis of each peptide. The next would be inserting the genetic code for the amino acids of interest (which then compose the peptide of interest) into a plasmid and inserting it into a vector (or delivery vehicle) which is then delivered to the host and induced to transcribe the genetic code into the peptide of interest—this can be accomplished by naked DNA immunization, or infection by a vector organism. It is also possible to insert the coding sequence for a larger protein into the host organism if it were certain that the protein would then be processed into smaller peptide components that would result in the identified peptides of interest or a functionally equivalent variant.

In another embodiment, the present invention is a nucleic acid sequence which codes for the class II binding peptides or variants thereof and other nucleic acid sequence which hybridize to a nucleic molecule consisting of the above-described nucleotide sequences under high stringency conditions. The term "stringent conditions" as used herein refers to parameters with which the art is familiar. For example, nucleic acid hybridization parameters may be found in references which compile such methods, e.g., *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, high stringency conditions as used herein, refers to hybridization at 65° C. in hybridization buffer (3.5× SSC, 0.02% Ficoll, 0.02% Polyvinyl pyrolidone, 0.02% Bovine Serum Albumin, 25 mM $NaH_2PO_4$ (pH 7), 0.5% SDS, 2 mM EDTA). SSC is 0.15M Sodium Chloride/0.015M Sodium Citrate, pH 7; SDS is Sodium Dodecyl Sulphate; and EDTA is Ethylene diaminetetraacetic acid. After hybridization, the membrane upon which the DNA is transferred is washed at 2×SSC at room temperature and then at 0.1-0.5× SSC/0.1×SDS at temperatures up to 68° C., e.g., 55° C., 60° C., 65° C. or 68° C. Alternatively, high stringency hybridization may be performed using a commercially available hybridization buffer, such as ExpressHyb™ buffer (Clontech) using hybridization and washing conditions described by the manufacturer.

There are other conditions, reagents, and so forth which can be used, which result in a similar degree of stringency familiar to one of skill in the art. It will be understood, however, that the skilled artisan will be able to manipulate the conditions in a manner to permit the clear identification of homologs and alleles of nucleic acids encoding the HLA class II binding peptides of the invention. The skilled artisan also is familiar with the methodology for screening cells and libraries for expression of such molecules which then are routinely isolated, followed by isolation of the pertinent nucleic acid molecule and sequencing.

It will also be understood that the invention embraces the use of the sequences in expression vectors, as well as to transfect host cells and cell lines, be these prokaryotic (e.g. *E. coli*), or eukaryotic (e.g., dendritic cells, CHO cells, COS cells, yeast expression systems and recombinant baculovirus expression in insect cells). The expression vectors require that the pertinent sequence, i.e., those described supra, be operably linked to a promoter.

In another embodiment, the present invention is an antibody, either monoclonal or polyclonal, that specifically binds to a peptide selected from the group consisting of SEQ ID NOs:1-13 or functional variants thereof. One of skill in the art would understand that there are numerous ways to create antibodies specific to the peptides described above.

Peptide-Based Vaccine

The peptides of the present invention, either alone or in combination with other measles peptides, could be used in a peptide-based vaccine to protect against measles. These identified measles-derived peptides, potentially in combination with other yet to be identified peptides, logically could and will be used in the directed design of newer measles vaccines. The major advantage of such an approach includes avoidance of the safety problems and contraindications present for any live viral vaccine (i.e. there are persons who cannot safely receive a live viral vaccine, such as a highly immunocompromised person), and the ease and lower cost of manufacturing such a vaccine.

In one embodiment, the present invention is a peptide vaccine comprising or encoding at least one of the peptides disclosed at SEQ ID NOs:1-13 or functional variants. Applicants specifically envision that one may wish to use the peptides of SEQ ID NOs:1-13 wherein the sequences have been modified by "trimming" or deleting 1-5 amino acids from each end. These amino acids may be replaced with conservative or inert substitutions, may be deleted or may be replaced with amino acid residues designed to supply the vaccine with an additional feature, preferably as described above. The vaccine preferably comprises or encodes at least 2, 3, 4, 5, 6, 7, 8, 9, 10, 11, 12 or all of the peptides.

Multiple options for use of the peptides as a vaccine are possible. A promising technique is the so-called "chain of beads" approach. Here each peptide is chemically linked to the next peptide either with or without an immunologic adjuvant, directly administered as a vaccine. Such an approach has, in essence, been used in the design of the currently licensed pneumococcal and *Haemophilus influenzae* type b vaccines. Another approach, as discussed above, is simply to immunize with the genetic code for the peptides or proteins of interest. Yet another approach would be to encapsulate one or several peptides into viral-like particles (VLP) that again could be directly administered as a vaccine. Other possible and successful delivery methodologies of these peptides may include transcutaneous or mucosal delivery (such as by direct application to the skin via a "patch", nasal spray, eyedrops, or inhaled formulations), with or without an accompanying adjuvant. At the current time there is no one directly preferred vector system or delivery methodology.

A particularly good example for development of peptide-based vaccines will be the approach that was taking for development of *Haemophilus influenza* type b (Hib) capsular polysaccharide conjugate and pneumococcal conjugate vaccines. Usually "the bacterial capsular polysaccharides are poorly immunogenic in young children. The coupling of these polysaccharides with protein carriers renders the polysaccharides visible to the T cells, which then provide help for antibody responses. The big successes of Hib conjugate and pneumococcal conjugate vaccines testify to the power of this strategy. Not only are antibody responses induced in the young children, but the average titers were higher in comparison with those achieved after unconjugated polysaccharide." (Plotkin, *Pediatr. Infect. Dis. J.* 20:63-75, 2001).

One of skill in the art should review the following references (all incorporated by reference) for exemplary models of peptide or peptide-like vaccines.

Milch, "Application of Synthetic Peptide Technology to Experimental HBV Vaccine Desing in Ellis RWed Hepatitis B Vaccines in Clinical Practice," Marcel Dekker Inc., New York, pp. 351-381, 1993.
Gerlich and Bruss, "Functions of Hepatitis B Virus Proteins and Molecular Targets for Protective Immunity in Ellis RWed Hepatitis B Vaccines in Clinical Practice," Marcel Dekker Inc., New York, p. 41-82, 1993.
Manuela, et al., "Vaccine Antigen Production in Transgenic Plants: Strategies, Gene Constructs and Perspectives," Vaccine 21(7-8):803-808, 2003.
Konishi and Fujii, "Dengue Type 2 Virus Subviral Extracellular Particles Produced by a Stably Transfected Mammalian Cell Line and Their Evaluation for a Subunit Vaccine," Vaccine 20(7-8):1058-1067, 2002.
Potter and Babiuk, "New Approaches for Antigen Discovery, Production and Delivery: Vaccines for Veterinary and Human Use," Curr. Drug Targets Infect. Dis. 1(3):249-262, 2001.
Nemchinov, et al., "Development of a Plant-derived Subunit Vaccine Candidate Against Hepatitis C Virus," Arch. Virol. 145(12):2557-2573, 2000.
Plotkin, Pediatr. Infect. Dis. J. 20:63-75, 2001.
Lottenbach, et al., "Safety and Immunogenicity of Haemophilus influenzae type B Polysaccharide or Conjugate Vaccines in an Elderly Adult Population," J. Am. Geriatr. Soc. 52(11):1883-1887, 2004.
Black, et al., "Efficacy, Safety and Immunogenicity of Heptavalent Pneumococcal Conjugate Vaccine in Children. Northern California Kaiser Permanente Vaccine Study Center Group," Pediatr. Infect. Dis. J. 19(3):187-195, 2000.
Jonsdottir, et al., "Functional Activity of Antibodies Elicited by Octavalent Pneumococcal Polysaccharide Conjugate Vaccines, PncT and PncD," [Abstract G-90]. In: $37^{th}$ Interscience Conference on Antimicrobial Agents and Chemotherapy, Toronto, Canada, Sep. 28, to Oct. 1, 1997. Washington, DC: American Society for Microbiology, 1997.
Jonsdottir, et al., "Pneumococcal Conjugate Vaccine Induces Protective Immunity in Toddlers," [Abstract 43]. Persented at the $40^{th}$ Interscience Conference on Antimicrobial Agents and Chemotherapy, Toronto, Canda, Sep. 17-20, 2000.
Booy, et al., "Vaccine Failures After Primary Immunization with Haemophilus influenza Type-B Conjugate Vaccine without Booster," Lancet 349:1197-1202, 1997.

The effectiveness of such a peptide vaccine is easily measured in non-human primate and smaller animal studies. After optimization of the route and dose of peptide vaccine, animals that have and have not been immunized are exposed to sub-lethal and lethal doses of wild measles virus. Efficacy can be defined in multiple ways including lack of evidence of infection, lack of serious consequences to infection, and survival after wild virus infection.

Diagnostic Assays

The peptides of the present invention, either alone or in combination with other measles peptides, could be used in diagnostic assays designed to determine whether the measles virus is present. One would preferably wish to analyze a biological sample taken from a human patient and detect the presence or absence of the peptides by means of specific antibodies or other probes. These peptides, perhaps in conjunction with other yet-to-be-identified measles-derived peptides, could also be used in diagnostic assays. Direct detection of these peptides is possible as a diagnostic modality proving the presence of recent measles virus either within a blood sample, or potentially directly within a tissue specimen (for example in trying to make the diagnosis of SSPE from a slice or biopsy of brain or other tissue).

In addition, because these peptides derive directly from the measles virus, antibody to these peptides unambiguously reflects the presence and/or previous exposure to either wild measles virus or measles vaccine virus. In the case of someone not previously immunized, the presence of IgM and/or IgG antibody to these peptides can only be attributed to infection with the measles virus. In the case of someone previously immunized against measles, an anamnestic (or long-term memory) immune response, measured by detection of IgM antibody to these peptides, is attributed to re-exposure and re-infection by wild measles virus.

These peptides could be directly incorporated onto plastic wells for use in an ELISA antibody assay, into microparticles in an ELISA or luminex technology assay, or even more generically into an ELISPOT assay. Conversely, it would also be possible to make monoclonal antibodies against these peptides, then make animal anti-human anti-measles peptides to these antibodies and use this in a biologic assay for the presence of antibody to these peptides. Thus, these peptides will ultimately also be utilized in the design of subunit antibody assays to these specific measles-derived peptides. It is important to note that the value of this approach may be the fine dissection of the immune response to an otherwise large virus. This assumes particular relevance when one considers that these peptides are in fact, the most prevalent measles-derived peptides as evidenced by the fact that these were found in high abundance on antigen-presenting cells by our methodology.

Other Immunostimulating or Immunotherapeutic Potential

The peptides of the present invention may have other immunostimulating or immunotherapeutic potential in applications. The peptides could be used to stimulate in combination with a variety of other antigens and immune response.

Since both N-1 and P-1 peptides have demonstrable immunostimulatory and immune memory recall properties in humans, it is also possible that these peptides along with SEQ ID NOs: 3-13 could be adapted to stimulate non-specific immune responses against other antigens such as other pathogens, tumors or malignant cells. For example, direct injection or transcutaneous application of these peptides, alone or in conjunction with one another and/or an adjuvant, into warts caused by human papillomavirus infection, perhaps in the setting of a measles immune host, could lead to the "bystander" effect of destruction of the HPV-infected cells (wart). Similarly, we have taken measles virus, injected directly into malignant lymphoma cells, and demonstrated in animal models, significant clearing of the malignant cells (Grote, et al., *Blood* 97:3746-3754, 2001). It may therefore be possible that in the setting of a person immune to measles, that injection or delivery of these measles-derived peptides into a tumor, would lead to an immune response that could destroy the surrounding malignant tissue. We are currently conducting human clinical trials to examine the effect of measles virus delivery into women with metastatic peritoneal ovarian cancer and into persons with malignant glioblastoma (brain tumors) to observe the extent of malignant tissue destruction elicited by the anti-measles immune responses.

Similarly, it is also possible that these peptides, combined with vaccines against other pathogens, could "boost" the immune responses to the pathogen of interest, by acting themselves as vaccine adjuvants.

EXAMPLES

Example 1

Identification of MV-PI

Results

Identification of the Measles-Specific HLA-DR3 Peptides by 2D nLC Tandem-MS

Figure 2:
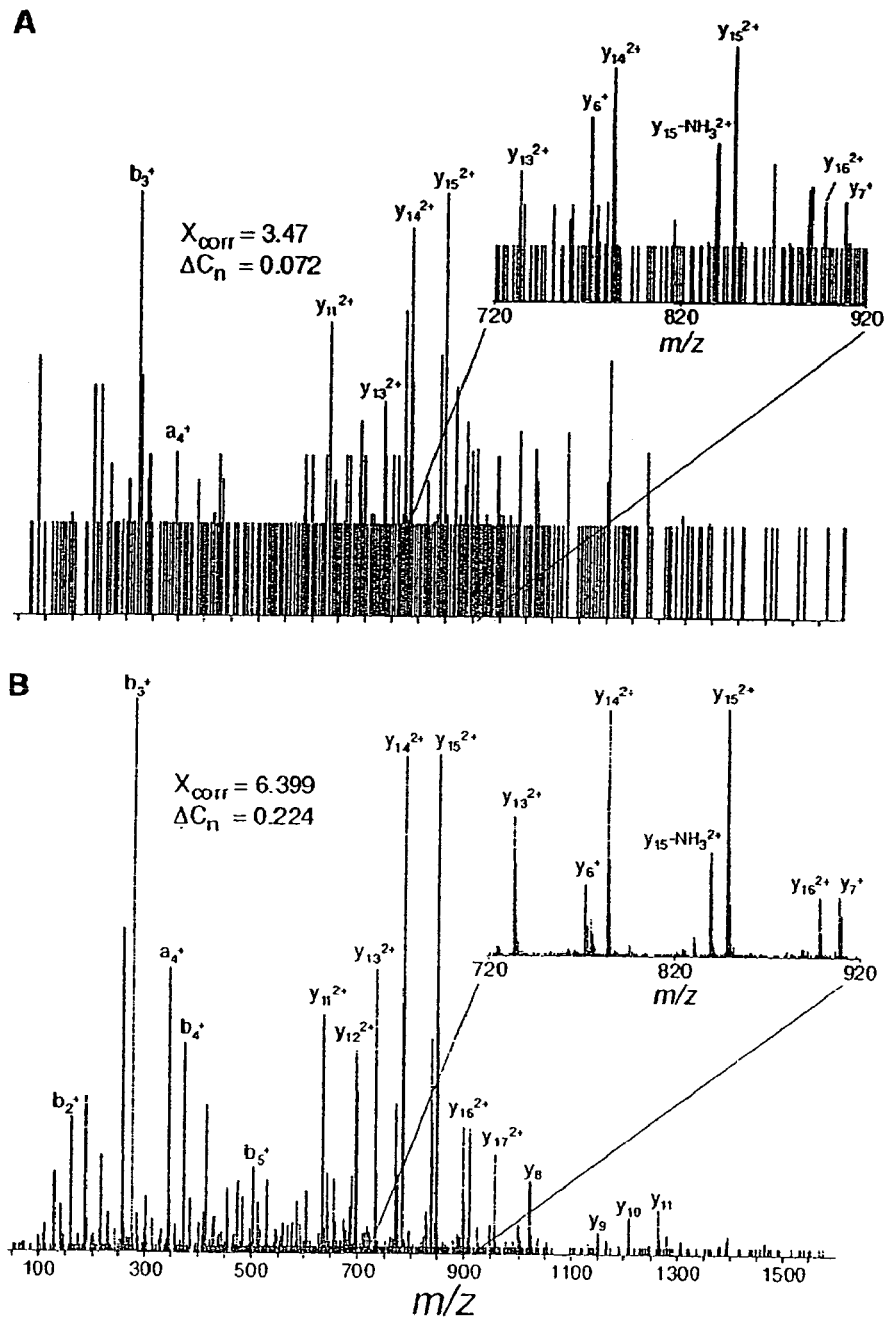
FIG. 2 shows a tandem mass spectra of m/z=689.7 obtained from the 40 mM SCX fraction with their corresponding SEQUEST scores.

An aliquot representing 25% of the peptide extract from $10^9$ measles virus infected cells was subjected to 2-dimensional nLC, data dependent tandem-MS and acquired a total of 1,371 tandem mass spectra from 10 SCX fractions. Peptide sequences were identified by searching the spectra against a subset of the NR database from NCBI using SEQUEST software (Eng, et al., *Am. Soc. Mass Spectrom.* 5:976-989, 1994). Search results were initially filtered on the basis of their cross-correlation score ($X_{Corr}$>2). From the 1371 tandem mass spectra acquired, 276 spectra met the search criteria, of which only one spectrum returned a search result for a measles virus peptide. The tandem mass spectrum of a triply-charged precursor with a m/z=689.69 ([M+H$^+$]$^+$=2067.0$_5$), eluting in the 40 mM KCl SCX fraction, returned a SEQUEST search result where the two top ranked sequences were peptides from multiple database entries for phosphoproteins from the measles virus (FIG. 2a). The two candidate sequences, SEQ ID NO:2 (designated MV-P1) and SEQ ID NO:14 (designated MV-P2), differ only by one amino acid, a Glu (E) versus Lys (K) at position 192.

Although the search statistics did not conclusively rule out the MV-P2 sequence, the difference between the two candidate sequences, MV-P1 and MV-P2, is a non-conservative amino acid change that can readily be distinguished solely by molecular weight as the peptide ion mass differs by 1 Dalton. The experimental monoisotopic mass for the naturally processed peptide was [M+H$^+$]$^+$=2067.05, while the theoretical values for MV-P1 and MV-P2 are 2067.03 and 2066.09, respectively, clearly in agreement with MV-P1 (~10 ppm mass error vs. nearly 500 ppm for MV-P2). Several of the expected product ions from synthetic MV-P2 are also one mass unit lower than the observed product ions in the naturally processed spectrum (data not shown).

The tandem mass spectra of synthetic MV-P1 (FIG. 2b) relative to the naturally processed peptide (FIG. 2a) are quite similar. Although product ions in the tandem mass spectrum from the naturally processed peptide (FIG. 2a) are only marginally more intense than noise, a series of doubly charged y product ions ranging from $y_{11}$ to $y_{16}$, as well as the singly charged $b_2$, $b_3$, and $a_4$ product ions, are observed for both the naturally processed and synthetic peptides which resulted in significant cross-correlation ($X_{corr}$) and $\Delta C_n$ scores (FIGS. 2a and b) (Smith, et al., *Proteomics* 2:513-523, 2002; Eng, et al., supra, 1994).

To be prudent, we carried out additional measurements to ensure confident identification of the naturally processed MHC Class II peptide. First, we used the synthetic MV-P1 peptide to optimize the collision energy for the tandem MS experiments (optimized collision voltage of 24 V shown in FIGS. 3a and b versus 26.8 V for the data shown in FIGS. 2a and b). Second, we adopted a more focused data dependent analysis where m/z=689.7 was selected as a priority precursor ion and the survey scan was restricted to m/z=650 to 720. Although this strategy does not enhance the minimum level of detection, it acts as an additional dimension of separation in the gas-phase that focuses data dependent acquisition on fewer potential precursor peptides at the expense of having to carry out multiple runs (Spahr, et al., *Proteomics* 1:93-107, 2002). Third, we used an aliquot representing 50% of the total extract in an attempt to improve the signal-to-noise ratio of the product-ion spectrum. Fourth, we designed a standard addition experiment to determine if the synthetic peptide co-eluted in the same SCX fraction and subsequently had the same RP retention time as the naturally processed sample (i.e., an increase in the signal-to-noise for the spiked sample).

Figure 3:
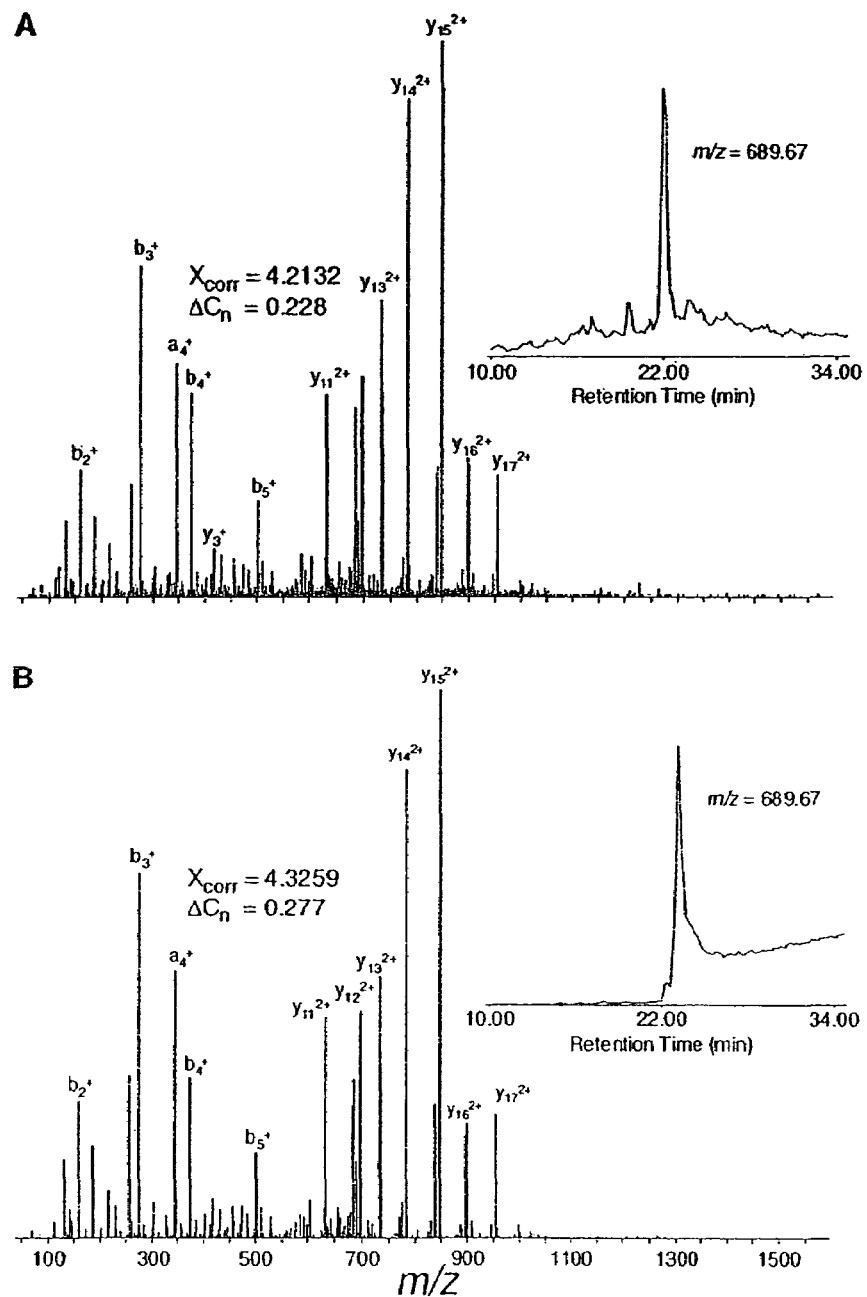
FIG. 3 illustrates a tandem mass spectra of m/z 689.7.

We analyzed an aliquot representing 50% of the total extract by 2-dimensional nLC tandem-MS after replacing the SCX, $C_8$, and $C_{18}$ columns with new columns that had not seen any synthetic MV-P1 peptide or naturally processed peptide extracts. These experiments again yielded a tandem mass spectrum for m/z 689.65 (FIG. 3a) eluting in the 40 mM KCl fraction. A small amount of this m/z was also detected, at the same reversed phase retention time, in the 60 mM KCl fraction. For the standard addition experiment, 500 femtomoles of synthetic MV-P1 was spiked, prior to the initial desalting step described in the methods, into the remaining aliquot of peptide extract representing 17% of the total. Synthetic MV-P1 eluted predominantly in the 40 mM SCX fraction (65% of total response) with 21% of the total response being detected in the 20 mM KCl fraction and 14% in the 60 mM KCl fraction. The tandem mass spectrum of the co-eluting synthetic MV-P1 and naturally processed MV-P1 from the 40 mM KCl fraction is shown in FIG. 3b. Clearly, the synthetic peptide behaves identically to the naturally processed peptide identified in earlier experiments (FIG. 2a). Thus, we conclude that we have identified the naturally processed peptide as being SEQ ID NO:2 (MV-P1), from the measles virus phosphoprotein.

Finally, by comparing the relative responses from the standard addition experiment (FIG. 3b) to the naturally processed sample (FIG. 3a), we estimate that the tandem MS spectrum represents approximately 20 femtomoles of the naturally processed peptide (FIG. 3a). Relative to responses observed for other peptides from endogenous proteins, the MV-P1 peptide is a minor epitope, where the more abundant endogenous peptides were observed with 100-fold higher MS responses than observed for MV-P1.

Proliferative Response of Vaccinated Donors to Measles P1 and P2 Peptides

Figure 4:
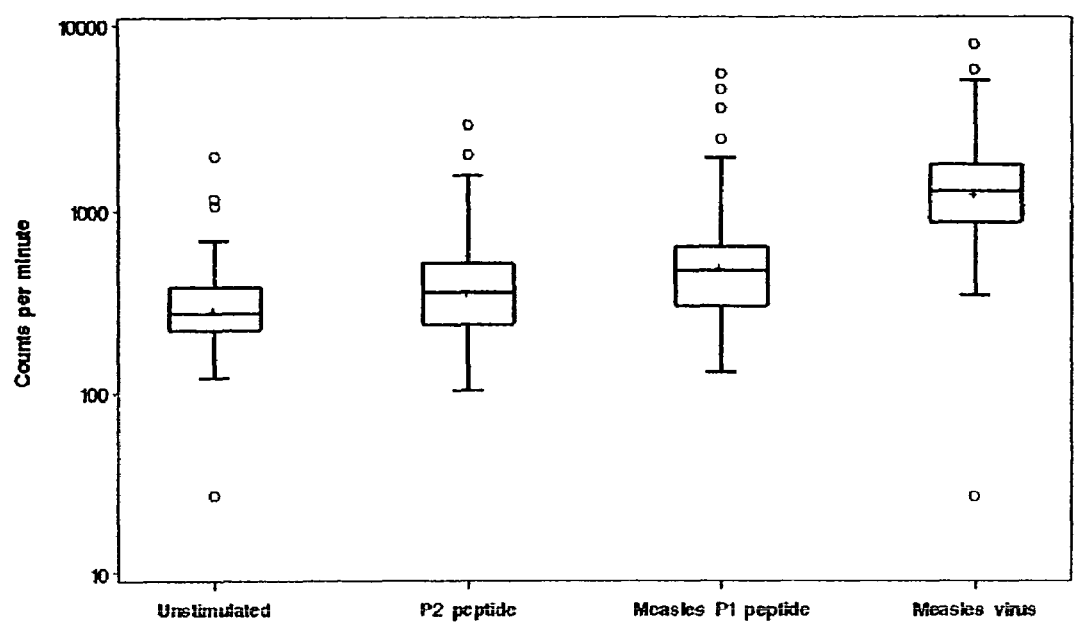
FIG. 4 illustrates box plots of counts per minute (cpm) of lymphoproliferative responses. Values are presented on a log scale. Top and bottom of boxes represent the third and first quartiles, respectively. Middle line represents median, plus sign represents mean, and whiskers represent values falling within 1.5 times the interquartile range to either side of the first and third quartile. Circles represent outliers falling outside of the whiskers.

We examined recognition of these measles-derived peptides by peripheral blood T cells from 95 healthy subjects previously immunized with measles-mumps-rubella-II (MMR-II) vaccine as a means of determining the biologic and immunologic relevance of these peptides. Peripheral blood mononuclear cells (PBMC) from vaccinated subjects were responsive to synthetic P1 and P2 peptides in vitro. The results revealed large inter-individual variation among 95 tested subjects, but we observed little variability between experiments on the same subject. FIG. 4 shows the distribution of counts per minute (cpm) in lymphoproliferative assays. Using a cut off value for significant lymphoproliferative responses (SI≧3), the stimulatory responses could be grouped into the following patterns of response. The median cpm value was lower for unstimulated cells (cpm=274) than for MV vaccine (cpm=1277, P<0.001), measles-derived P1 (cpm=472, P<0.001), and P2 (cpm=359, P<0.001) stimulated cells.

Figure 5:
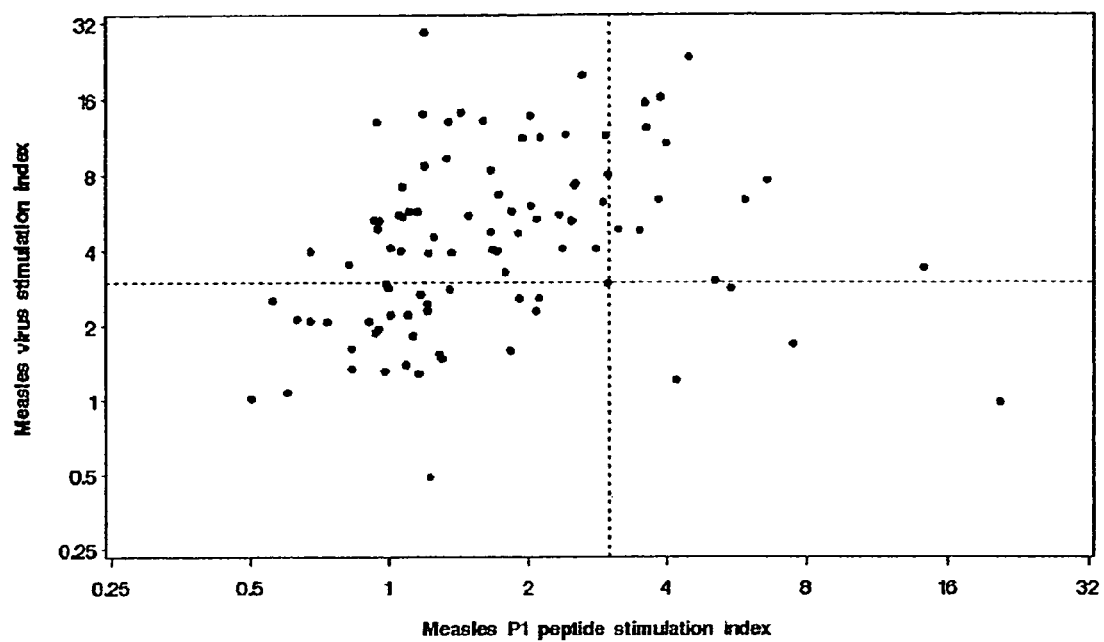
FIG. 5 is a plot of MV stimulation indices with measles P1 peptide stimulation indices. Values are graphed on a log scale. Dashed lines indicate proliferative responsiveness cut point of 3.0. Spearman rank correlation coefficient is 0.38 (P<0.001), sensitivity=0.20, specificity=0.89.
Figure 6:
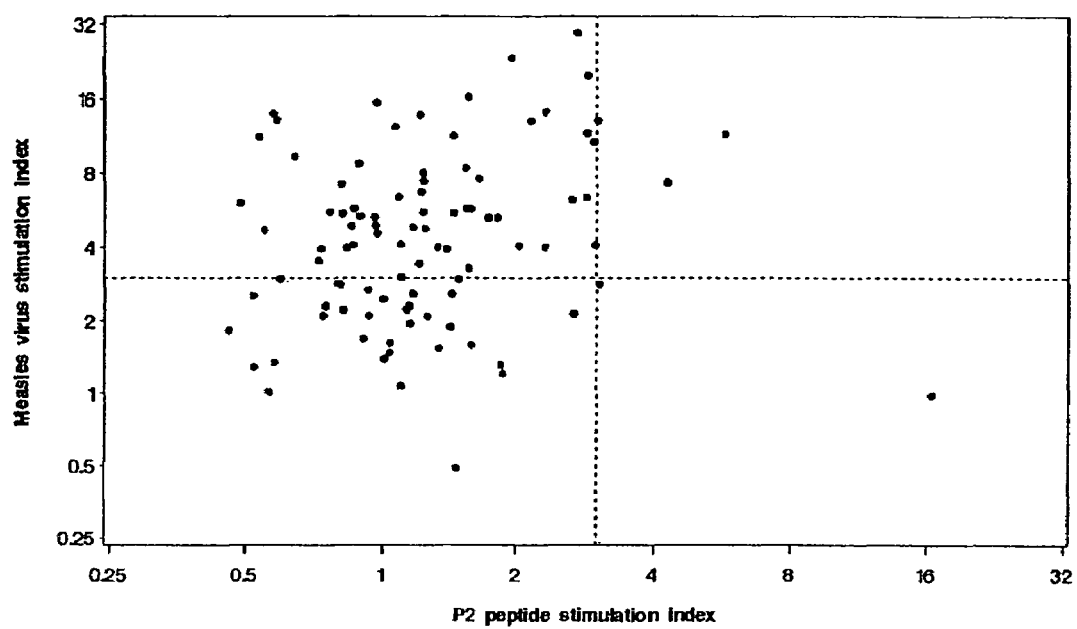
FIG. 6 is a plot of MV stimulation indices with measles P2 peptide stimulation indices. Values are graphed on a log scale. Dashed lines indicate proliferative responsiveness cut point of 3.0. Spearman rank correlation coefficient is 0.21 (P=0.04), sensitivity=0.05, specificity=0.94.

Measles virus-stimulation indices (median 4.1, range 0.5-29.1) were generally higher than measles P1 peptide (median 1.4, range 0.5-20.3) or P2 peptide stimulation indices (median 1.2, range 0.5-16.2). FIG. 5 and FIG. 6 indicate modest but positive correlations of MV-stimulated lymphoproliferative responses (SI) with P1 and P2 SIs (Spearman correlation coefficients=0.38 and 0.21, respectively) across all subjects. Sixty of the ninety-five subjects (63%) had MV stimulation indices greater than 3.0, indicating that measles vaccine virus contains multiple T cell epitopes. Comparatively, measles-derived P1 and P2 peptides were recognized in 17% and 5% of the subjects, respectively, thereby suggesting a higher frequency of P1-specific T cells in subjects after measles immunization. Among the sixty subjects who responded to the MV, twelve also responded to the P1 peptide (sensitivity=20%) and three responded to the P2 peptide (sensitivity=5%). We saw little or no proliferation in healthy subjects who were immunized with MMR-II vaccine to a randomly chosen irrelevant measles fusion (F) peptide from the MV proteome (data not shown). Thus, the lymphoproliferative response of the vaccinated subjects to naturally processed measles P1 peptide may be of further interest in studies to investigate induction of protective immunity to measles.

Discussion

The identification and characterization of antigenic epitopes of infectious pathogens by CD4+ T cells is of major interest (Peakman, et al., J. Clin. Invest. 104:1449-1457, 1999; Germain, supra, 1994a; Germain, et al., Nature 353: 134-139, 1991). In our study, we identified a HLA class II naturally processed peptide derived from MV phosphoprotein. The amino acid sequence of P1 peptide (SEQ ID NO:2) obtained from direct sequencing by nLC/MS/MS was concordant with the measles viral genome.

Measles is a negative-strand RNA virus. Measles virus P gene of Paramyxoviruses encodes three proteins: P polypeptide and two nonstructural gene products, C and V polypeptides, which encode virulence functions in vivo (Patterson, et al., Virology 267:80-89, 2000). The P gene encodes a heavily phosphorylated protein (60 kDa), which, in association with the polymerase (L) protein, is required for transcription and replication of the ribonucleoprotein complex (Griffin and Bellini, Measles virus. In "Fields Virology" (B. N. Fields, D. M. Knipe, P. M. Howley, Eds.), pp. 1267-1312. Lippincott-Raven, Philadelphia, 1996). In addition, P protein also acts as a chaperone that interacts with and regulates the cellular localization of nucleocapsid (N) protein and may assist in N assembly (Griffin and Bellini, supra, 1996; Horikami and Moyer, Curr. Top. Microbiol. Immunol. 191:35-50, 1995). Animals challenged with recombinant virus expressing the H, N or F measles structural protein were protected against measles encephalitis whereas matrix (M) or P protein immunization provided only partial protection (Brinckmann, et al, J. Gen. Virol. 72:2491-2500, 1991).

The significance of our results resides in a technique capable of identifying naturally processed pathogen-derived peptides eluted from the open peptide binding groove of class II HLA-DR and other class II molecules and the potential use of this technique in directed vaccine development. Furthermore, we established the immunologic relevance of these peptides by demonstrating their ability to induce recall immunity to measles in a lymphoproliferation assay among HLA discordant subjects. Previous investigations of in vitro PBMC proliferative responses to overlapping measles peptides was difficult, and often a short-term pre-culture with MV antigen and/or development of MV-specific T cell lines and T cell clones were needed to visualize the significant proliferative response (Marttila, et al., J. Gen. Virol. 80:1609-1615, 1999). We detected responses to a single P1 epitope, representing residues 179-197, in 17% of subjects without prior amplification of specific cells among HLA discordant subjects. The measles-derived P1 peptide is antigenic, as assessed by its capacity to be recognized by PBMC isolated from subjects previously immunized with measles vaccine. Since we obtained PBMC from the subjects with unknown HLA types (i.e. many were unlikely to be DR3 positive), it is likely that the number of true peptide responders is underestimated. We might, in fact, expect a low lymphoproliferative response among DR3 subjects, as the stimulating peptide is a "non-responder" peptide derived from DR3 positive subject. These data provide direct evidence that MV antigenic peptides were processed and could bind to HLA class II molecules. This information can only be obtained by direct elution from class II HLA molecules isolated from APC.

Isolation and identification of naturally processed and presented peptides greatly accelerates our ability to understand mechanisms of immunogenicity and further illustrates the importance of immunogenetics. It is both conceivable and likely that vaccine non-responders present a different spectrum of peptides to the immune system compared to vaccine responders. If so, the importance of HLA restriction in the immune response becomes primary in designing strategies to induce protective immune responses. Such an understanding also suggests an important approach to the directed design of new vaccines. It may be possible to design a vaccine that is a "cocktail" of peptides that induces protective immune responses across the spectrum of a population's HLA variability. The current limitation to this approach is the empiric and inefficient process of identifying which peptides are important in inducing a protective immunity, how they are HLA-restricted, and demonstrating the immunologic relevance of such peptides. Importantly, our results suggest an important advance, as our process could be applied to directed development of vaccines for any disease process where the stimulating antigen can be identified. For example, our approach may elucidate which tumor-specific peptides are presented to the immune system in a successful response to a given cancer. Similarly, new and safer vaccines against infectious diseases can be designed. For example, a peptide vaccine that induces immunity to the variola virus (smallpox) might allow universal immunization as opposed to the limitations imposed by a live, albeit attenuated, whole virus vaccine.

Materials and Methods

Donor Cell Preparation

We generated an EBV-B cell line from peripheral blood mononuclear cells (PBMC) of the an HLA-DR3 homozygous patient using $1 \times 10^7$ PBMC and the B95-8 strain of EBV (American Type Culture Collection, Manassas, Va.) in RPMI medium containing 1 µg/ml cyclosporin A (Neitzel, *Hum. Genet.* 73:320-326, 1986). We obtained a heparinized venous blood (20 U/ml heparin) sample from a single EBV-seronegative subject (KE, 16 year old female, DRB1*0301, A*1/3, B*8/44, C*7) who had been immunized with two doses of live attenuated measles vaccine (Attenuvax, Merck, West Point, Pa.). The subject had no previous history of measles infection. The circulating MV-specific IgG antibody titer in the subject's sera was determined by an IgG whole virus-specific EIA (MeasleELISA, BioWhittaker, Walkersville, Md.). The subject was characterized as a measles vaccine responder (EIA MV antibody titer=2.43 U/ml). B cells were sub cultured 4 to 6 times before being used as antigen-presenting cells (APC) and were routinely monitored for HLA-DR expression by flow cytometry.

Human Subjects

Study participants included ninety-five healthy residents of Olmsted County, Minn., aged 11 to 18 years. The subjects' medical records documented that each subject had been previously immunized with two doses of measles-mumps-rubella-II (MMR-II) vaccine (Merck Research, West Point, Pa.) containing the Edmonston strain of MV (tissue culture infective dose $TCID_{50} \geq 1000$) dose. All subjects resided in a geographic area where no wild type MV had circulated in the community during the subjects' lifetimes. The Institutional Review Board (IRB) of the Mayo Clinic granted approval for the study, and peripheral blood samples were drawn after informed consent was obtained from each subject. Mononuclear leukocytes were isolated by Ficoll-Hypaque (Amersham) density gradient centrifugation.

Cell Cultures and Virus Infection

We grew the Edmonston vaccine strain of measles in Vero cells, in Dulbecco's modified Eagle's medium, supplemented with 5% fetal calf serum (FCS) (virus stocks of $2.2 \times 10^7$ PFU/ml). Subsequently, EBV-B cells were infected with live MV at a multiplicity of infection (moi) of 1 PFU/cell for 1 hour and maintained for 36-48 h at 37° C. in RPMI-1640 containing 2% FCS (Life Technologies, Gaithersburg, Md.). Equally sized batches of MV-infected and uninfected cells were washed in PBS, pelleted and stored at −80° C. We monitored the infection of cells by flow cytometry using purified monoclonal antibody (mAb) specific for MV H protein tagged with FITC (Virostat, Portland, Me.) (Naniche, et al., *J. Virol.* 67:6025-6032, 1993) (data not shown).

Immunoaffinity Purification of HLA-DR3 Molecules and Associated Peptides

An overview of our methodological strategy has been previously published (Poland, et al., supra, 2001b). We used the same number of uninfected and MV-infected cells for HLA-DR-peptide complex purification. DR3 bound peptides were isolated from immunoaffinity purified class II molecules as previously described (Ovsyannikova, et al., *J. Immunol. Methods* 246:1-12, 2000; Kirschmann, et al., *J. Immunol.* 155:5655-5662, 1995). Briefly, 8-gram cell pellets consisting of either infected or uninfected cells were lysed in 1% CHAPS, 150 mM NaCl, 20 mM Tris-HCl, pH 8.0, and 1 mM Pefabloc SC (Boehringer Mannheim GmbH, Germany). The lysates were centrifuged at 100,000×g for 2 hours and the HLA-peptide complexes were immunoprecipitated from the supernatants using an anti-HLA-DR mAb specific for a HLA-DR monomorphic epitope (L227, IgG1) (Lampson and Levy, *J. Immunol.* 125:293-299, 1980) covalently linked to CNBr-activated Sepharose 4B beads (Sigma). The column was washed sequentially with five separate washings, first using 10 column volumes of lysis buffer; 5 column volumes of 0.1% deoxycholic acid (Boehringer Mannheim GmbH, Germany), 20 mM Tris, pH 7.4; 5 column volumes of 20 mM Tris, 500 mM NaCl, pH 7.4; 5 column volumes of 20 mM Tris, 150 mM NaCl, pH 7.4, then using 5 column volumes of 20 mM Tris, pH 7.4. After these series of wash steps, the HLA-DR-peptide complexes were eluted from the affinity column (pH 11.5) with 0.1% deoxycholic acid and 50 mM glycine. We neutralized the eluates with 2M glycine and concentrated in a Centricon-10 (Amicon, Beverly, Miami) before a second round of precipitation by 14% acetic acid to dissociate any bound peptides from DR3 molecules. HLA-DR3 molecules were more than 99% pure as assessed by SDS-PAGE. We determined protein concentration by BCA assay (Pierce, Rockford, Ill.). The peptides were concentrated in a spin vacuum to 100 µL aliquots ($1 \times 10^9$ cells) and stored at −80° C. for later analysis by MS.

Peptide Sequencing Methodology

HLA Class II-restricted peptides were sequenced using automated 2-dimensional liquid chromatography (strong cation exchange followed by nano-scale reversed phase, SCX and nLC, respectively) coupled via nano-electrospray, to a Micromass Q-Tof-2 tandem mass spectrometer (Micromass Ltd., Manchester, United Kingdom).

Prior to SCX, the peptide pool was desalted using a reversed phase micro-column (Peptide Trap, Michrom BioResources Inc., Auburn, Calif.). Desalted peptides, in SCX mobile phase A, were loaded on a 300 µm i.d. by 5 mm long column of Polysulfoethyl A (PolyLC, Inc., The Nest Group, Southborough, Mass.). Peptides were step-eluted from the SCX column using KCl concentrations of 20, 40, 60, 80, 100, 150, 200, 250, and 500 mM, and were re-concentrated on a pre-column before being chromatographed in the reversed phase dimension. The pre-column was 300 µm i.d. by 5 mm long (LC Packings, San Francisco, Calif.) packed with Magic $C_8$ (5 µm, 300 A), (Michrom BioResources Inc., Auburn, Calif.). SCX mobile phase A was water/acetonitrile/n-propanol (95/4/1 v/v/v), containing 10 mM potassium phosphate, pH=3.1.

We performed a nano-scale LC in a 75 μm i.d. PicoFrit column (New Objective, Woburn, Mass.) packed with 5.5 cm of Magic $C_{18}$AQ (5 μm, 200 Å), (Michrom BioResources Inc., Auburn, Calif.). Reverse mobile phase A was water/ acetonitrile/n-propanol (98/1/1 v/v/v) with a 0.2% overall concentration of formic acid. Reverse mobile phase B was acetonitrile/n-propanol/water (80/10/10 v/v/v) containing 0.2% formic acid overall. An LC pumping system, operated at 30 μL/min and split to 300 nL/min just prior to the switching valve, was used to generate a mobile phase gradient from 0 to 50% B through the reversed phase nLC column after each salt elution step.

We conducted tandem-MS experiments on precursor ions from doubly, triply, or quadruply charged ions within the m/z range of 450-1300; the collision energies were automatically selected as a function of m/z and charge (unless noted otherwise in the text) using argon as the collision target. Tandem mass spectra were searched, using SEQUEST software (ThermoFinnigan, San Jose, Calif.), against the combined subset of human, bovine, and measles proteins from the NR database (as available February, 2002 from ftp://ftp.ncbi.nih.gov/blast/db/nr) (Eng, et al., supra, 1994).

Synthetic Peptides

Identified peptides were subsequently synthesized by the Mayo Protein Core Facility (Rochester, Minn.) using N-(9-fluorenyl)methoxycarbonyl protection chemistry and carbodiimide/N-hydroxybenzotriazole activation on a MPS 396 Multiple Peptide Synthesizer (Advanced Chemtech, Louisville, Ky.). We purified each peptide by RP HPLC, and verified by mass spectrometry and amino acid (aa) analysis.

The following three peptides were used: (1) MV-derived naturally processed 19 aa P1 (MV-P1) peptide of the measles P protein having SEQ ID NO:2; (2) MV-P2 peptide having SEQ ID NO:14; and (3) MV-F control peptide of the MV fusion protein having SEQ ID NO:15, randomly chosen from MV F glycoprotein. Measles F control peptide was chosen for this study because of the established importance of measles F protein in cell-mediated immune response. In addition, Bakouche, et al. show that the F protein of MV is a potent T cell antigen (Bakouche, et al., *Immunology* 62:605-611, 1987). The MV sequence corresponds to the Edmonston strain (Parks, et al., *J. Virol.* 75:910-920, 2001).

T Cell Proliferation Assay

We tested three measles-derived peptides (MV-P1, MV-P2 and MV-F) for the capacity to induce recall peptide-specific proliferative responses. PBMC ($2 \times 10^5$) were incubated in medium (RPMI-1640, supplemented with 5% autologous sera, penicillin, 100 U/ml, 2-mercaptoethanol and sodium pyruvate) alone or in the presence of phytohemagglutinin (PHA, 5 μg/ml) to assess cell vitality, or in the presence of measles synthetic peptides in a concentration of 20 μg/ml, or live attenuated MV (50 PFU/well), (Attenuvax, Merck, West Point, Pa.). Cultures were incubated in a total volume of 200 μl for 3 days (37° C., 5% $CO_2$) and pulsed during the last 18 hours with tritiated thymidine [$^3$H] (1 μCi/well). We then harvested cells onto glass fiber filters, using a 96-well harvesting system (Skatron Instruments, Norway). The amount of incorporated radioactivity was determined by a liquid scintillation counter (Packard Instrument Company, Boston, Mass.) and the results were expressed as SIs. We calculated the SI as the ratio of mean cpm of triplicate wells of peptide stimulated to mean cpm of unstimulated control wells. Stimulation indices of $\geq 3$ were considered to represent significant responses (Bautista-López, et al., *Vaccine* 18, 1393-1401, 2000; Marttila, et al., supra, 1999). We used six replicates of cpm values for unstimulated cells, three replicates each were used for T cells stimulated with MV-P1, MV-P2, MV-F and live attenuated MV vaccine. For each subject, median cpm was calculated for unstimulated cells, as well as for cells stimulated with MV-P1, MV-P2, and MV. These median values are used in all subsequent comparisons. Stimulation indices were calculated for MV-P1, MV-P2, MV-F peptides and MV using the median of the six unstimulated cpm values as the denominator.

Statistical Analysis

For descriptive analyses, we used medians and ranges for continuous variables and frequencies for categorical variables. We compared cpm for MV-stimulated, MV-P1-stimulated and MV-P2-stimulated cells with unstimulated cells using Wilcoxon signed rank tests. Associations between the continuously distributed stimulation indices for MV-P1, MV-P2 peptides, and MV were determined using Spearman rank correlation coefficients. Stimulation indices were subsequently dichotomized into positive or negative using a cut point of 3.0. We then compared MV positivity with MV-P1 and MV-P2 positivity using estimates of sensitivity.

Example 2

Identification of MV-N

In this study, we report the discovery of another HLA class II peptide, having SEQ ID NO:1, derived from the measles nucleoprotein (MV-N). This peptide was also identified from the population of peptides presented by class II HLA-DRB1*0301 molecules. Additionally, we describe results of the ability of these measles P and N peptides to stimulate measles-specific T cells from the blood of previously immunized subjects. Finally, we determine which alleles of the HLA-DRB1 locus are most strongly associated with these HLA class II epitopes.

Materials and Methods

Donor Cells, Cell Lines and Virus Infection

Our methods for donor cell preparation and MV infection have been previously described (Ovsyannikova, et al., supra, 2003). In brief, we generated an EBV-transformed B cell line from PBMC of an HLA-DRB1 homozygous individual using the B95-8 strain of Epstein-Barr virus (EBV) (American Type Culture Collection, Manassas, Va.) in RPMI medium containing 1 μg/mL cyclosporine A (Neitzel, *Hum. Genet.* 73:320-326, 1986). We obtained a heparinized venous blood (20 U/mL heparin) sample from a single EBV-seronegative subject (16 year old female, DRB1*0301, A*1/3, B*8/44, C*7) who had been immunized with two doses of live attenuated measles vaccine (Attenuvax, Merck, West Point, Pa.). The subject had no previous history of measles infection. The circulating MV-specific IgG antibody titer in the subject's sera was determined by an IgG whole virus-specific EIA (MeasleELISA, BioWhittaker, Walkersville, Md.). The subject was characterized as a measles vaccine responder (EIA MV antibody titer=2.43 U/mL).

The Edmonston-Enders vaccine strain of measles was cultured in African green monkey kidney cells in Dulbecco's modified Eagle's medium, supplemented with 5% FCS (virus stocks of $2 \times 10^7$ PFU/mL). Subsequently, EBV-B cells were infected with live MV at a moi of 1 PFU/cell for 1 hour and maintained for 24-36 hours at 37° C. in RPMI 1640 supplemented with 2% FCS (Life Technologies, Gaithersburg, Md.). Equal-sized batches of MV-infected and uninfected cells were washed in PBS, pelleted and stored at −80° C. Evidence for the infection of cells was monitored by flow cytometry using purified mAb specific for MV hemagglutinin protein tagged with FITC (Virostat, Portland, Me.) (Naniche, et al., *J. Virol.* 67:6025-6032, 1993).

Isolation of HLA-DRB1*0301 Molecules and HLA-Bound Peptides

Our methodological strategy has been previously published (Poland, et al., *Vaccine* 19:2692-2700, 2001). We used the same cellular mass of uninfected and MV-infected cells for HLA-DRB1-peptide complex purification. DRB1 bound peptides were isolated from immunoaffinity purified class II molecules as previously described (Kirschmann, et al., *J. Immunol.* 155:5655-5662, 1995). Briefly, 8-gram cell pellets consisting of either infected or uninfected cells were lysed in 1% CHAPS, 150 mM NaCl, 20 mM Tris-HCl, pH 8.0, and 1 mM Pefabloc SC (Boehringer Mannheim GmbH, Germany). The lysates were centrifuged at 100,000×g for 2 hours and the HLA-peptide complexes were immunoprecipitated from the supernatants using an anti-HLA-DR mAb specific for a HLA-DR monomorphic epitope (L227, IgG1) (Lampson and Levy, *J. Immunol.* 125:293-299, 1980) covalently linked to CNBr-activated Sepharose 4B beads (Sigma-Aldrich Corp., St. Louis, Mo.). The column was washed sequentially with five separate washings and the HLA-DRB1-peptide complexes were eluted from the affinity column with 0.1% deoxycholic acid and 50 mM glycine, pH 11.5. We neutralized the eluates with 2M glycine and concentrated in a Centricon-10 (Amicon, Beverly, Mass.) before a second round of precipitation by 14% acetic acid to dissociate any bound peptides from DRB1 molecules. We determined protein concentration by BCA assay (Pierce, Rockford, Ill.). The peptides were concentrated in a spin vacuum to 100 µL aliquots ($1\times10^9$ cells) and stored at −80° C. for later analysis by MS.

Identification of Measles-Derived P and N Peptides by 2D-Liquid Chromatography (LC)-Tandem Mass Spectrometry (MS/MS)

The analytical methods used for identification of the measles P peptide have been described in detail (Ovsyannikova, et al., supra, 2003). Briefly, the complex peptide pool dissociated from HLA class II molecules was separated by two dimensions of automated chromatography: strong cation exchange (SCX) on a 0.3 mm (inner diameter [i.d.])- by 5-mm long column, followed by nano-scale reversed phase (RP) liquid chromatography (LC) using a 75 µm i.d. by 6 cm long PicoFrit column (New Objective Inc., Woburn, Mass.). Prior to the cation exchange separation, the peptide mixture was desalted on a RP column (1 mm i.d. by 10 mm i.d. PeptideTrap, Michrom BioResources Inc., Auburn Calif.). The eluant from the desalting cartridge was concentrated to dryness on a vacuum-centrifuge and reconstituted in SCX mobile phase A (5 mM $KH_2PO_4$, pH 3.0, containing 1% n-propanol and 4% acetonitrile) before loading peptides onto the SCX column. The SCX separation was performed using step elutions of increasing KCl strength in SCX mobile phase A. As peptides eluted from the SCX column as a function of their positive charge, they were re-concentrated on a reversed phase pre-column within the LC 10-port sampling valve. The pre-column was then washed with mobile phase A from the reversed phase separation (water/acetonitrile/n-propanol/formic acid, 98/1/1/0.2 v/v/v/v) before placing the precolumn in-line with the nano-LC column for separation in the second dimension by RP nano-LC-MS/MS.

Nano-LC-MS/MS experiments were performed on a quadrupole-time of flight mass spectrometer (Micromass Q-Tof 2, Manchester UK). MS/MS spectra were acquired in an automated data dependent manner using survey scans to select doubly, triply, or quadruply charged ions. Argon was used as the target collision gas. Collision energies were automatically chosen as a function of m/z and charge (z). For the MV-N peptide identified in this report, collision energy of 26 eV was used for the doubly charged ion at m/z 653.8 for both the naturally processed and synthesized peptide.

For increased MS/MS coverage of class II peptides, the m/z range for the survey scan was reduced from m/z 450-1300 to smaller overlapping ranges. This enhanced our ability to identify minor peptides within the reduced m/z range, a technique referred to as "gas phase fractionation" (GPF) (Spahr, et al., *Proteomics* 1:93-107, 2002). Database searching of MS/MS spectra was conducted using Sequest software (Thermo-Finnigan, San Jose, Calif.). Spectra were searched against the NCBI nr database (downloaded from NCBI, February 2002).

Peptide Synthesis

Identified peptides were subsequently synthesized by the Mayo Protein Core Facility (Rochester, Minn.) using N-(9-fluorenyl)methoxycarbonyl protection chemistry and carbodiimide/N-hydroxybenzotriazole activation on a MPS 396 Multiple Peptide Synthesizer (Advanced Chemtech, Louisville, Ky.). We purified each peptide by RP HPLC, and verified accuracy by MS and amino acid (aa) analysis. The following naturally processed synthetic peptides were used: (1) Measles-derived 14 aa peptide from measles nucleoprotein (MV-N, residues 372-385), having SEQ ID NO:1; and (2) measles-derived 19 aa peptide from the measles phosphoprotein (MV-P, residues 179-197), having SEQ ID NO:2.

Study Subjects

Study participants were enrolled as part of a larger stratified random sampling study to assess associations between HLA class I and II genes and the immune response to rubella virus vaccine in healthy, school-age children and young adults in Rochester, Minn. To evaluate the immunogenicity of measles-derived peptides, 281 of these subjects (age 12 to 18 years) were studied. All enrolled subjects had been previously immunized with two doses of measles-mumps-rubella-II (MMR-II) vaccine (Merck Research, West Point, Pa.) containing the further attenuated Edmonston strain of MV (tissue culture infective dose $TCID_{50} \geq 1000$). In addition, all subjects resided in a geographic area where no wild-type MV had circulated in the community during the subjects' lifetimes. The Institutional Review Board of the Mayo Clinic granted approval for the study, and peripheral blood samples were drawn after written informed consent was obtained from each subject and/or guardian.

Molecular HLA Typing

Genomic DNA was extracted from frozen blood samples (5 mL each) by conventional techniques using PYREGENE extraction kit (Gentra Systems Inc., Minneapolis, Minn.). DNA was used for class II HLA-DRB1 allele typing by high resolution DRB96 SSP (sequence-specific primer) Unitray typing kits with the entire locus on a single fray (Pel-Freez Clinical Systems, LLC, Brown Deer, Wis.) (Büchler, et al., *Hum. Immunol.* 63:139-142, 2002). Locus-specific primers were used to amplify the HLA-DRB1 locus. PCR products were separated on 2% agarose gels and stained with ethidium bromide. Any ambiguities were resolved using the ABI DRB1 sequencing kit (Applied Biosystems, Foster City, Calif.). All PCR amplifications were carried out in a Gene-Amp PCR system 9600 (Perkin ElmerCetus Instruments). All reactions were run with negative controls and every $50^{th}$ PCR reaction was repeated for quality control.

Preparation of Peripheral Blood Leukocytes

PBMC were separated from heparinized venous blood by Ficoll-Hypaque (Sigma, St. Louis, Mo.) density gradient centrifugation and washed in complete RPMI 1640 medium (Celox Laboratories, Inc., St. Paul, Minn.) supplemented with 2 mM L-glutamine, 100 µg/mL streptomycin, 100 U/mL penicillin and 8% heat-inactivated FCS (Life Technologies, Gaithersburg, Md.). Cells were then counted, resuspended in a freezing medium containing 10% dimethyl sulfoxide, frozen at −80° C. and stored in liquid nitrogen until cultured. No significant differences in cellular viability estimated by trypan blue exclusion were observed between the same PBMC samples obtained before and after their storage in liquid nitrogen.

Measurement of IFN-γ and IL-4 Supernatant Cytokine Response to Measles Virus and Synthetic Measles Peptides Cryopreserved PBMC were used to measure cytokine responses to measles-derived peptides. We thawed cryopreserved PBMC at a concentration of $1 \times 10^7$ cells/mL using standard protocol. The vials were rapidly thawed in a 37° C. water bath and then washed twice with 10× volume of complete RPMI 1640 media supplemented with 10% FCS at 700 rpm for 5 minutes. The final cell pellet was resuspended in complete RPMI media containing penicillin-streptomycin (100 U/mL) supplemented with 5% normal human AB sera (Ervin Sci., Santa Ana, Calif.). For IFN-γ determination, thawed PBMC were cultured at a concentration of $2 \times 10^5$ in RPMI containing 5% normal human AB sera with or without measles peptides (10 µg/well) and MV (positive control) at a moi of 0.5 for 6 days. For IL-4 determination in cell culture supernatants, we cultured thawed PBMC at a concentration of $4 \times 10^5$ in RPMI media, supplemented with 5% normal human AB sera. Cells were cultured in the presence of 2 µg/mL of IL-4 receptor antibody (R&D Systems, Minneapolis, Minn.) (Ekerfelt, et al, *J. Immunol. Methods* 260:55-67, 2002) with or without synthetic measles-derived peptides (10 µg/well) and MV (positive control) at a moi of 0.1 for 6 days. Cell culture supernatants were collected in a volume of 150 µl/well for both IFN-γ and IL-4 and were frozen at −80° C. until assayed. The culture supernatants were assayed using a standard ELISA protocol (OptiEIA Human IFN-γ and IL-4, PharMingen, San Diego, Calif.) at a dilution of 1:1 in PBS containing 10% FCS. ELISA plates (Immulon-4, DYNEX Technologies Inc, Chantilly, Va.) were coated with capture IFN-γ or IL-4 mAb and incubated overnight at 4° C. The antibody-coated plates were incubated with diluted supernatant samples for 2 hours at room temperature followed by incubation with biotinylated mouse anti-human IFN-γ or IL-4 conjugated to avidin-horseradish peroxidase for 1 hour at room temperature. The absorbance of the product was read using a microplate reader (Molecular Devices, Sunnyvale, Calif.) at 450 nm. The IFN-γ and IL-4 concentration of test samples was calculated by reference to the standard curve. Unstimulated and MV-stimulated secretion measurements for IFN-γ were performed in triplicate, while all other secretion measurements for both IFN-γ and IL-4 were performed in duplicate. Individual-specific values were then summarized by taking means of the duplicate or triplicate values. Mean background levels of IFN-γ and IL-4 cytokine production in cultures not stimulated with measles peptides or MV was subtracted from the mean antigen-induced responses to produce "corrected" secretion values. Negative corrected values indicate that the unstimulated secretion levels were, on average, higher than the stimulated secretion levels.

Two criteria were established to define positive responses for secreted IFN-γ and IL-4 cytokines using ELISA. First, positive responses were identified if the mean cytokine level in peptide or MV-stimulated replicate cultures exceeded 1.645 standard deviations of the mean of control replicate samples from the same individual, akin to detecting a p-value of 0.05 using a one-sided test of hypothesis. Second, the difference between the mean of peptide or measles stimulated cultures and that of control cultures was determined for each subject. Several cut-off values between 5 and 30 pg/mL were assessed for their ability to stratify subjects into positive and negative groups in accordance with the first statistical criteria described above. Hence, a minimum difference of 20 pg/mL for IFN-γ and 10 pg/mL for IL-4 between a stimulated and a control culture was selected as the optimal threshold to define a positive response. The data were analyzed by SoftMax-Pro (Molecular Devices, Sunnyvale, Calif.).

Statistical Analysis

Six outcomes were of primary interest: two sets of in vitro cytokine production (both IFN-γ and IL-4) each induced separately by three stimuli (live MV and measles-derived MV-N and MV-P peptides). Data were descriptively summarized using frequencies and percentages for all categorical variables and medians and inter-quartile ranges for all continuous variables. Wilcoxon signed rank tests were used to determine whether the centers of the cytokine secretion value distributions differed from zero. Spearman rank correlation coefficients were used to summarize the associations between secretion values, namely those induced by MV against those induced by the two measles-derived peptides. Cytokine levels are reported as median values with interquartile range (IQR) in brackets ($25^{th}$%, $75^{th}$%).

Descriptive associations of the continuously distributed cytokine secretion values with HLA-DRB1 alleles were evaluated on an allelic level. Each person contributed two observations to this descriptive analysis—one for each allele. Alleles were grouped by HLA-DR type and summarized using medians and inter-quartile ranges. Following the descriptive comparisons, associations were more formally evaluated using linear regression analyses. In contrast to the descriptive comparisons, each subject contributed one observation to the regression analysis, based on his or her genotype. Regression variables were created for each allele and were coded as 0, 1, or 2, according to the number of copies of the allele that a subject carried. Rare alleles, defined as occurring fewer than five times among all subjects, were pooled into a category labeled "other." Due to data skewness, the original secretion values were replaced with corresponding rank values. Global differences in cytokine secretion levels among all alleles were first carried out by simultaneously including all but one of the allele variables in a multivariate linear regression model. Following these global tests, we examined individual allele effects on cytokine secretion levels. This series of tests was performed in the spirit of Fisher's Protected Least Significant Difference test; individual allele associations were not considered statistically significant in the absence of global significance. Each allele variable was included in a separate univariate linear regression analysis, effectively comparing secretion levels for the allele of interest against all other alleles combined. Two sets of allele variables were analyzed. We first evaluated each distinct observed allele subtype (for instance, we separately evaluated the effects of DRB1*0401, DRB1*0402, DRB1*0404 and DRB1*0407). We then pooled specific subtypes into more general groupings (for instance, we pooled all DR4 alleles into one overall category). All global and univariate regression analyses included the design variable, age, as a covariate.

Subsequent to the linear regression analyses, we assessed the association between categorized cytokine positivity values and DRB1 alleles using logistic regression analyses. Cutpoints for IFN-γ and IL-4 positivity were defined as 20 and 10 pg/mL, respectively, as described above. Univariate and multivariate analyses were carried out using the same general outline as the linear regression analyses. All statistical tests were two-sided, and all analyses were carried out using the SAS software system (SAS Institute, Inc., Cary, N.C.).

Results

Figure 7:
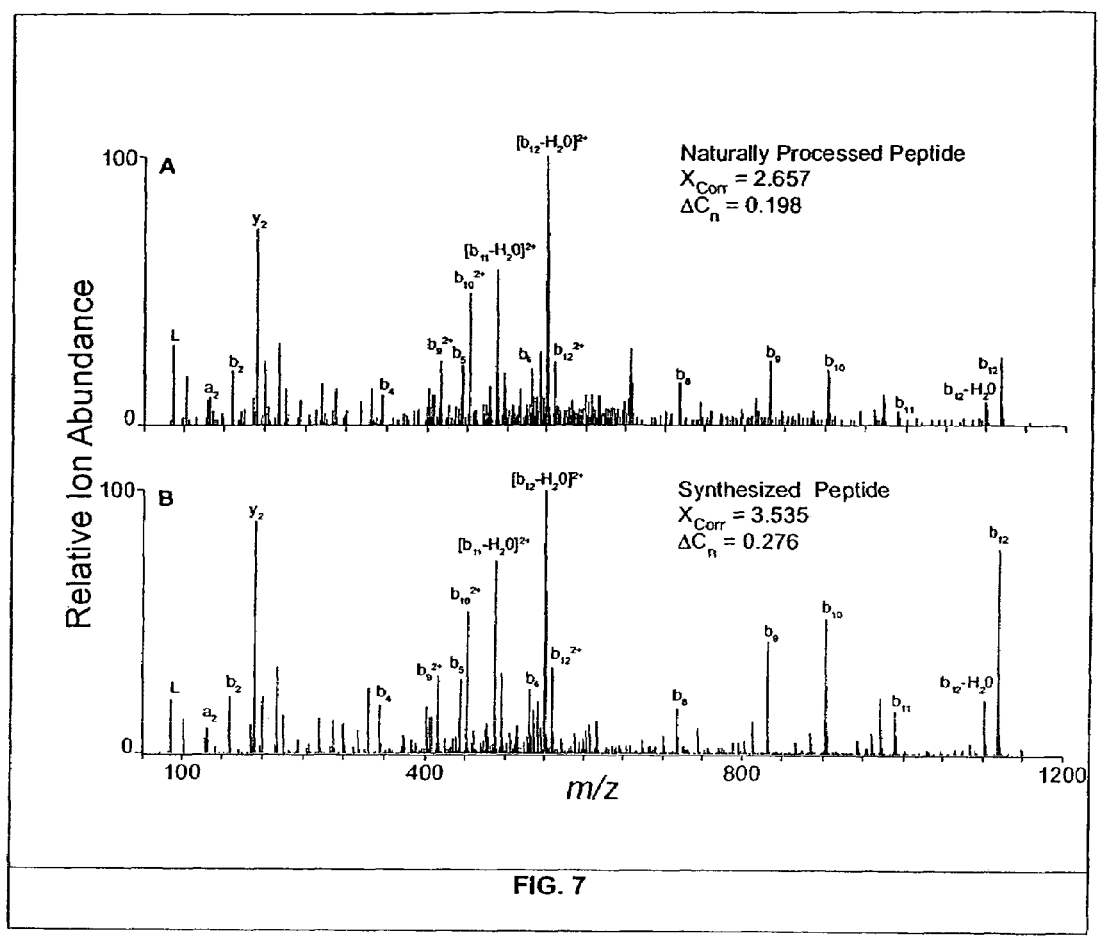
FIG. 7 illustrates MS/MS product ion spectra of A) products of m/z $653.8^{2+}$ a naturally processed HLA class II peptide identified as having SEQ ID NO:1 and is from the nucleoprotein of measles virus and B) products of m/z $653.8^{2+}$ from the synthesized peptide having SEQ ID NO:1. The naturally processed spectrum was generated using gas-phase fractionation in conjunction with 2D-LC-MS/MS. The synthesized peptide was analyzed by 1 D-LC-MS/MS. The Sequest scoring parameters $X_{Corr}$ and $\Delta C_n$ are shown and described in the text.

Identification of a Measles-Derived HLA-DRB1*0301 N Peptide by Nano-LC Tandem-MS From a data set using a reduced survey scan range of m/z 590-720, a peptide having SEQ ID NO:1 was the top match by Sequest database searching ($X_{Corr}$=2.657, $\Delta C_n$=0.198) of the MS/MS spectrum from a doubly charged precursor ion at m/z 653.82. This sequence is present in the NCBI nr database (NCBI, downloaded February 2003) as multiple entries annotated as the nucleoprotein or nucleocapsid protein of MV. To confirm this identification, the peptide was synthesized and analyzed by nano-LC-MS/MS. FIG. 7A shows the MS/MS spectrum of the naturally processed peptide identified as having SEQ ID NO:1, while FIG. 7B shows the MS/MS spectrum of the synthesized peptide. The top-ranked Sequest database search result for the synthesized authentic peptide was also SEQ ID NO:1 ($X_{Corr}$=3.535, $\Delta C_n$=0.276). Sequest scoring parameters of $X_{Corr}$>2.5 and $\Delta C_n$>0.1 are commonly used as thresholds for determining the uniqueness of database search results. Thus, the close agreement between fragment ions observed in the two spectra, as well as their discriminating Sequest scores, confirm our identification of the naturally processed doubly charged peptide at m/z 653.82 as originating from the measles nucleoprotein.

Cytokine Responses of Vaccinated Donors to Measles Virus, MV-P and MV-N Peptides We examined the ability of these measles-derived peptides to induce in vitro production of cytokines (IFN-γ and IL-4) by PBMC of 281 healthy subjects previously immunized with MMR-II vaccine. Cytokine secretion results revealed large inter-individual variation among the 281 tested subjects. An overall summary of the frequency and magnitude of the MV and peptide-specific induction of IFN-γ and IL-4 from vaccinated subjects' PBMC are shown in Table 1. Both MV and MV-P peptide were able to induce a recall peptide-specific IFN-γ response (>20 pg/mL) from PBMC of previously immunized subjects. Measles-specific IFN-γ responses were generally higher than MV-P or MV-N peptide-specific IFN-γ responses (p<0.001). Specifically, measles, MV-P and MV-N specific IFN-γ responses were detected in a total of 185 (65.8%), 157 (55.9%) and 43 (15.3%) of the 281 subjects, respectively. With regard to HLA-DRB1*0301, we found a marginally significant (p=0.08) increase in the frequency of *0301 allele among the subjects who produced IFN-γ in response to the MV-P peptide (12.4%) compared to those with low (<20 pg/mL) MV-P specific IFN-γ levels (8.1%, odds ratio (OR) 1.7; 95% confidence interval (CI) 0.93-2.99). By contrast, the frequency of *0301 alleles (OR, 0.4; CI 0.13-1.09, p=0.07) was lower in subjects with significant MV-N specific IFN-γ levels (4.6%) compared to individuals with low levels of IFN-γ to the MV-N peptide (11.5%).

Associations of IFN-γ measles virus secretion levels with those of measles-derived peptides were modest; observed Spearman correlations were 0.20 and 0.32 for the MV-P and MV-N peptides, respectively. Among the 185 subjects who responded to MV, 110 (59.5%) demonstrated IFN-γ production in response to the MV-P peptide and 39 (21.1%) responded to MV-N peptide, thereby suggesting a higher frequency of MV-P-specific T cells in subjects after measles vaccination. However, among the 157 subjects who responded to the MV-P peptide, only 33 (21%) also produced IFN-γ to MV-N peptide.

Comparatively, measles-specific IL-4 responses were higher than for MV-N peptide-specific IL-4 responses (p<0.001). MV-P peptide was able to induce only low levels of IL-4 production from PBMC of immunized subjects. Using a cutoff value for significant cytokine responses of >10 pg/mL, MV-specific IL-4 responses were detected in 50.9% (143/281) of subjects. In contrast, MV-P specific IL-4 responses were detected in only 19.2% (54/281) of subjects. Likewise, MV-N specific IL-4 responses were detected in a total of 23.1% (65/281) subjects. We found no association between the *0301 allele and MV-P specific IL-4 secretion level. With regard to the MV-N peptide, we found a marginally significant (p=0.08) increase in the frequency of the *0301 allele among subjects who produced significant IL-4 levels to the MV-N peptide (14.6%) compared to those with low levels of (<10 pg/mL) MV-N specific IL-4 secretion (9.3%, OR, 1.7; CI 0.94-3.14).

Spearman correlations of IL-4 measles secretion levels with those for MV-N and MV-P peptides were 0.12 and 0.28, respectively. Among the 143 volunteers who demonstrated IL-4 production from MV-stimulated PBMC, 33 (23.1%) subjects also responded to MV-P peptide, and 41 (28.7%) subjects responded to the MV-N peptide. Interestingly, among the 54 subjects who responded to the MV-P peptide, MV-N specific IL-4 responses were also detected in half of these subjects. These data suggest that both MV-derived epitopes exhibited the capacity to stimulate measles-specific T cells; however, the MV-N peptide was less stimulatory than the MV-P peptide.

Expression of HLA-DR Alleles in Study Subjects Previously Immunized with Measles All 281 subjects were HLA-typed and associations between recall peptide-specific cytokine responses and HLA-DR type and MV-P and MV-N peptides assessed. The most prevalent alleles in this study population (Table 2) were expressed at frequencies similar to the HLA-DRB1 frequencies published elsewhere (Doolan, et al., *J. Immunol.* 165: 1123-1137, 2000; Southwood, et al., *J. Immunol.* 160:3363-3373, 1998).

Associations between HLA-DRB1 Alleles and Measles-Derived HLA Class II Peptides

Analyses were performed for each of the 22 observed HLA-DRB1 alleles with allele frequencies greater than five. Tables 3, 4 and 5 present the results of the linear regression analysis of association with measles, MV-P and MV-N peptides and individual comparison of HLA-DRB1 alleles across the IFN-γ and IL-4 secretion status. Table 3 relates the HLA-DRB1 allelic associations with recall measles (positive control)-specific IFN-γ and IL-4 cytokine responses. The global test reveals a significant association between MV-specific IFN-γ secretion and the HLA-DRB1 locus (p=0.005). Allelic subtyping of HLA-DRB1 revealed that four subtypes, *0301 (p=0.02), *0701 (p=0.01), *1501 (p=0.004) and *0801 (p=0.05), which share largely overlapping peptide-binding repertoires (Southwood, et al., supra, 1998), were the predominant alleles and were significantly associated with measles-specific IFN-γ response in previously immunized study subjects. The less common subtypes, such as *0102 (p=0.08), *0404 (p=0.07) and *1103 (p=0.09) showed a trend toward IFN-γ response, although these were not statistically significant. In contrast, the global test for association failed to find a statistically significant association with measles-specific IL-4 cytokine responses (Table 3). Examining HLA-DRB1 alleles individually, we found suggestive associations with alleles *0103 (p=0.03), *0701 (p=0.02) and *1303 (p=0.04); however, these associations should be interpreted with caution due to the non-significance of the global test.

Measles-derived peptide (MV-P and MV-N)-specific cytokine responses and HLA-DRB1 alleles associations are summarized in Tables 4 and 5. Global tests revealed no significant associations of HLA-DRB1 alleles with peptide-specific cytokine levels. However, univariate analyses revealed intriguing results. For the MV-P peptide, the allele with the strongest association with both IFN-γ (p=0.02) and IL-4 (p=0.03) responses was DRB1*0301 (Table 4), confirming the DRB1*0301 origin of this class II measles-derived peptide and suggesting that MV-P contains both Th1 and Th2 cell epitopes. Examining alleles individually for recall IFN-γ MV-P responses, only alleles *0101, *0103 and *0404 provide suggestive evidence of an association. There were no strong associations (except for the *0301 allele) between the MV-P specific IL-4 levels and the frequency of other DRB1 alleles.

For the MV-N peptide, the allele providing the strongest evidence of an association with IFN-γ secretion was DRB1*1501 (p=0.04), and with IL-4 secretion the DRB1*1103 and DRB1*1303 (p=0.01) alleles, respectively, suggesting that MV-N is a promiscuous T cell epitope (Table 5). Although the global tests for the association of MV-N- and MV-P-specific cytokine responses and the DRB1 locus were not statistically significant, allele-specific analyses provide some hints for possible associations that would require confirmation in larger studies.

Sensitivity Analyses

All primary comparisons of cytokine response and DRB1 alleles use continuously distributed cytokine secretion values. We explored the categorization of subjects into positive vs. negative response for both IFN-γ (positivity cutpoint=20 pg/mL) and IL-4 (positivity cutpoint=10 pg/mL) using logistic regression analysis. Results were very similar to linear regression analysis results (data not shown).

Cytokine secretion was defined as the mean response of stimulated cells (measured either in duplicate or triplicate) minus the mean response of unstimulated cells (also measured either in duplicate or triplicate). We were concerned that simply taking mean values would fail to account for inherent variability observed within an individual. Thus, secondary models were fit using repeated measures analysis of variance techniques that accounted for intra-subject variability. P-values produced by these methods were similar to those presented in Tables 3-5.

Discussion

The characterization of highly stimulatory Th-epitopes generated from foreign pathogens has traditionally been used to better understand the requirements for a protective immune response (Urban, et al., Chem. Immunol. 57:197-234, 1993). However, the isolation and identification of naturally processed and presented pathogen-derived antigenic peptides has historically been extremely difficult. In our study we identified a new class II HLA-DRB1*0301 measles-specific epitope having SEQ ID NO:1, which is encoded by the measles N gene, using nano-LC/MS/MS methods. In addition, we demonstrated that an HLA class 1-derived MV-N peptide and a previously identified 19 amino acid peptide having SEQ ID NO:2 derived from measles P protein (MV-P), led to recall cytokine responses in immune individuals in vitro. Additionally, we have shown that these peptides can be recognized by human CD4+ T cells in association with different HLA-DRB1 alleles.

Measles-derived immunogenic peptides are generated in extremely low levels, and experimental data have shown the importance of peptide abundance in the development of an immune response (Santori, et al., *Immunity* 17:1001-1012, 2002; van Els, et al., supra, 2000; Velazquez, et al., *J. Immunol.* 166:5488-5494, 2002). Nevertheless, these low levels of class II peptides are sufficient to elicit an effective CD4+ T cell response against foreign peptides (Urban, et al., supra, 1993). We demonstrated the biologic functional significance of the measles-derived peptides we identified by directly comparing specific T cell cytokine responses induced by these peptides in HLA-DRB1*0301-positive and HLA-DRB1*0301-negative (HLA discordant) healthy subjects who had been previously immunized against measles during childhood. The immunologic relevance of the MV-P and MV-N peptides was established by performing lymphocyte stimulation of each subject's PBMC in vitro. IFN-γ was studied because it may be considered a signature marker of Th1-type immune responses and because IFN-γ plays a significant role in the control and resolution of measles infection (Finke, et al, *J. Virol.* 69:5469-5474, 1995; Schneider-Schaulies, et al., *Virology* 195:219-228, 1993). IL-4 cytokine was studied as a signature marker of Th2-type immune responses and because the production of IL-4 by CD4+ T lymphocytes is essential for the development of measles-specific antibody production (Li, et al., *Vaccine* 19:4896-4900, 2001; Ward and Griffin, *Clin. Immunol. Immunopathol.* 67:171-177, 1993). We demonstrated that PBMC required only one round of peptide stimulation in vitro to produce effector cytokines such as IFN-γ and IL-4, suggesting that these MV-P and MV-N peptides were recognized by HLA class II-restricted memory T cells in healthy subjects previously immunized against measles. We detected IFN-γ and IL-4 responses to single MV-P and MV-N epitopes in PBMC samples. These recall cytokine responses elicited by MV and measles-derived peptides were antigen specific because only very low levels of cytokine production were detected in the absence of MV or peptide stimulation. Furthermore, these responses were induced in a setting of subjects previously vaccinated against measles because MV- or measles peptide-specific IFN-γ and IL-4 responses theoretically could not be generated from naïve subjects. In addition, it is important to realize that these two peptides, presented in vivo, failed to induce recall cytokine immune responses in some of the human subjects. Because these peptides were eluted from a HLA-DRB1*03 "nonresponder" allele, it would be surprising if a large percentage of HLA discordant subjects could respond to these peptides, especially since these peptides are not universal degenerate peptides which bind to all HLA-DR molecules.

The ability of individual peptides to bind to multiple HLA-DRB1 alleles and be presented to DR-restricted T cells is defined as promiscuous T cell recognition and has been previously described for some antigenic epitopes such as influenza hemagglutinin-derived peptide, tetanus toxoid and T cell epitopes from malaria *Plasmodium falciparum* (Chicz, et al., *J. Exp. Med.* 178:27-47, 1993; Doolan, et al., *J. Immunol.* 165:1123-1137, 2000; Panina-Bordignon, et al., *Eur. J. Immunol.* 79:2237-2242, 1989; Roche and Cresswell, *J. Immunol.* 144:1849-1856, 1990; Rothbard, et al, *Cell* 52:515-523, 1988; Sinigaglia, et al., *Nature* 336(6201):778-780, 1988). A promiscuous T cell epitope from the measles virus F protein (residues 288 to 302) that binds to several isotypic and allotypic forms of human HLA class II molecules has also been described (Lairmore, et al., J. Virol. 69:6077-6089, 1995; Partidos and Steward, J. Gen. Virol. 71:2099-2105, 1990).

As polymorphic residues of HLA-DRB1 molecules are distributed within the peptide-binding grooves, different DR molecules are able to bind peptides with different structural motifs, and this contributes to the HLA-linked polymorphism of immune responses or susceptibility to immunity-related diseases (Matsushita, et al., J. Exp. Med. 180:873-883, 1994). In the current study we tested naturally processed and presented MV peptides bound to HLA-DRB1*0301, which is one of the HLA molecules associated with low levels of measles antibody following immunization (Poland, et al., Vaccine 20:430-438, 2001). HLA-DRB1*03 molecules are not highly polymorphic and have been considered minor antigens (Obeid, et al, J. Virol. 69:1420-1428, 1995). The HLA-DRB1*03 primary amino acid sequence motif is characterized by four conserved anchor positions (1, 4, 6, 9) similar to those found for DRB1*01 and DRB1*05 motifs (Malcherek, et al., Int. Immunol. 5:1229-1237, 1993). Sidney, et al. (Sidney, et al., J. Immunol. 149(8):2634-2640, 1992) report that DRB1*01, DRB1*03 and DRB1*04 molecules recognize a structural motif for binding peptides distinct from the one recognized by most HLA-DRB1 alleles, however, relatively few immune responses in humans have been demonstrated to be HLA allele specific (Hammer, et al., Cell 74:197-203, 1993; Matsushita, et al, J. Exp. Med. 180:873-883, 1994).

This study demonstrated that a MV-N epitope is recognized by memory T cells in association with several class II DRB1 molecules. For the MV-P peptide, the allele with the strongest association with IFN-γ and IL-4 responses was DRB1*0301. Further peptide binding studies with purified human HLA-DRB1 molecules containing specific HLA-DRB1 binding motifs could fully address the question of whether MV-P is restricted via HLA-DRB1*0301. Because HLA-DRB1*03 alleles are linked to DRB1*01 alleles, this linkage disequilibrium with DRB1*01 could contribute to findings associated with *0301 (Hader, et al., J. Infect. Dis. 185:1729-1735, 2002). For the MV-N peptide, the alleles providing strongest evidence of an association with IFN-γ and IL-4 secretion were DRB1*1501 and DRB1*1103/*1303, respectively. These results might imply that naturally processed, single measles peptides are capable of inducing cytokine T lymphocyte responses in individuals of several class II HLA-DRB1 types and that an active T cell repertoire exists for these two epitopes.

A striking finding was a significant association of the DRB1*0301 allele with measles and MV-P peptide specific IFN-γ and IL-4 responses. We previously reported the role of class II HLA-DRB1*03 molecules in measles vaccine virus antibody response (Ovsyannikova, I. G., Sohni, Y., Jacobson, R. M., Vierkant, R., Schaid, D., Pankratz, S. V., Jacobsen, S. J., and Poland, G. A. The role of class II HLA-DRB1*03 molecules in measles vaccine virus (MVV) nonresponse. Keystone Symposia, Keystone, Colorado Abstr. 145, 2000). Thus, the present results confirm this observation regarding the important role of class II HLA-DRB1*03 antigens in measles-induced immune responses.

Our findings are in concordance with other reports demonstrating that HLA-DRB1 promiscuous T cell epitopes from pathogens could be restricted by multiple HLA class II alleles. For example, Hickman, et al. (Hickman, et al., Virology 235:386-397, 1997) demonstrated that synthetic N peptides (20mers), based on the predicted amino acid sequences of the Edmonston strain of measles, were recognized by approximately 70% of all tested donors. We confirmed this observation, supporting this earlier report that measles N peptides may be broadly recognized within an HLA-DRB1 diverse population (Hickman, et al., supra, 1997). Importantly, the identified naturally processed and presented MV-N peptide (residues 372-385) contains the amino acid sequence of published measles predicted N peptide (residues 367-386) that induced significant proliferative responses (stimulation indices≧3) in approximately 67% of vaccinated and 100% of naturally infected donors (Hickman, et al., supra, 1997).

In this study, we used live attenuated plaque-purified MV (Edmonston-Enders vaccine strain) cultured in Vero cells to infect HLA-DRB1*0301 homozygous EBV-B cells and to isolate the HLA-bound peptides. Measles-derived N and P peptide sequences were obtained from the protein sequences listed in a public NCBI nr database. Because the sequences of the Edmonston-derived vaccine strains are quite similar to the sequences of a low-passage seed of the wild-type Edmonston virus (Rota, et al., Virus Res. 31:317-330, 1994), it is likely that this degree of conservation between MV strains plays a positive role in the peptide identification. Measles P, N and F proteins were found to be antigenically more stable between strains than H and M proteins (Sheshberadaran, et al., Virology 128:341-353, 1983) and the phosphoprotein-binding sites are conserved between vaccine and wild-type MV (Bankamp, et al, J. Gen. Virol. 80:1617-1625, 1999). Rota, et al. (Rota, et al., supra, 1994) demonstrated that sequences of H, F and N coding genes were nearly identical to the H, F and N sequences of wild-type Edmonston virus, however, genetic variations in the H and F genes were described within circulating wild-type MV relative to the vaccine strain Moraten (Rota, et al., Virology 188:135-142, 1992). This suggests that the class II peptides identified herein may be potentially incorporated in a vaccine designed to protect humans against wild-type MV infection.

There are several limitations to our study. First, the sample size is only moderate. Despite this, the results of our study demonstrate that MV-derived peptides were recognized in association with different HLA-DRB1 molecules and elicited cytokine responses in vitro in individuals expressing DRB1-encoded molecules. Second, the lack of racial diversity (93% of our subjects were Caucasian) does not allow us to project population coverage by these MV epitopes. Finally, further studies with larger population sample sizes to determine the kinetics of HLA binding capacity and HLA restriction of measles-derived peptides may help assess the role of HLA class II pathogen-derived peptides in antigen-directed immune responses.

In summary, we have described the direct elution and identification of a naturally processed peptide having SEQ ID NO:1 from the MV nucleoprotein through the HLA class II pathway. This peptide (MV-N) was identified by 2D-LC-MS/MS using gas phase fractionation, which enhances our ability to acquire MS/MS spectra of low abundance peptides. These data, in conjunction with a previous report describing the identification of the peptide having SEQ ID NO:2 (MV-P) from the MV phosphoprotein, provides direct evidence that measles processed proteins can be presented by class II HLA-DRB1 molecules. We have further established that both peptides are immunogenic, as assessed by their ability to stimulate IFN-γ and IL-4 cytokine responses from the PBMC of immune individuals. We observed that these peptides were recognized by HLA class II-restricted memory T cells in healthy subjects immunized against measles in association with different HLA-DRB1 alleles. These results are promising and provide experimental support for the development of novel immunization strategies using peptide-based vaccines against measles and other viral infections.

TABLE 1

Measles virus- and measles peptide-specific cytokine responses[a] in healthy subjects.

| | IFN-γ | | | | IL-4 | | | |
|---|---|---|---|---|---|---|---|---|
| Antigen | % Response (>20 pg/mL) | Median level (pg/mL) | Interquartile range of response (pg/mL) | P-value[b] | % Response (>10 pg/mL) | Median level (pg/mL) | Interquartile range of response (pg/mL) | P-value[b] |
| Measles virus | 65.8 | 57.0 | 11.3, 214.7 | <.0001 | 50.9 | 10.7 | 3.9, 24.9 | <.0001 |
| MV-P peptide | 55.9 | 28.0 | 1.9, 106.1 | <.0001 | 19.2 | −0.4 | −6.5, 6.3 | 0.8701 |
| MV-N peptide | 15.3 | 1.9 | −6.6, 12.4 | .0039 | 23.1 | 2.8 | −2.8, 9.4 | <.0001 |

[a]Stimulated cells minus unstimulated cells.
[b]Wilcoxon signed rank test, testing whether cytokine responses differ from zero.

TABLE 2

Phenotypic frequency of the 281 study subjects[a].
Phenotype frequency (%)

| HLA-DRB1 locus | Allele | N of alleles | Percent, allele | Percent, HLA-DRB1 locus |
|---|---|---|---|---|
| DR1 | DRB1*0101 | 46 | 8.19 | 9.08 |
| | DRB1*0102 | 5 | 0.89 | |
| DR103 | DRB1*0103 | 6 | 1.07 | 1.07 |
| DR2 | DRB1*1501 | 75 | 13.35 | 14.25 |
| | DRB1*1502 | 2 | 0.36 | |
| | DRB1*1503 | 2 | 0.36 | |
| | DRB1*1601 | 1 | 0.18 | |
| DR3 | DRB1*0301 | 59 | 10.50 | 11.93 |
| | DRB1*03011 | 7 | 1.25 | |
| | DRB1*0302 | 1 | 0.18 | |
| DR4 | DRB1*0401 | 49 | 8.72 | 17.09 |
| | DRB1*0402 | 7 | 1.25 | |
| | DRB1*0403 | 4 | 0.71 | |
| | DRB1*0404 | 25 | 4.45 | |
| | DRB1*0405 | 4 | 0.71 | |
| | DRB1*0407 | 5 | 0.89 | |
| | DRB1*0408 | 2 | 0.36 | |
| DR5 | DRB1*1101 | 24 | 4.27 | 12.11 |
| | DRB1*1102 | 1 | 0.18 | |
| | DRB1*1103 | 5 | 0.89 | |
| | DRB1*1104 | 16 | 2.85 | |
| | DRB1*1106 | 1 | 0.18 | |
| | DRB1*1111 | 1 | 0.18 | |
| | DRB1*1121 | 1 | 0.18 | |
| | DRB1*1201 | 15 | 2.67 | |
| | DRB1*1202 | 4 | 0.71 | |
| DR6 | DRB1*1301 | 43 | 7.65 | 17.99 |
| | DRB1*1302 | 29 | 5.16 | |
| | DRB1*1303 | 7 | 1.25 | |
| | DRB1*1305 | 2 | 0.36 | |
| | DRB1*1310 | 1 | 0.18 | |
| | DRB1*1315 | 1 | 0.18 | |
| | DRB1*1401 | 15 | 2.67 | |
| | DRB1*1406 | 1 | 0.18 | |
| | DRB1*1410 | 1 | 0.18 | |
| | DRB1*1424 | 1 | 0.18 | |
| DR7 | DRB1*0701 | 56 | 9.96 | 9.96 |
| DR8 | DRB1*0801 | 17 | 3.02 | 3.74 |
| | DRB1*0802 | 1 | 0.18 | |
| | DRB1*0803 | 2 | 0.36 | |
| | DRB1*0804 | 1 | 0.18 | |
| DR9 | DRB1*0901 | 10 | 1.78 | 1.78 |
| DR10 | DRB1*1001 | 5 | 0.89 | 0.89 |
| DR12 | DRB1*1208 | 1 | 0.18 | 0.18 |

[a]Each subject represented twice-once for each allele.

TABLE 3

HLA-DRB1 allelic associations with measles virus-specific cytokine[a] responses.

| | | IFN-γ | | | IL-4 | | |
|---|---|---|---|---|---|---|---|
| HLA-DRB1 allele | N of alleles | Median secretion value (Q1, Q3) pg/mL | P-value[b,c] | Global P-value[b] | Median secretion value (Q1, Q3) pg/mL | P-value[b,c] | Global P-value[b] |
| | | | | 0.005 | | | 0.21 |
| DR1 | 51 | | 0.51 | | | 0.21 | |
| *0101 | 46 | 72.6 (15.7, 192.7) | 0.93 | | 15.8 (6.6, 25.3) | 0.41 | |
| *0102 | 5 | 281.1 (66.9, 565.7) | 0.08 | | 18.9 (17.7, 33.1) | 0.16 | |
| DR103 | 6 | | 0.38 | | | 0.03 | |
| *0103 | 6 | 17.5 (−1.3, 124.3) | 0.38 | | −0.7 (−4.9, 7.3) | 0.03 | |
| DR2 | 80 | | 0.003 | | | 0.69 | |
| *1501 | 75 | 120.8 (36.9, 325.8) | 0.004 | | 15.5 (4.3, 25.3) | 0.47 | |
| DR3 | 67 | | 0.02 | | | 0.80 | |
| *0301 | 59 | 18.4 (3.2, 110.6) | 0.02 | | 8.6 (5.4, 24.5) | 0.96 | |
| *03011 | 7 | 18.6 (8.9, 25.9) | 0.42 | | 7.0 (−3.4, 14.2) | 0.46 | |
| DR4 | 96 | | 0.49 | | | 0.30 | |
| *0401 | 49 | 44.0 (6.6, 118.0) | 0.13 | | 9.0 (2.8, 20.0) | 0.41 | |
| *0402 | 7 | 58.4, −19.2, 187.2) | 0.60 | | 8.7 (4.6, 83.1) | 0.61 | |

TABLE 3-continued

HLA-DRB1 allelic associations with measles virus-specific cytokine[a] responses.

| | | IFN-γ | | | IL-4 | | |
|---|---|---|---|---|---|---|---|
| HLA-DRB1 allele | N of alleles | Median secretion value (Q1, Q3) pg/mL | P-value[b,c] | Global P-value[b] | Median secretion value (Q1, Q3) pg/mL | P-value[b,c] | Global P-value[b] |
| *0404 | 25 | 123.5 (18.6, 343.1) | 0.07 | | 11.1 (4.7, 21.7) | 0.76 | |
| *0407 | 5 | 188.3 (66.8, 565.7) | 0.32 | | 40.7 (8.4, 68.4) | 0.30 | |
| DR5 | 68 | | | 0.14 | | | 0.21 |
| *1101 | 24 | 88.4 (12.6, 333.1) | 0.54 | | 13.4 (6.3, 42.7) | 0.16 | |
| *1103 | 5 | 188.2 (114.8, 347.4) | 0.09 | | 21.4 (5.9, 22.6) | 0.78 | |
| *1104 | 16 | 111.7 (31.2, 637.6) | 0.11 | | 17.2 (8.4, 26.6) | 0.28 | |
| *1201 | 15 | 44.1 (8.4, 119.1) | 0.89 | | 13.6 (4.7, 24.3) | 0.56 | |
| DR6 | 101 | | | 0.44 | | | 0.46 |
| *1301 | 43 | 111.5 (12.6, 306.7) | 0.31 | | 14.2 (4.5, 30.5) | 0.25 | |
| *1302 | 29 | 45.1 (3.6, 301.4) | 0.50 | | 8.1 (1.5, 18.5) | 0.26 | |
| *1303 | 7 | 129.6 (13.6, 485.3) | 0.36 | | 1.8 (−0.4, 7.3) | 0.04 | |
| *1401 | 15 | 67.1 (36.9, 172.6) | 0.71 | | 9.6 (0.6, 26.9) | 0.56 | |
| DR7 | 56 | | | 0.01 | | | 0.02 |
| *0701 | 56 | 33.5 (2.8, 113.0) | 0.01 | | 5.6 (0.9, 22.5) | 0.02 | |
| DR8 | 21 | | | 0.04 | | | 0.46 |
| *0801 | 17 | 10.2 (2.5, 41.1) | 0.05 | | 11.8 (4.4, 33.5) | 0.49 | |
| DR9 | 10 | | | 0.40 | | | 0.68 |
| *0901 | 10 | 26.8 (2.8, 53.4) | 0.40 | | 15.7 (0.6, 26.7) | 0.68 | |
| DR10 | 5 | | | 0.26 | | | 0.27 |
| *1001 | 5 | 47.3 (3.4, 96.6) | 0.26 | | 6.6 (0.1, 9.0) | 0.27 | |
| All other alleles[d] | 36 | 53.4 (29.8, 233.9) | 0.36 | | 11.1 (−0.3, 41.0) | 0.76 | |
| Overall | 281 | 57.0 | | | 10.7 | | |

Q1, Q3 represent the first and third quartiles, respectively.
[a]Mean value of antigen stimulated cells minus mean value of control cells.
[b]Linear regression analysis, accounting for the design variable age. Genotypes were modeled as ordinal variables with values ranging from 0 to 2, reflecting the number of copies possessed by an individual. Due to data skewness, all secretion values were rank-transformed.
[c]Comparing genotype of interest to all other genotypes combined.
[d]Other includes the following DRB1 alleles: *0302 (n = 1), *0403 (n = 4), *0405 (n = 4), *0408 (n = 2), *0802 (n = 1), *0803 (n = 2), *0804 (n = 1), *1102 (n = 1), *1106 (n = 1), *1111 (n = 1), *1121 (n = 1), *1202 (n = 4), *1208 (n = 1), *1305 (n = 2), *1310 (n = 1), *1315 (n = 1), *1406 (n = 1), *1410 (n = 1), *1424 (n = 1), *1502 (n = 2), *1503 (n = 2), and *1601 (n = 1).

TABLE 4

HLA-DRB1 allelic associations with naturally processed measles virus-derived P peptide-specific cytokine[a] responses.

| | | IFN-γ | | | IL-4 | | |
|---|---|---|---|---|---|---|---|
| HLA-DRB1 allele | N of alleles | Median secretion value (Q1, Q3) pg/mL | P-value[b,c] | Global P-value[b] | Median secretion value (Q1, Q3) pg/mL | P-value[b,c] | Global P-value[b] |
| | | | | 0.20 | | | 0.746 |
| DR1 | 51 | | 0.15 | | | 0.45 | |
| *0101 | 46 | 51.2 (6.6, 132.2) | 0.08 | | 1.1 (−4.7, 7.5) | 0.61 | |
| *0102 | 5 | 17.6 (6.4, 25.5) | 0.43 | | 5.6 (2.8, 10.0) | 0.42 | |
| DR103 | 6 | | 0.07 | | | 0.37 | |
| *0103 | 6 | 116.2 (63.2, 659.6) | 0.07 | | −1.5 (−3.9, 0.3) | 0.37 | |
| DR2 | 80 | | 0.99 | | | 0.52 | |
| *1501 | 75 | 32.8 (−3.0, 131.6) | 0.97 | | −0.7 (−9.0, 6.0) | 0.70 | |
| DR3 | 67 | | 0.09 | | | 0.05 | |
| *0301 | 59 | 40.8 (11.9, 121.2) | 0.02 | | 3.5 (−3.6, 11.3) | 0.03 | |
| *03011 | 7 | 18.7 (1.8, 46.2) | 0.33 | | 0.2 (−1.8, 2.6) | 0.96 | |
| DR4 | 96 | | 0.56 | | | 0.45 | |
| *0401 | 49 | 33.5 (2.7, 75.7) | 0.50 | | 0.9 (−4.8, 9.5) | 0.51 | |
| *0402 | 7 | 0.1 (−6.7, 107.8) | 0.48 | | 3.8 (−2.5, 26.1) | 0.20 | |
| *0404 | 25 | 52.2 (14.6, 128.1) | 0.06 | | 0.3 (−6.4, 6.4) | 0.99 | |
| *0407 | 5 | 8.6 (6.0, 16.2) | 0.32 | | −2.1 (−6.3, 10.0) | 0.92 | |
| DR5 | 68 | | 0.12 | | | 0.40 | |
| *1101 | 24 | 48.5 (−3.1, 111.4) | 0.94 | | −3.7 (−9.6, 7.5) | 0.29 | |
| *1103 | 5 | 65.3 (37.3, 95.7) | 0.50 | | −3.5 (−4.6, 9.3) | 0.99 | |
| *1104 | 16 | 15.4 (−3.8, 88.3) | 0.28 | | −1.3 (−5.7, 1.7) | 0.43 | |
| *1201 | 15 | 14.6 (−11.2, 65.0) | 0.21 | | −0.4 (−3.4, 3.5) | 0.69 | |
| DR6 | 101 | | 0.48 | | | 0.06 | |
| *1301 | 43 | 27.4 (−10.0, 75.7) | 0.10 | | −3.0 (−8.7, 2.7) | 0.15 | |
| *1302 | 29 | 14.2 (−0.7, 142.1) | 0.89 | | 1.2 (−7.4, 9.6) | 0.71 | |

TABLE 4-continued

HLA-DRB1 allelic associations with naturally processed measles virus-derived P peptide-specific cytokine[a] responses.

| HLA-DRB1 allele | N of alleles | IFN-γ Median secretion value (Q1, Q3) pg/mL | P-value[b,c] | Global P-value[b] | IL-4 Median secretion value (Q1, Q3) pg/mL | P-value[b,c] | Global P-value[b] |
|---|---|---|---|---|---|---|---|
| *1303 | 7 | 63.9 (−11.7, 290.1) | 0.79 | | −4.2 (−18.4, 0.2) | 0.09 | |
| *1401 | 15 | 22.5 (11.5, 125.0) | 0.59 | | −0.8 (−7.2, 6.0) | 0.75 | |
| DR7 | 56 | | 0.21 | | | 0.53 | |
| *0701 | 56 | 18.6 (−3.1, 85.1) | 0.21 | | −0.6 (−7.2, 12.4) | 0.53 | |
| DR8 | 21 | | 0.45 | | | 0.74 | |
| *0801 | 17 | 27.2 (3.3, 32.4) | 0.25 | | −1.4 (−8.0, 6.1) | 0.69 | |
| DR9 | 10 | | 0.86 | | | 0.77 | |
| *0901 | 10 | 19.9 (4.6, 121.8) | 0.86 | | −0.9 (−4.1, 16.9) | 0.77 | |
| DR10 | 5 | | 0.50 | | | 0.85 | |
| *1001 | 5 | 46.9 (−9.9, 54.4) | 0.50 | | 0.9 (−0.9, 2.8) | 0.85 | |
| All other alleles[d] | 36 | 26.7 (9.9, 98.2) | 0.59 | | −1.3 (−7.9, 1.5) | 0.17 | |
| Overall | 281 | 28.0 | | | −0.4 | | |

Q1, Q3 represent the first and third quartiles, respectively.
[a]Mean value of antigen stimulated cells minus mean value of control cells.
[b]Linear regression analysis, accounting for the design variable age. Genotypes modeled as a 0/1/2 ordinal variables, reflecting the number of opies possessed by an individual. Due to data skewness, all secretion values were rank-transformed.
[c]Comparing genotype of interest to all other genotypes combined.
[d]Other includes the following DRB1 alleles: *0302 (n = 1), *0403 (n = 4), *0405 (n = 4), *0408 (n = 2), *0802 (n = 1), *0803 (n = 2), *0804 (n = 1), *1102 (n = 1), *1106 (n = 1), *1111 (n = 1), *1121 (n = 1), *1202 (n = 4), *1208 (n = 1), *1305 (n = 2), *1310 (n = 1), *1315 (n = 1), *1406 (n = 1), *1410 (n = 1), *1424 (n = 1), *1502 (n = 2), *1503 (n = 2), and *1601(n = 1).

TABLE 5

HLA-DRB1 allelic associations with naturally processed measles virus-derived N peptide-specific cytokine[a] responses.

| HLA-DRB1 allele | N of alleles | IFN-γ Median secretion value (Q1, Q3) pg/mL | P-value[b,c] | Global P-value[b] | IL-4 Median secretion value (Q1, Q3) pg/mL | P-value[b,c] | Global P-value[b] |
|---|---|---|---|---|---|---|---|
| | | | | 0.22 | | | 0.37 |
| DR1 | 51 | | 0.87 | | | 0.94 | |
| *0101 | 46 | −1.8 (−6.1, 11.6) | 0.67 | | 4.3 (−1.6, 8.9) | 0.94 | |
| *0102 | 5 | 7.6 (1.8, 8.4) | 0.45 | | 4.6 (−0.7, 4.6) | 0.66 | |
| DR103 | 6 | | 0.97 | | | 0.36 | |
| *0103 | 6 | 2.4 (−12.6, 33.6) | 0.97 | | 1.3 (−1.7, 5.5) | 0.36 | |
| DR2 | 80 | | 0.36 | | | 0.59 | |
| *1501 | 75 | 4.1 (−5.1, 18.8) | 0.04 | | 3.2 (−3.5, 11.1) | 0.84 | |
| DR3 | 67 | | 0.37 | | | 0.36 | |
| *0301 | 59 | 1.8 (−5.8, 6.2) | 0.20 | | 2.8 (−2.8, 14.4) | 0.26 | |
| *03011 | 7 | 9.1 (4.5, 13.0) | 0.45 | | 1.7 (−1.0, 2.2) | 0.71 | |
| DR4 | 96 | | 0.76 | | | 0.89 | |
| *0401 | 49 | −0.7 (−9.1, 9.5) | 0.12 | | 4.3 (0.4, 9.7) | 0.15 | |
| *0402 | 7 | 10.6 (−2.9, 46.6) | 0.27 | | −1.0 (−4.6, 7.0) | 0.54 | |
| *0404 | 25 | 2.8 (−8.2, 9.7) | 0.81 | | 0.0 (−4.2, 6.8) | 0.48 | |
| *0407 | 5 | 8.4 (8.2, 12.8) | 0.15 | | 4.6 (4.0, 13.7) | 0.50 | |
| DR5 | 68 | | 0.13 | | | 0.03 | |
| *1101 | 24 | −4.4 (−11.0, 16.2) | 0.31 | | 4.4 (−0.1, 11.9) | 0.51 | |
| *1103 | 5 | 3.0 (−3.8, 6.7) | 0.87 | | 15.5 (8.8, 17.5) | 0.01 | |
| *1104 | 16 | 3.1 (−5.9, 25.6) | 0.68 | | 4.4 (0.1, 11.2) | 0.43 | |
| *1201 | 15 | −4.5 (−11.1, 7.5) | 0.07 | | 5.4 (1.5, 15.9) | 0.20 | |
| DR6 | 101 | | 0.56 | | | 0.20 | |
| *1301 | 43 | 2.2 (−5.3, 13.0) | 0.55 | | 3.6 (−3.2, 6.7) | 0.71 | |
| *1302 | 29 | −1.9 (−10.5, 13.0) | 0.62 | | 2.2 (−3.6, 6.4) | 0.81 | |
| *1303 | 7 | 13.1 (−9.4, 37.5) | 0.19 | | −12.9 (−19.2, 1.8) | 0.01 | |
| *1401 | 15 | 0.2 (−10.1, 10.2) | 0.47 | | 3.7 (−5.6, 12.7) | 0.95 | |
| DR7 | 56 | | 0.23 | | | 0.71 | |
| *0701 | 56 | −1.1 (−7.8, 10.3) | 0.23 | | 1.7 (−3.0, 10.2) | 0.71 | |
| DR8 | 21 | | 0.62 | | | 0.84 | |
| *0801 | 17 | 4.1 (−7.9, 9.5) | 0.89 | | 1.7 (0.1, 8.2) | 0.80 | |
| DR9 | 10 | | 0.43 | | | 0.29 | |
| *0901 | 10 | 3.1 (0.2, 14.8) | 0.43 | | −1.6 (−7.0, 17.6) | 0.29 | |
| DR10 | 5 | | 0.14 | | | 0.90 | |

TABLE 5-continued

HLA-DRB1 allelic associations with naturally processed measles virus-derived N peptide-specific cytokine[a] responses.

| | | IFN-γ | | | IL-4 | | |
|---|---|---|---|---|---|---|---|
| HLA-DRB1 allele | N of alleles | Median secretion value (Q1, Q3) pg/mL | P-value[b,c] | Global P-value[b] | Median secretion value (Q1, Q3) pg/mL | P-value[b,c] | Global P-value[b] |
| *1001 | 5 | −1.8 (−7.1, −1.7) | 0.14 | | 2.1 (0.6, 5.7) | 0.90 | |
| All other alleles[d] | 36 | 4.1 (0.2, 18.6) | 0.02 | | −0.5 (−6.0, 8.4) | 0.15 | |
| Overall | 281 | 1.9 | | | 2.8 | | |

Q1 and Q3 represent the first and third quartiles, respectively.
[a]Mean value of antigen stimulated cells minus mean value of control cells.
[b]Linear regression analysis, accounting for the design variable age. Genotypes modeled as a 0/1/2 ordinal variables, reflecting the number of copies possessed by an individual. Due to data skewness, all secretion values were rank-transformed.
[c]Comparing genotype of interest to all other genotypes combined.
[d]Other includes the following DRB1 alleles: *0302 (n = 1), *0403 (n = 4), *0405 (n = 4), *0408 (n = 2), *0802 (n = 1), *0803 (n = 2), *0804 (n = 1), *1102 (n = 1), *1106 (n = 1), *1111 (n = 1), *1121 (n = 1), *1202 (n = 4), *1208 (n = 1), *1305 (n = 2), *1310 (n = 1), *1315 (n = 1), *1406 (n = 1), *1410 (n = 1), *1424 (n = 1), *1502 (n = 2), *1503 (n = 2), and *1601 (n = 1).

Example 3

Influence of HLA-DRB1 Alleles on Lymphoproliferative Responses to a Naturally Processed and Presented Measles Virus Phosphoprotein in Measles Immunized Individuals Human leukocyte antigen (HLA) genes are important determinants of genetic susceptibility to viral infections because of their antigen presenting function. In particular, the class II HLA molecules play a significant role in stimulating an immune response to measles virus (MV) by binding foreign peptides of extracellular origin and presenting them to CD4+ T lymphocytes, resulting in cytokine production and T cell help for antibody production (Carrington and O'Brien, Annu. Rev. Med. 54:535-551, 2003; Gans, et al., J. Immunol. 162:5569-5575, 1999). HLA-DRB1*0301 is a class II allele present in greater than 20% of the human population. Our previous work suggests that measles vaccine virus-induced humoral immune responses are associated with both HLA class I and class II genes (Poland, Vaccine 17:1719-1725, 1999; Jacobson, et al., Hum. Immunol. 64:103-109, 2003). Further, we have demonstrated that carriage of class II HLA-DRB1*03 alleles are associated with low levels of antibody after measles immunization (Poland, et al., Vaccine 20:430-438, 2001). Previously, we identified a naturally processed and presented peptide having SEQ ID NO:2, derived from a measles phosphoprotein (MV-P1, residues 179-197) and presented by class II HLA-DRB1*0301 molecules on measles-infected Epstein-Barr virus (EBV)-transformed B cells (Ovsyannikova, et al., Virology 312:495-506, 2003). In addition, we described a measles phosphoprotein peptide variant (MV-P2) obtained from a measles genome that differs only by one amino acid from the eluted MV-P1 peptide, a lysine (Lys or K) versus glutamic acid (Glu or E) in position 192. Although we did not observe this MV-P2 peptide in our analyses of naturally processed peptides expressed by HLA-DRB1*0301, we synthesized this peptide for further study.

It is becoming more apparent that virus-specific CD4+ T cells play an important role in measles immune responses (van Binnendijk, et al, J. Immunol. 144:2394-2399, 1990; Griffin, et al, J. Infect. Dis. 168:275-281, 1993; van Els and Nanan, Viral Immunol. 15:435-450, 2002). Only a few naturally processed HLA class I associated antigenic sites or cytotoxic T cells (CTL) epitopes on MV hemagglutinin (H), fusion (F) glycoprotein, matrix (M) and non-structural C proteins have been identified at the peptide level (Herberts, et al., J. Gen. Virol. 82:2131-2142, 2001; van Els, et al., Eur. J. Immunol. 30:1172-1181, 2000). These measles class I epitopes may have important implications for the induction of antiviral T cell immunity (Herberts, et al., Mol. Immunol. 39:567-575, 2003). However, relatively little is known about CD4+ T cell responses to naturally processed MV peptides presented by HLA class II molecules.

Cell-mediated immunity (CMI) is of crucial importance to measles immunity and can be assessed by measuring CTL, lymphoproliferative and cytokine responses (Ward, et al., J. Infect. Dis. 172:1591-1595, 1995). Memory T lymphocyte proliferative responses to measles antigens have been reported in 100% of individuals who had natural measles infection and in approximately 60% to 90% of immunized children (Gallagher, et al, Am. J. Dis. Child. 135:48-51, 1981; Gans, et al., JAMA 280:527-532, 1998; Pabst, et al., Vaccine 17:1910-1918, 1999). Although we have reported associations between low antibody levels and specific HLA alleles, associations between cellular (proliferative) immune responses elicited by MV and by naturally processed measles-derived peptides have not yet been identified.

The objective of the present study was to investigate the T cell responses of previously immunized individuals to MV, to the naturally processed HLA class II MV-P1 epitope and to the MV-P2 peptide variant. Furthermore, we sought to determine if associations exist between measles virus, MV-P1 and MV-P2 specific lymphoproliferative responses and alleles of the HLA-DRB1 locus for subjects who had been vaccinated against measles.

Materials and Methods

Study Subjects

Details of subject identification and recruitment have been previously published (Ovsyannikova, et al., J. Virol. In Press, 2003). Briefly, study participants were enrolled as part of a larger stratified random sample study to assess associations between HLA genes and immune response to measles-mumps-rubella-II (MMR-II) vaccine in healthy, school-age children and young adults (ages 12 to 18 years). To evaluate the cellular responses to measles peptides, 131 subjects were used. In addition, a random subset of 43 individuals was tested for reactivity to a control measles fusion (F) peptide. All enrolled subjects had been previously immunized with two doses of MMR-II vaccine (Merck Research, West Point, Pa.) containing the attenuated Edmonston strain of MV. All but four of these participants were Caucasian and all subjects resided in a geographic area where no wild-type MV had circulated in the community during the subjects' lifetimes. The Institutional Review Board (IRB) of the Mayo Clinic granted approval for the study, and peripheral blood samples were drawn after informed consent was obtained from each subject. We also obtained written, informed consent from parents or guardians of all the subjects at the time of enrollment in the study.

HLA Typing

Genomic DNA was extracted from blood samples by conventional techniques using the PYREGENE extraction kit (Gentra Systems Inc., Minneapolis, Minn.). DNA was used for class II HLA-DRB1 allele typing using a high resolution DRB96 SSP (sequence-specific primer) Unitray typing kit with the entire locus on a single tray (Pel-Freez Clinical Systems, LLC, Brown Deer, Wis.) (Büchler, T., et al., *Hum. Immunol.* 63:139-142,2002). Locus-specific primers were used to amplify the HLA-DRB1 locus and PCR products were separated on 2% agarose gel and stained with ethidium bromide. Any ambiguities were resolved using the ABI DRB1 sequencing kit (Applied Biosystems, Foster City, Calif.). All PCR amplifications were carried out in a Gene-Amp PCR system 9600 (Perkin ElmerCetus Instruments). All reactions were run with negative controls and every 50$^{th}$ PCR reaction repeated for quality control.

Measles Vaccine Virus and Synthetic Peptides

Many of the details of peptide identification and peptide sequencing methodology have been previously published (Ovsyannikova, I. G., et al., supra, 2003). Measles vaccine (Attenuvax, Merck Inc., West Point, Pa.) containing 1,000 median tissue culture infective doses (TCID$_{50}$) of the Edmonston strain of MV was used for lymphocyte proliferation assays. Measles peptides were synthesized by the Mayo Protein Core Facility (Rochester, Minn.) using N-(9-fluorenyl) methoxycarbonyl protection chemistry and carbodiimide/N-hydroxybenzotriazole activation on a MPS 396 Multiple Peptide Synthesizer (Advanced Chemtech, Louisville, Ky.). The following three peptides were utilized: (1) measles-derived naturally processed 19 amino acid MV-P1 peptide of the measles P protein having SEQ ID NO: 2; (2) single amino acid substituted MV-P2 peptide having SEQ ID NO:14, differing only by one amino acid, a Lys (K) versus Glu (E) at position 192; and (3) randomly chosen 14 amino acid control peptide of the MV F protein having SEQ ID NO:15 (MV-F). The sequences for MV-P1 and MV-P2 are both identical as measles phosphoprotein in the NCBI nr database. MV-P1 and MV-P2 were each synthesized in order to confirm our identification of the naturally processed peptide from measles as MV-P1 and for use in understanding the role of amino acid sequence in inducing CD4+ T cell response.

Preparation of Peripheral Blood Leukocytes and T Cell Proliferation Assay

Details of our in vitro lymphoproliferation assay have been reported elsewhere (Ovsyannikova, et al., *Clin. Diag. Lab. Immunol.* 10:411-416, 2003). In brief, peripheral blood mononuclear cells (PBMC) were separated from heparinized blood by Ficoll-Hypaque (Sigma, St. Louis, Mo.) density gradient centrifugation and washed in RPMI 1640 medium (Celox Laboratories, Inc., St. Paul, Minn.) supplemented with 2 mM L-glutamine, 100 pg/ml streptomycin, 100 U/ml penicillin and 8% fetal calf serum (Life Technologies, Gaithersburg, Md.). Measles virus, MV-P1, MV-P2, and MV-F specific T cell responses were measures by proliferation of PBMC ($2\times10^5$) incubated in RPMI-1640 medium, supplemented with 5% autologous sera, with live attenuated MV (50 pfu/ml, positive control) or synthetic peptides (20 µg/ml) compared to unstimulated cell control wells. Phytohemagglutinin (PHA, 5 µpg/ml) was used to assess cell vitality. Only assays in which PBMC responded to PHA were accepted. T lymphocyte proliferation was measured after 4 days by [$^3$H]-tritiated thymidine uptake. Cells were then harvested onto glass fiber filters, using a 96-well harvesting system (Skatron Instruments, Norway). The amount of incorporated radioactivity was determined by a liquid scintillation counter (Packard Instrument Company, Boston, Mass.). We used six replicates of counts per minute (cpm) values for unstimulated cells, and three replicates each for T cells stimulated with peptides and live measles vaccine. For each subject, median cpm were calculated for unstimulated cells, as well as for cells stimulated with MV-P1, MV-P2, MV-F and measles. Results were then expressed as antigen-specific stimulation indices (SI), defined as the ratio of the median cpm of antigen-stimulated wells to the median cpm of unstimulated control wells. Stimulation indices of 2 or higher were considered to represent significant responses (van Binnendijk, et al., *J. Immunol.* 142:2847-2854,1989; Doolan, et al, *J. Immunol.* 165:1123-1137, 2000). SI>2 was arbitrarily selected prior to the study as an indication of the presence of reactive peptide specific memory T cells, and SI<2 as an indicator of the lack of memory T lymphocytes to measles-derived peptides (Pauksen, et al., *Bone Marrow Transplant* 20:317-323, 1997).

Statistical Analysis

Three outcomes were of primary interest: T cell proliferation (as measured by stimulation indices) induced separately by live MV, the MV-P1 peptide, and the MV-P2 peptide variant. Data were descriptively summarized using frequencies and percentages for all categorical variables, and medians and ranges for all continuous variables. To summarize the association of the three outcome variables with each other, we used Wilcoxon signed rank tests and Spearman rank correlation coefficients (on the original continuously-distributed variables), as well as cross-tabulations with sensitivity estimates (on the categorized stimulation index values). For the latter, measles-induced lymphoproliferation was used as the "gold standard."

Descriptive associations of the categorized stimulation indices with HLA-DR alleles were evaluated on an allelic level. Each person contributed two observations to this descriptive analysis—one for each allele. Alleles were grouped by DR status and summarized using frequencies and percents. Following the descriptive comparisons, associations were more formally evaluated using logistic regression analyses. In contrast to the descriptive comparisons, each subject contributed one observation to the regression analysis, based on his or her genotype. Regression variables were created for each allele and were coded as 0, 1, or 2, according to the number of copies of the allele that a subject carried. Thus, allelic odds ratios can be interpreted as the estimated increase in the odds of a high lymphoproliferative response for each additional copy of the allele of interest possessed by an individual. Rare alleles, defined as those with fewer than five occurrences among all subjects, were pooled into a category labeled "other." Global differences in stimulation indices among all alleles were first carried out via likelihood ratio tests by simultaneously including all but one of the allele variables in a multivariate logistic regression model. Following these global tests, we examined individual allele effects on stimulation indices. This series of tests were performed in the spirit of Fisher's Protected Least Significant Difference test; individual allele associations were not considered statistically significant in the absence of global significance. Each allele variable was included in a separate univariate logistic regression analysis, effectively comparing lymphoproliferation levels for the allele of interest against all other alleles combined. All global and univariate regression analyses included the design variable, age, as a covariate. All statistical tests were two-sided, and all analyses were carried out using the SAS software system (SAS Institute, Inc., Cary, N.C.).

Results

Cellular Responses of Vaccinated Individuals to Measles Virus and Measles Peptides Measles virus, MV-P1 peptide, MV-P2 peptide variant and the randomly chosen control MV-F peptide were tested for the ability to elicit in vitro recall lymphoproliferative responses in the subjects' PBMC after stimulation with MV (n=131), MV-P1 (n=131), MV-P2 (n=130) or MV-F (n=43). Stimulation of PBMC with measles resulted in significant MV-specific T cell responses. Measles virus stimulation indices (median SI 4.7, range 0.5-30.5) were higher than MV-P1 peptide (median 1.7, range 0.5-20.3, p-value Wilcoxon signed rank test<0.001) or single amino acid substituted MV-P2 peptide stimulation indices (median 1.2, range 0.4-16.2, p-value<0.001). Lymphoproliferative responses observed in the subjects' PBMC after stimulation with MV or with peptides revealed a positive correlation of MV-stimulated lymphoproliferative responses with MV-P1 peptide and MV-P2 peptide variant SIs (Spearman correlation coefficients=0.40 [p<0.001] and 0.25 [p<0.005], respectively) across all subjects, indicating comparative T cell responses for both forms of peptides.

As defined in Materials and Methods, a lymphoproliferative response was considered positive (stimulatory effect) if the SI was greater than 2.0. According to this criterion, 107 of the 131 (82%) subjects had MV stimulation indices greater than 2, indicating that MV contains multiple T helper lymphocyte epitopes and were recognized by PBMC derived from most of the individuals. Likewise, recall measles-derived MV-P1 lymphoproliferative responses were detected in 41% (53/131) of the subjects, suggesting MV-P1 recognition by memory T cells from previously immunized subjects. In contrast, the single amino acid substituted MV-P2 peptide was recognized in only 17% (22/130) of subjects. Among 107 subjects who responded to measles, 50 also responded to the MV-P1 peptide (sensitivity=47%) and 21 responded to the MV-P2 peptide variant (sensitivity=20%). Among the 52 subjects who responded to the MV-P1 peptide, 12 (23%) also responded to MV-P2-modified peptide, suggesting that MV-P1 and MV-P2 peptides possibly share common epitopes. The recall lymphoproliferative responses elicited by MV and peptides were antigen dose dependent, with optimal doses of peptides between 15 and 20 µg/2×10$^5$ PBMC. Finally, lymphoproliferative responses to the randomly chosen control MV-F peptide were quite low overall (median 1, range 0-3), although 5 (11%) of 43 subjects had SI>2. Age and sex of the study subjects did not affect antigen-specific lymphoproliferative responses (data not shown).

Occurrence of HLA-DRB1 Alleles in Study Subjects Previously Immunized against Measles HLA allelic frequencies in this study population were determined after molecular HLA typing. It was noted that the most prevalent alleles in this study population were HLA-DRB1*0301, *1501, *0401, and *0701 which were expressed in 14.5, 13.0, 11.5, and 11.5% individuals, respectively (Table 6).

Associations between HLA-DRB1 Alleles and Lymphoproliferative Responses to Measles Virus and Measles-Derived Peptides The association between class II HLA-DRB1 alleles and lymphocyte proliferation response to measles and measles peptides was examined using logistic regression analysis. Tables 7, 8 and 9 present the results of the logistic regression analysis of association with measles, MV-P1 and MV-P2-modified peptides and individual comparison of HLA-DRB1 alleles across the lymphocyte proliferation status. Global tests revealed no significant associations of HLA-DRB1 alleles with measles, MV-P1 and MV-P2 peptide variant specific lymphoproliferative responses. However, univariate analyses (Table 8) revealed a marginally significant (p=0.10) increase in the frequency of the *0301 allele among subjects who demonstrated low SI levels to MV (22.9%) compared to those with significant levels (SI>2) of MV specific lymphoproliferative response (12.6%, odds ratio (OR) 0.50; 95% confidence interval (CI) 0.22-1.15). In other DRB1 alleles, we found a significant (p=0.03) decrease in the frequency of the DRB1*0701 allele among subjects who responded (9.3%) compared to those with low (SI<2) MV specific lymphoproliferative responses (20.8%, OR 0.40; CI 0.18-0.92).

Measles-derived P1 peptide specific cellular responses and HLA-DRB1 alleles associations are summarized in Table 8. We found no associations between MV-P1 peptide with HLA-DRB1*0301 alleles. However, the frequency of *0701 alleles (OR, 0.40; CI 0.19-1.05, p=0.06) was also lower in subjects with significant MV-P1 specific lymphoproliferative responses (6.6%) compared to individuals with low SI levels to the MV-P1 peptide (14.7%). There were no other strong associations (except for the DRB1*0701 allele) between the MV-P1 specific lymphoproliferation and the frequency of other alleles; however, these associations should be interpreted with caution due to the small sample size and due to the absence of significant global tests. Examination of the lymphoproliferative responses to MV-P2 peptide variant indicated that none of the alleles of the HLA-DRB1 locus were associated with MV-P2 peptide variant T cell recognition (Table 9).

Of the 131 subjects, only four described themselves as non-Caucasian. Since allele distribution can differ drastically across race and ethnicity, we ran additional sensitivity analyses excluding these four subjects. Results were nearly identical to those presented in Tables 7-9 (not shown).

Discussion

There is a major interest in defining T and B cell epitopes recognized by CD4+ T cells involved in immune responses to measles immunization. Although CD4+ helper T cells recognizing different portions of the MV proteins have been reported, T cell responses to measles HLA class I and class II synthetic peptides corresponding to sequences of measles proteins are imprecise and not well characterized (Hickman, et al., *Virology* 235:386-397, 1997; van Binnendijk, et al., *J. Virol.* 67:2276-2284, 1993; Nanan, et al., *Clin. Exp. Immunol.* 102:40-45, 1995; Jaye, et al., *J. Virol.* 77:5014-5016, 2003). In addition, in measles patients and measles vaccine recipients only a few immunodominant T cell epitopes of MV antigens have been defined and mapped (Hickman, et al., supra, 1997; van Binnendijk, et al., supra, 1993). Therefore, additional studies are needed to identify other MV sequences containing important T cell epitopes. The purpose of this study was to analyze the lymphoproliferative responses of fresh PBMC of previously immunized HLA-DRB1*0301-positive and HLA-DRB1*0301-negative (HLA discordant) individuals to MV, to a naturally processed MV-derived peptide from the 70 kD phosphoprotein and to a measles peptide variant, and to determine if associations exist between MV and measles peptide specific lymphoproliferative responses and class II HLA-DRB1 alleles. Our evaluation of measles specific T lymphocyte proliferative responses to live attenuated measles vaccine virus showed that evidence of cellular immunity (SI>2) was detected in 82% of all study subjects. In contrast, CMI responses to single MV-P1 and MV-P2 epitopes were detected in 41% and 17% of the individuals, respectively. The finding that an identified MV-P1 peptide, eluted from a nonresponder associated HLA-DRB1*03 allele, was antigenic for recall lymphoproliferative responses in this study population is significant. This high frequency of proliferation is likely attributed to the fact that MV-P1 peptide was naturally processed and presented by DRB1*0301 alleles and is capable of inducing peptide specific recall immune response in the context of multiple HLA-DRB1 molecules.

Using PBMC from previously immunized subjects, we demonstrated that the MV-P2 peptide variant significantly affects in vitro T cell proliferation. Our data suggest that single amino acid changes at critical residues of measles-derived peptide could diminish T cell proliferation and activation. Possible explanations include the changes in the binding affinity of the 19-mer MV-P2 peptide variant to HLA-DRB1 class II molecules from subjects' PBMC and their ability to be recognized by specific T cell receptors (Doolan, et al., *J. Immunol.* 165:1123-1137, 2000; Southwood, et al., *J. Immunol.* 160:3363-3373, 1998). Wang, et al. (Wang, et al., *Hum. Immunol.* 64:662-673, 2003) recently reported that naturally occurring single amino acid variants of the Th1 epitope of hepatitis C virus (HCV) could modulate in vitro T cell responses by both escaping CD4+ T cell recognition and modulation of cytokine production. However, the role of altered binding affinity of HCV variant epitopes was not investigated in this study.

The MV-P2 peptide variant differed from the naturally processed and presented MV-P1 peptide only by one amino acid, a lysine (K) versus glutamic acid (E) at a position 192. Since these two amino acids vary significantly in the shape, charge, and overall size of their side chains, it is logical to presume that this amino acid variation may have significant effects on the overall antigenicity of the MV peptides (Lodish, et al., Protein structure and function, In Lodish, et al., (eds): Molecular Cell Biology, New York, Scientific American Books, W. H. Freeman and Company, 1995; St. Sauver, et al., *Hum. Immunol.* 64:696-707, 2003). Glutamic acid is a relatively small amino acid with an acidic carboxyl ($COO^-$) group side chain-very different from lysine, with its longer side chain containing a basic amino ($NH_3^+$) group. We hypothesize that the glutamic acid at position 192 of the measles phosphoprotein is a critical factor that influences the antigenicity of the HLA class II MV-P1 epitope.

We have demonstrated that PBMC expressing the HLA-DRB1*0701 allele induced weak lymphoproliferative responses among antigen-specific T cells to either measles or synthetic measles-derived MV-P1 peptide. In addition, subjects who demonstrated positive recall lymphoproliferative responses to MV were less likely to carry the HLA-DRB1*0301 allele compared to the fraction of individuals who exhibited low measles-specific lymphoproliferative responses. These results should be viewed with some caution as they exist in the absence of significant global tests. However, our results are in agreement with previous studies examining the association between HLA-DRB1 alleles and humoral nonresponsiveness to another viral vaccine, hepatitis B vaccine. Other investigators have noted a significant increase in the frequency of HLA-DR3 and/or -DR7 alleles among poor responders to vaccine (Desombere, et al., *J. Immunol.* 154:520-529, 1995; Craven, et al., *Ann. Intern. Med.* 105:356-360, 1986). In addition, the excess prevalence of HLA-DR7 alleles was observed in patients with chronic persistent infection with hepatitis B virus (Almarri and Batchelor, *Lancet* 344:1194-1195, 1994). However, we did not observe associations between MV-P1 peptide and MV-P2 peptide variant and *0301 allele, which was previously demonstrated to be important in antibody response to measles vaccine virus (Poland, et al., *Vaccine* 20:430-438, 2001).

We have demonstrated that a naturally occurring MV epitope can efficiently elicit or stimulate recall immune responses in previously immunized individuals in the context of multiple HLA-DRB1 molecules. Further, we have demonstrated that a measles epitope variant was capable of modifying cellular immune responses to a single naturally processed measles peptide sequence, and that the glutamic acid at position 192 of the measles structural phosphoprotein is critical for the antigenicity of this naturally processed HLA class II MV peptide. We found that the HLA-DRB1*0701 allele is over-represented in the group of individuals who demonstrated low lymphoproliferative responses to measles and measles-derived MV-P1 peptide and therefore may be regarded as a factor influencing cellular immune responses. Our study of immune responses to naturally processed and presented T cell epitopes should provide the experimental framework for the development of improved vaccines against measles.

TABLE 6

HLA-DRB1 allelic frequency of the 131 study subjects[a].

| HLA-DRB1 locus | Allele | Number of Alleles | Percent, Allele subtype | Percent, HLA-DRB1 locus allele type |
|---|---|---|---|---|
| DR1 | DRB1*0101 | 20 | 7.63 | 8.4 |
|  | DRB1*0102 | 2 | 0.76 |  |
| DR103 | DRB1*0103 | 2 | 0.76 | 0.8 |
| DR2 | DRB1*1501 | 34 | 12.98 | 14.5 |
|  | DRB1*1601 | 3 | 1.15 |  |
|  | DRB1*1602 | 1 | 0.38 |  |
| DR3 | DRB1*0301 | 38 | 14.50 | 14.9 |
|  | DRB1*0302 | 1 | 0.38 |  |
| DR4 | DRB1*0401 | 30 | 11.45 | 17.6 |
|  | DRB1*0402 | 3 | 1.15 |  |
|  | DRB1*0404 | 8 | 3.05 |  |
|  | DRB1*0405 | 2 | 0.76 |  |
|  | DRB1*0407 | 2 | 0.76 |  |
|  | DRB1*0408 | 1 | 0.38 |  |
| DR5 | DRB1*1101 | 11 | 4.20 | 9.9 |
|  | DRB1*1102 | 1 | 0.38 |  |
|  | DRB1*1103 | 2 | 0.76 |  |
|  | DRB1*1104 | 5 | 1.91 |  |
|  | DRB1*1201 | 7 | 2.67 |  |
| DR6 | DRB1*1301 | 14 | 5.34 | 16.0 |
|  | DRB1*1302 | 16 | 6.11 |  |
|  | DRB1*1303 | 2 | 0.76 |  |
|  | DRB1*1304 | 1 | 0.38 |  |
|  | DRB1*1310 | 1 | 0.38 |  |
|  | DRB1*1401 | 6 | 2.29 |  |
|  | DRB1*1405 | 1 | 0.38 |  |
|  | DRB1*1406 | 1 | 0.38 |  |
| DR7 | DRB1*0701 | 30 | 11.45 | 11.4 |
| DR8 | DRB1*0801 | 9 | 3.44 | 4.2 |
|  | DRB1*0803 | 2 | 0.76 |  |
| DR9 | DRB1*0901 | 4 | 1.53 | 1.5 |
| DR10 | DRB1*1001 | 2 | 0.76 | 0.8 |

[a]Each subject represented twice-once for each allele

TABLE 7

HLA-DRB1 allelic associations with measles virus-specific lymphoproliferative responses.

| HLA-DRB1 locus | Allele counts, lymphoproliferation (SI < 2) N | Allele counts, lymphoproliferation (SI < 2) % | Allele counts, lymphoproliferation (SI > 2) N | Allele counts, lymphoproliferation (SI > 2) % | Odds of stimulation index positivity OR[a] | Odds of stimulation index positivity 95% CI[b] | Locus P-Value[c] | Global P-value[c,d] |
|---|---|---|---|---|---|---|---|---|
| DR1 | 4 | 8.33 | 18 | 8.41 | 0.93 | (0.28, 3.07) | 0.90 | 0.16 |
| DR2 | 5 | 10.42 | 33 | 15.42 | 1.61 | (0.62, 4.22) | 0.33 | |
| *0301 | 11 | 22.92 | 27 | 12.62 | 0.50 | (0.22, 1.15) | 0.10 | |
| DR4 | 5 | 10.42 | 41 | 19.16 | 1.93 | (0.66, 5.66) | 0.23 | |
| DR5 | 3 | 6.25 | 23 | 10.75 | 2.04 | (0.56, 7.38) | 0.28 | |
| DR6 | 5 | 10.42 | 37 | 17.29 | 1.85 | (0.66, 5.17) | 0.24 | |
| DR7 | 10 | 20.83 | 20 | 9.35 | 0.40 | (0.18, 0.92) | 0.03 | |
| DR8 | 2 | 4.17 | 9 | 4.21 | 1.21 | (0.23, 6.29) | 0.82 | |
| Other DR alleles[e] | 3 | 6.25 | 6 | 2.80 | 0.36 | (0.07, 1.74) | 0.20 | |

[a]Odds Ratio estimating increase in odds of positivity for each copy of allele of interest, relative to all other alleles pooled together
[b]95% Confidence Interval
[c]Logistic regression analysis, accounting for the design variable age
[d]Likelihood ratio test
[e]Other includes the following DRB1 alleles: DRB1*0103, DRB1*0302, DRB1*0901, DRB1*1001

TABLE 8

HLA-DRB1 allelic associations with measles-derived MV-P1 peptide-specific lymphoproliferative responses.

| HLA-DRB1 locus | Allele counts, lymphoproliferation (SI < 2) N | Allele counts, lymphoproliferation (SI < 2) % | Allele counts, lymphoproliferation (SI > 2) N | Allele counts, lymphoproliferation (SI > 2) % | Odds of stimulation index positivity OR[a] | Odds of stimulation index positivity 95% CI[b] | Locus P-Value[c] | Global P-value[c,d] |
|---|---|---|---|---|---|---|---|---|
| DR1 | 11 | 7.05 | 11 | 10.38 | 1.69 | (0.68, 4.21) | 0.26 | 0.50 |
| DR2 | 19 | 12.18 | 19 | 17.92 | 1.51 | (0.78, 2.92) | 0.22 | |
| *0301 | 25 | 16.03 | 13 | 12.26 | 0.70 | (0.33, 1.46) | 0.34 | |
| DR4 | 27 | 17.31 | 19 | 17.92 | 1.09 | (0.54, 2.24) | 0.80 | |
| DR5 | 14 | 8.97 | 12 | 11.32 | 1.32 | (0.57, 3.06) | 0.52 | |
| DR6 | 28 | 17.95 | 14 | 13.21 | 0.69 | (0.34, 1.39) | 0.29 | |
| DR7 | 23 | 14.74 | 7 | 6.60 | 0.44 | (0.19, 1.05) | 0.06 | |
| DR8 | 5 | 3.21 | 6 | 5.66 | 1.76 | (0.48, 6.22) | 0.40 | |
| Other DR allele[e] | 4 | 2.56 | 5 | 4.72 | 1.96 | (0.47, 8.14) | 0.35 | |

[a]Odds Ratio estimating increase in odds of positivity for each copy of allele of interest, relative to all other alleles pooled together
[b]Confidence Interval
[c]Logistic regression analysis, accounting for the design variable age
[d]Likelihood ratio test
[e]Other includes the following DRB1 alleles: DRB1*0103, DRB1*0302, DRB1*0901, DRB1*1001

TABLE 9

HLA-DRB1 allelic associations with MV-P2 peptide variant specific lymphoproliferative responses.

| HLA-DRB1 locus | Allele Counts, lymphoProliferation (SI < 2) N | Allele Counts, lymphoProliferation (SI < 2) % | Allele Counts, lymphoProliferation (SI > 2) N | Allele Counts, lymphoProliferation (SI > 2) % | Odds of stimulation index positivity OR[a] | Odds of stimulation index positivity 95% CI[b] | Locus P-Value[c] | Global P-value[c,d] |
|---|---|---|---|---|---|---|---|---|
| DR1 | 18 | 8.33 | 4 | 9.09 | 1.10 | (0.34, 3.53) | 0.87 | 0.65 |
| DR2 | 28 | 12.96 | 8 | 18.18 | 1.68 | (0.72, 3.94) | 0.23 | |

TABLE 9-continued

HLA-DRB1 allelic associations with MV-P2 peptide variant specific lymphoproliferative responses.

| HLA-DRB1 locus | Allele Counts, lympho-Proliferation (SI < 2) | | Allele Counts, lympho-Proliferation (SI > 2) | | Odds of stimulation index positivity | | Locus P-Value[c] | Global P-Value[c,d] |
|---|---|---|---|---|---|---|---|---|
| | N | % | N | % | OR[a] | 95% CI[b] | | |
| *0301 | 34 | 15.74 | 4 | 9.09 | 0.55 | (0.18, 1.70) | 0.30 | |
| DR4 | 36 | 16.67 | 10 | 22.73 | 1.48 | (0.60, 3.68) | 0.39 | |
| DR5 | 20 | 9.26 | 6 | 13.64 | 1.54 | (0.55, 4.30) | 0.41 | |
| DR6 | 36 | 16.67 | 6 | 13.64 | 0.77 | (0.29, 2.00) | 0.58 | |
| DR7 | 27 | 12.50 | 3 | 6.82 | 0.57 | (0.17, 1.93) | 0.36 | |
| DR8 | 9 | 4.17 | 2 | 4.55 | 1.04 | (0.20, 5.47) | 0.96 | |
| Other DR alleles[e] | 8 | 3.70 | 1 | 2.27 | 0.37 | (0.04, 3.28) | 0.37 | |

[a]Odds Ratio estimating increase in odds of positivity for each copy of allele of interest, relative to all other alleles pooled together
[b]Confidence Interval
[c]Logistic regression analysis, accounting for the design variable age
[d]Likelihood ratio test
[e]Other includes the following DRB1 alleles: DRB1*0103, DRB1*0302, DRB1*0901, DRB1*1001

TABLE 10

Summary comparison between 2D-LC-MS/MS using on-line SCX and results from 2D-LC-MS/MS using off-line SCX.

| On-line SCX-RP-MS/MS (refs): | Off-line SCX-nRPLC-MS/MS (3 RPLC-MS/MS per SCX Fraction): |
|---|---|
| 10 SCX step elutions | 32 SCX Fractions analyzed |
| 10 nRPLC-MS/MS analyses | 94 nRPLC-MS/MS analyses |
| 12 hrs of LC-MS/MS instrument time | 140 hrs of LC-MS/MS instrument time |
| 1300 MS/MS database queries | 6100 MS/MS database queries |
| 2 Measles virus peptides identified: | 14 measles virus peptides identified: |
| From measles phosphoprotein: ASDVETAEGGEIHELLRLQ (SEQ ID NO:2) | From measles phosphoprotein: ASDVETAEGGEIHELLRLQ (SEQ ID NO:2) ASDVETAEGGEIHELLR (SEQ ID NO:3) ASDVETAEGGEIHELLRLQSR (SEQ ID NO:4) GFRASDVETAEGGEIHELLRLQ (SEQ ID NO:5) TLNVPPPPDPGR (SEQ ID NO:6) TLNVPPPPDPGRASTSGTPIKK (SEQ ID NO:7) KMSSAVGFVPDTGPASR (SEQ ID NO:8) M(ox)SSAVGFVPDTGPASR (not confirmed) (SEQ ID NO:16) LGKDPNDLTADVEINP (later disqualified by comparison to the authentic sequence) (SEQ ID NO:17) |
| From measles nucleoprotein: SAGKVSSTLASELG (SEQ ID NO:1) | From measles nucleoprotein: SAGKVSSTLASELG (SEQ ID NO:1) SAGKVSSTLASELGITAEDARLVS (SEQ ID NO:9) AVGPRQAQVSF (SEQ NO NO:10) LLEVVQSDQSQSGLTFASR (SEQ ID NQ:11) HLPTGTPLDIDTATESSQDPQDSR (SEQ ID NO:12) |
| | From measles hemagglutinin: SLSTNLDVTNSIEHQVKDVLTPLFK (SEQ ID NO:13) |

Example 4

Identification of Class II HLA-DRB1*03-Restricted Measles Virus Peptides by 2D-Liquid Chromatography Tandem Mass Spectrometry In Examples 1-3, we have described the identification of two peptides, one from measles virus phosphoprotein and the other from measles virus nucleocapsid protein that were presented by the human leukocyte antigen (HLA) class II molecule HLA-DRB1*03. These two peptides also generated recall immune response in PBMC from previously immunized donors, as demonstrated by their ability to induce secretion of the cytokines interferon-γ (IFN-γ) and interleukin-4 (IL-4). In this example, through a more rigorous application of 2DLC-MS/MS methods, we have identified 11 additional peptides originating from measles virus in addition to the two peptides previously reported. The peptides originate from three of the six functional measles virus proteins: phosphoprotein, nucleocapsid, and hemagglutinin. One peptide from hemagglutinin was identified, while the additional peptides identified from phosphoprotein and nucleocapsid proteins include both N- and C-terminal extensions of the previously reported peptides, as well as peptides with core sequences not previously reported from HLA-DRB1*03 restriction. These peptides have also been surveyed for their ability to induce a recall immune response.

Introduction

Previous work from our laboratories has identified two naturally processed peptides originating from measles virus proteins: one having SEQ ID NO:2 from phosphoprotein, and the other having SEQ ID NO:1 from nucleocapsid protein. Synthesized peptides with these sequences were able to generate recall immune response in PBMC from previously immunized donors, as demonstrated by their ability to induce secretion of the cytokines interferon-γ (IFN-γ) and interleukin-4 (IL-4) (Ovsyannikova, et al., *Virology* 312:495-506, 2003; Ovsyannikova, et al., *J. Virol.* 78:42-51, 2004). Given the open binding pocket of the HLA class II complex, additional measles peptides with common core sequences were also expected to be present. In an attempt to more comprehensively identify peptides isolated from HLA class II molecules, analytical methods were enhanced to increase the number of peptides for which tandem mass spectra (MS/MS) could be acquired.

Three areas were chosen in which to improve the analytical method: (1) the strong cation exchange (SCX) chromatography was conducted off-line, independently of the nano-scale reversed phase liquid chromatography (nLC). This allowed the addition of organic solvent to the SCX mobile phases to reduce secondary hydrophobic interactions between the peptides and the ion exchange stationary phase. Furthermore, a continuous gradient was employed rather than the step elutions used in our previous manuscript. Fraction collection was used to allow multiple random access to fractions of interest, an attribute not possible when using a hyphenated (on-line) coupling of SCX with nano-scale reversed phase liquid chromatography (nLC). With this approach, we obtained a more efficient SCX separation resulting in more SCX fractions. We also observed that any given peptide was distributed across fewer fractions than our earlier hyphenated approach (Ovsyannikova, et al., supra, 2003). (2) SCX fractions were analyzed multiple times by nLC-MS/MS using a different subset of the precursor m/z space with each analysis. This technique of gas phase fractionation (GPF) (Spahr, et al., *Proteomics* 1:93-107, 2001; Davis, et al., *Proteomics* 1:108-117, 2001); provides MS/MS access to lower intensity peptides that would not be chosen from survey scans of a complex mixture over a broad m/z range. (3) The resolution of our reversed phase chromatography was increased. Our previous work used a 6 cm long nLC column with a gradient rate-of-change of 3% B/min. Work described here used a 15 cm long nLC column with a gradient rate-of-change of 0.85% B/min. These changes resulted in peptides eluting over a 60 minute window versus a 30 minute window in earlier work, allowing more extensive interrogation by tandem mass spectrometry.

Materials and Methods

Our methods for donor cell preparation and measles virus infection have been outlined below.

Donor Cell Preparation

We generated an EBV-transformed B cell line from PBMC of an HLA-DRB1*0301 homozygous subject using $1 \times 10^7$ PBMC and the B95-8 strain of EV (American Type Culture Collection, Manassas, Va.) in RPMI medium containing 1 ug/ml cyclosporin A.

Cell Culture and Virus Infection

Edmonston B vaccine strain of measles virus was grown in Vero cells, in Dlubecco's modified Eagle's medium, supplemented with 5% fetal calf serum (FCS). Subsequently, EBV-B cells were infected with live measles virus at a multiplicity of infection (moi) of 1 PFU/cell for 1 hour and maintained for 24-36 hours at 37° C. in RPMI-1640 containing 2% FCS (Life Technologies, Gaithersburg, Md.). The indicated moi was based on viral tissue culture infectious dose (TCID50) titers of the stock preparation determined by a standard assay using Vero cells (virus stocks of $2 \times 10^7$ PFU/ml). Equally sized batches of measles-infected and uninfected cells were washed in PBS, pelleted and stored at −80° C.

Immunoaffinity Purification of HLA-DR3 Molecules and Bound Peptides

Details of methodological strategy for peptide purification have been described elsewhere (Ovsyannikova, et al., supra, 2003). HLA-DRB1*03 bound peptides were isolated from immunoaffinity purified class II molecules using the HLA-DR-specific monoclonal antibody (L227, IgG1) covalently linked to CNBr-activated Sepharose 4B beads (Sigma) (Ovsyannikova and Johnson, *J. Virol.*, 2004). Ten-gram cell pellets consisting of either infected or uninfected cells were lysed in 1% CHAPS, 150 mM NaCl, 20 mM Tris-HCl, pH 8.0 and 1 mM Pefablock SC. The HLA-DR-peptide complexes were eluted from the affinity column (pH 11.5) with 0.1% deoxycholic acid and 50 mM glycine. The eluates were neutralized with 2M glycine and concentrated in a Centricon-10 (Amicon, Beverly, Miami) before a second round of precipitation by 14% acetic acid to dissociate any bound peptides from HLA-DRB1*03 molecules. The peptides were concentrated in a spin vacuum to 500 mL aliquots and stored at −80° C. for later analysis by MS.

Peptide Desalting Prior to SCX Chromatography

Prior to SCX chromatography, class II peptides were desalted on a reversed phase cartridge (1 mm i.d. by 10 mm long PeptideTrap, Michrom BioResources, Inc. Auburn, Calif.). The cartridge was manually cleaned, equilibrated, loaded with peptides, washed to remove salts, and peptides eluted, using a syringe port adaptor and 50-100 μL syringe volumes. The eluted peptides were vacuum-concentrated to 5-10 μL and reconstituted with SCX mobile phase A prior to ion exchange fractionation.

SCX Chromatography with Fraction Collection

SCX separations were performed on a MAGIC 2000 HPLC (Michrom BioResources, Inc.) using a 0.5 mm i.d. by 50 mm long Polysulfoethyl A column (5 µm, 300 Å, Michrom BioResources, Inc.). SCX mobile phase A was 5 mM $KH_2PO_4$, pH=3.1/10% acetonitrile. SCX mobile phase B was 500 mM KCl in SCX mobile phase A. The mobile phase gradient started at 0% B with linear gradients to 20% B at 20 minutes, 80% B at 30 minutes, followed by a 5 minute hold at 80% B, 5 minutes to return to 0% B and a 15 minute re-equilibration period (50 minute total method). The column flow rate was 40 pµL/min. The UV detector was monitored at 214 nm and 280 nm. A one meter length of 100 µm i.d. fused silica (8 µL volume, 0.2 minute delay at 40 µL/min), connected to the exit of the UV flow cell, was used to collect fractions. Fractions were collected at 1 minute intervals on a Gilson FC 203B fraction collector. Fractions were stored at −80° C. until analysis by nLC-MS/MS.

nLC-MS/MS of SCX Fractions

Automated nLC-MS/MS measurements were performed on a QToF API-US quadrupole-time of flight mass spectrometer controlled by MassLynx 4.0 (Waters, Framingham, Mass.) interfaced to a Waters CapLC and autosampler. nLC separations were done on a 75 µm i.d. by 15 cm Integrafrit column (New Objective, Wobum, Mass.) slurry-packed with 5 µm Targa C18, (Higgins Analytical, Mountain View, Calif., USA). Prior to nLC-MS/MS analyses, SCX fractions were vacuum-concentrated on a SpeedVac from 40 µL to 5-10 µL to reduce their acetonitrile content. Fractions were then reconstituted to 40 µL with 5 mM $KH_2PO_4$ containing 5% acetonitrile.

The autosampler loaded 10 µL aliquots of SCX fractions onto a 0.3 mm i.d. by 5 mm long pre-column (PepMap, Dionex, Sunnyvale, Calif.) that was plumbed into the injection loop of a Cheminert 10-port switching valve (Valco Instruments Company, Inc., Houston, Tex.). Mobile phase A was water/acetonitrile/n-propanol/formic acid (98/1/1/0.2 by volume) and mobile phase B was acetonitrile/n-propanol/water/formic acid (80/10/10/0.2 by volume). A gradient from 3-50% B over 60 minutes was used at an approximate column flow of 0.2 µL/min. Pump C on the CapLC was used to transfer samples from the autosampler to the pre-column, using a 10 µL/min flow of water/acetonitrile/n-propanol/formic acid (98/1/1/0.2 by volume) that additionally contained 0.5 mM ammonium acetate. A 10 min transfer period (100 µL total volume) was used to transfer sample and wash potassium salts from the peptides before switching the precolumn in-line with the nLC column and starting the reversed phase gradient.

Automated MS/MS experiments used a survey scan to select the three most intense doubly, triply, or quadruply charged ions as MS/MS precursors, using charge and m/z-dependent selection of collision energies. To increase the number of peptides that could be measured by MS/MS, three nLC-MS/MS analyses, using three survey scan ranges, were performed for each SCX fraction: m/z 550-750, m/z 740-900, and m/z 890-1200.

Database Searching of MS/MS Data

MS/MS spectra were searched against a subset of the NCBI nr database compiled from all human, bovine, and measles virus entries using MASCOT search software (ver. 1.9) running on a 10-node PC cluster. The PeptideAuto program from MassLynx 4.0 was used to generate ASCII peak list (PKL) files from each LC-MS/MS analysis. A PERL script was used to combine PKL files from 94 nLC-MS/MS analyses. A second PERL script sorted the combined PKL file into two PKL files, one containing data from doubly and triply charged precursors, and the second PKL file containing data from quadruply charged precursors. This was done to accommodate the parameter for precursor charge state in the MASCOT software. A precursor mass window of 1.2 mass units and a fragment ion mass window of 0.2 mass units was used for the searches. The broad precursor ion tolerance was chosen to allow for potential mis-assignment of precursor monoisotopic mass from triply and quadruply charged ions, and to consider aparagine/aspartate, or glutamine/glutamate ambiguities from database or sample handling sources.

Peptide Synthesis

Sequences from tentatively identified measles virus peptides were subsequently synthesized by the peptide synthesis laboratory of the Mayo Proteomics Research Center (Rochester, Minn.). Each peptide was purified by reversed phase liquid chromatography and their correct molecular weights were confirmed by mass spectrometry.

Results and Discussion

Figure 8:
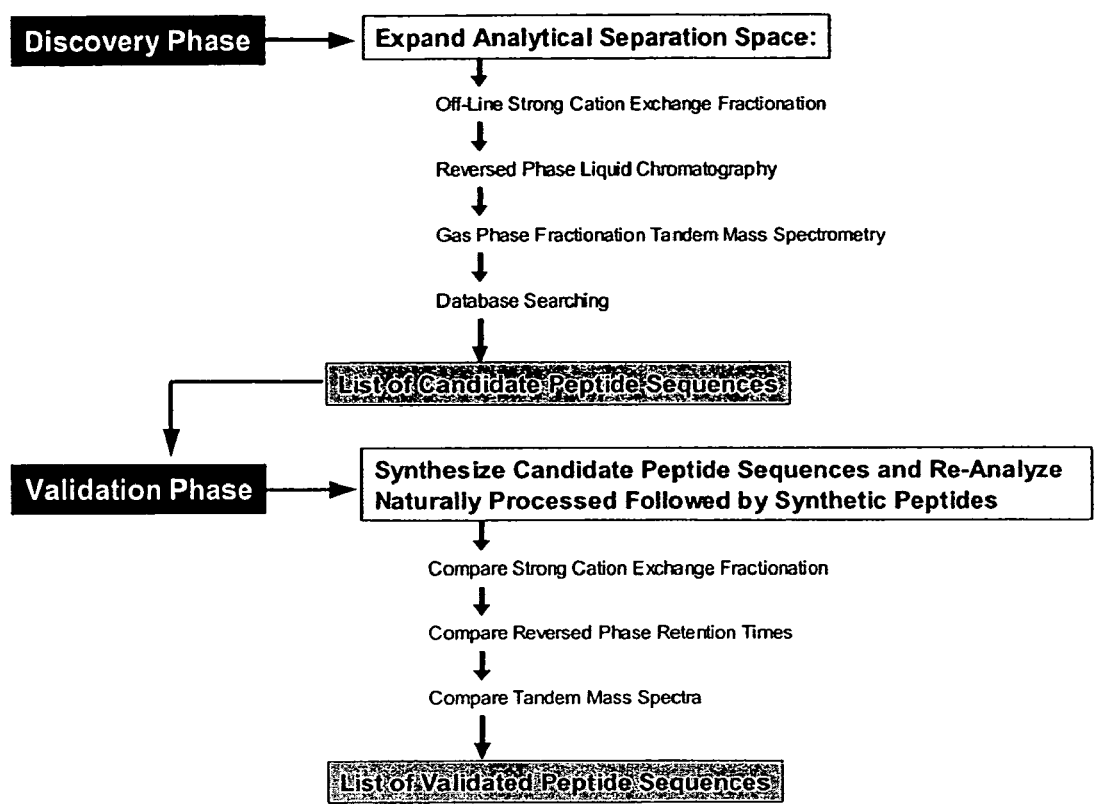
FIG. 8 is an overview of the analysis steps used for separating and identifying HLA class II peptides.

UV (214 nm) chromatograms from the cation exchange separation of the pool of Class II peptides isolated from measles-infected B cells, as well as the preceding blank, are shown in FIG. 8. Fractions 1-32 from the strong cation exchange separation were analyzed over three precursor ion m/z ranges for a total of 94 nLC-MS/MS analyses. We found the off-line cation exchange separation to be advantageous from a number of perspectives: (1) peptides eluted from the SCX column over a broad time frame, being observed in each of the first 32 fractions; (2) time-based, one minute fractions resulted in peptides residing predominantly in a single fraction; (3) individual SCX fractions could be readily accessed for multiple analyses; and (4) the CHAPS detergent used for cell lysis eluted predominantly in the SCX injection void volume (the first two fractions), a region of low peptide population density. A 10% acetonitrile concentration was chosen because it produced UV chromatograms of BSA tryptic digests with the same SCX peak widths as 25% acetonitrile. The lower amount of acetonitrile was more amenable to reversed phase chromatography by either dilution or vacuum concentration.

FIG. 8-B displays base peak chromatograms for the survey scan data from the precursor m/z range 740-900 for SCX fractions 13-16 demonstrating the typical reversed phase separations obtained and the small amount of peptide overlap between SCX fractions.

As a result of the described changes to the method, we were able to increase the number of peptides interrogated by MS/MS from 1300 MS/MS queries to 6100 MS/MS queries, leading to tentative identification of 14 peptides from measles virus proteins, including the two peptides previously reported. Details of the comparison to earlier work are summarized in Table 10.

The use of database searching of MS/MS spectra to determine the sequences of naturally processed HLA class I or class II peptides differs in a number of ways from database searching methods aimed at identifying proteins. First, since trypsin is not used, the C-terminal amino acid is not constrained to being a lysine, an arginine, or the C-terminus of the protein. This greatly increases the number of candidate sequences that pass through the precursor mass filter to be subsequently considered on the basis of fragment ions. Secondly, due to the selectivity of peptides binding to the HLA molecule, sequence coverage of the proteins from which any peptide originates will be lower than typically observed in proteomic studies. Researchers in proteomics debate the validity of "one-hit wonders", where proteins are identified solely on the search results from a single MS/MS spectrum. However, this situation is not unusual in studies of HLA-bound peptides, and is often the norm when sequencing Class I peptides as is seen in a compilation of published class I and class II peptides (Rammensee, et al., *Immunogenetics* 50:213-219, 1999).

To prevent false peptide identifications in large data sets where search results cannot be individually validated, criteria for accepting search results based on a score or measure of goodness-of-fit between data and database search results are often adopted (Keller, et al., *Anal. Chem.* 74:5383-5392, 2002; Peng, et al., *J. Proteome Res.* 2:43-50, 2003; Cargile, et al., *J. Proteome Res.* 3:1082-1085, 2004; Qian, et al, *J. Proteome Res.* 4:53-62, 2005). The lack of C-terminal amino acid constraint (e.g. Lys or Arg) for HLA-bound peptides would suggest the adoption of very stringent criteria for accepting search results. However, adoption of more stringent criteria in order to reduce false positives will also decrease the sensitivity of the identification process, i.e. will lead to an increased incidence of false negatives: the rejection of correct search results because of low score.

Figure 9:
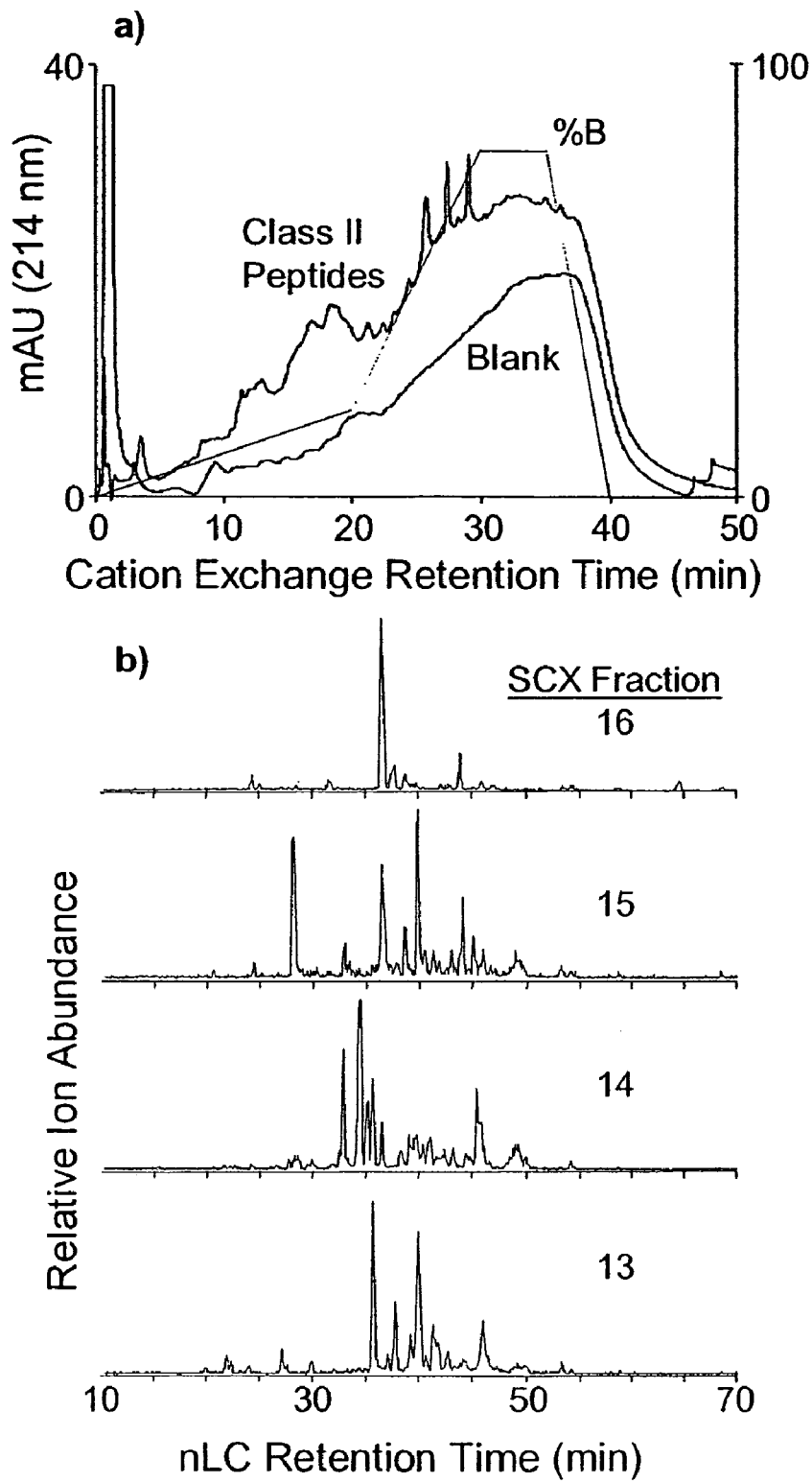
FIG. 9A demonstrates strong cation exchange UV (214 nm) chromatograms showing a blank analysis and the separation of class II peptides harvested from B-cells that had been infected with measles virus. Fractions were collected at 1 minute intervals.
FIG. 9B demonstrates base peak chromatograms for the precursor m/z range of 740-900, for SCX fractions 13-16. Additional peptides were seen in analyses that covered the ranges from m/z 550-750 and m/z 890-1200.

Alternatively, we used a more traditional approach, performing peptide identification in two phases as described in FIG. 9. In the discovery phase, we considered potential measles virus matches, including those with lower scores, followed by manual inspection of MS/MS spectral quality and matching of charge state from the survey scan with that required by the molecular weight of the matched peptide sequence. Each tentatively identified measles peptide was subsequently synthesized both to validate our identification and to assess any immunogenic or immunoproliferative properties.

In the second phase, peptide identifications were validated by repeating the SCX fractionation, first with the naturally processed peptides, and secondly with a pool of the synthetic peptides. SCX fractions from the naturally processed peptide pool were re-analyzed by nLC-MS/MS using a single precursor m/z window, minimized to cover the m/z range of tentatively identified measles virus precursor ions. SCX fractions of the synthetic peptides were also analyzed by nLC-MS/MS. The data from each proposed naturally processed measles virus peptide was compared to authentic reference peptide in terms of MS/MS spectra, cation exchange fraction, and reversed phase retention time.

Figure 10:
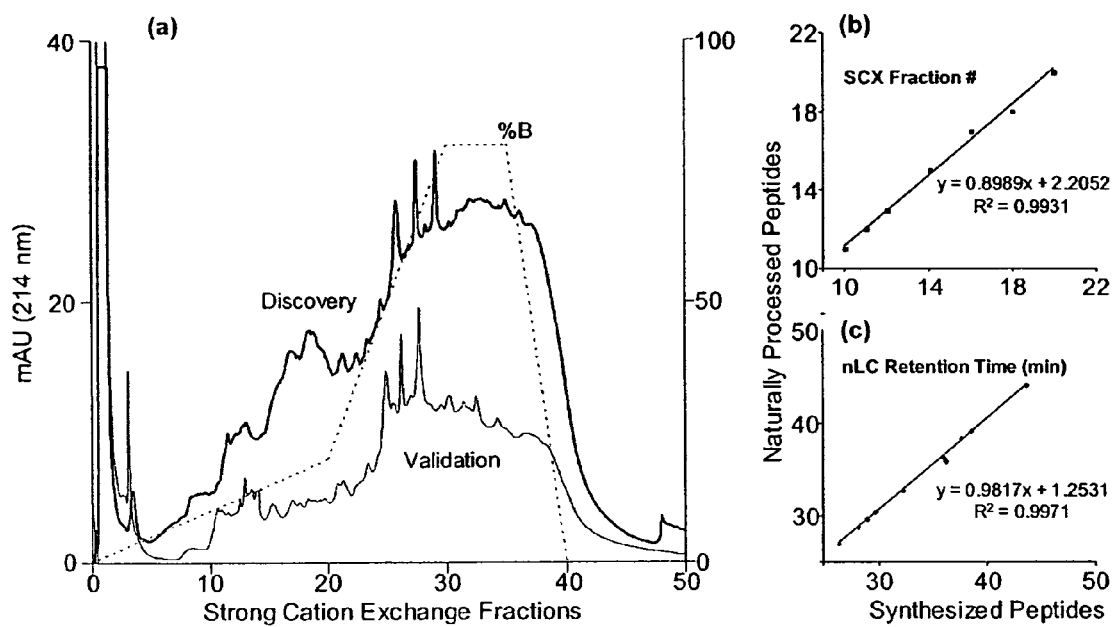
FIG. 10 is validation of tentatively identified naturally processed peptides against synthesized analogs: 10A) SCX UV (214 nM) chromatograms of naturally processed peptides separated during the discovery phase and again during validations stage; 10B) from validation stage, comparison of SCX fractions of naturally processed peptides against the synthesized peptides; 10C) from the validation phase, comparison of reversed phase nLC retention times of naturally processed peptides against synthesized peptides.

FIG. 10 shows these results. FIG. 10a compares the UV chromatogram of the cation exchange separation of naturally processed peptides performed for the discovery phase, to the refractionation of the naturally processed peptides performed during the validation phase. These two chromatograms were acquired with a two month interval, and while the chromatograms do not completely superimpose, the high degree of similarity between the two chromatograms is clearly evident. FIG. 10b characterizes the correlation that was seen between the naturally processed peptides fractionated by cation exchange during the validation analyses versus synthetic peptides fractionated the same day. Synthetic peptides were found to elute within one, one-minute fraction of each other, adding supporting evidence to our identifications. FIG. 10c depicts the comparison of nLC retention times of the naturally processed peptides versus the authentic synthesized peptides. The strong correlation between nLC retention times from each set of peptides also supports our identifications.

From the 14 sequences tentatively identified from measles virus during our initial discovery analyses, two sequences had been previously reported and were not re-validated, and 10 sequences were validated, based on data summarized in FIG. 10. During the validation phase, three naturally processed peptides were detected in the precursor scans that were not selected for MS/MS experiments. In these cases the tandem mass spectrum from the discovery phase was compared to that from the synthesized peptide. For these peptides, SCX fractions and nLC retention times were compared using naturally processed precursor ion data from the validation analyses versus the synthesized peptides. The peptide having SEQ ID NO:16 from measles phosphoprotein, was tentatively identified with an oxidized methionine that was not reproduced as an oxidized methionine in its synthetic version and so cannot be directly compared. However we were able to confirm the related peptide having SEQ ID NO:8 from measles phosphoprotein. One synthetic peptide having SEQ ID NO:17, a sequence from measles phosphoprotein, was found to be inconsistent with the MS/MS spectrum from the naturally processed peptides. The MOWSE score for this peptide was low: 19 versus thresholds of 27 for homology, and 57 for identity.

Figure 11:
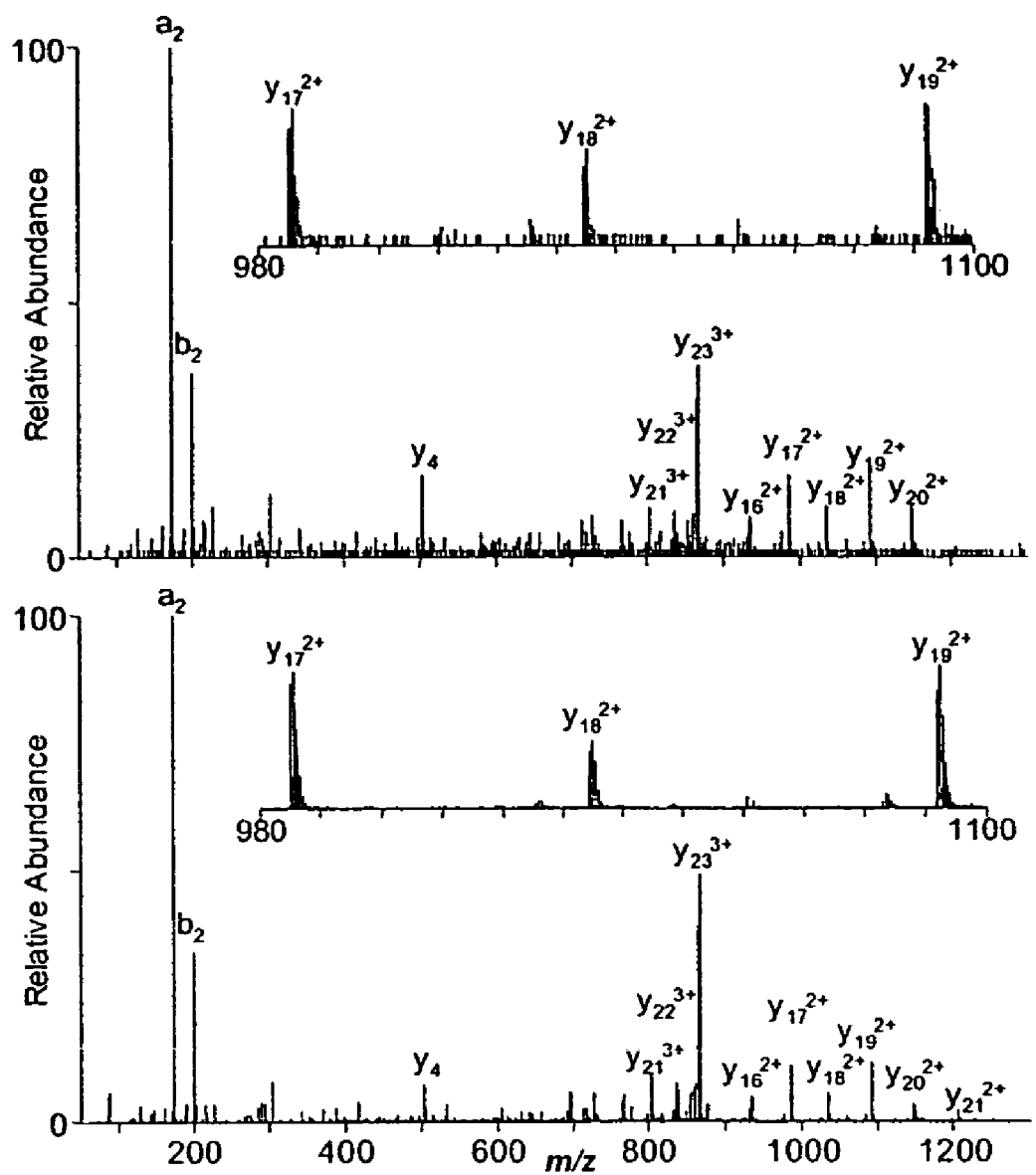
FIG. 11 is validation of the measles hemagglutinin peptide having SEQ ID NO:13. 11A) tandem mass spectrum from the naturally processed peptide from SCX fraction 18, and 11B) tandem mass spectrum obtained from direct infusion of the synthesized peptide.

FIG. 11 shows the MS/MS comparison of m/z 700.36, z=4, a naturally processed peptide (upper trace) tentatively identified as having SEQ ID NO:13 from the measles hemagglutinin protein. The lower trace of FIG. 11 shows the spectrum of a synthetic peptide having SEQ ID NO:13 from an infusion experiment. This synthetic peptide was not part of the mixture of synthetic peptides analyzed by 2D-LC, so SCX elution and reversed phase retention time cannot be compared. However, the two spectra are in close agreement, as described by the labeled fragment ions. The resolving power of the time-of-flight analyzer allows confirmation that the charge states of the precursor ion and fragment ions also match between the naturally processed peptide and the synthesized peptide. The identification of a peptide from hemagglutinin is of particular interest since the initial adhesion of the measles virus to the cell is through the hemagglutinin protein.

Figure 12:
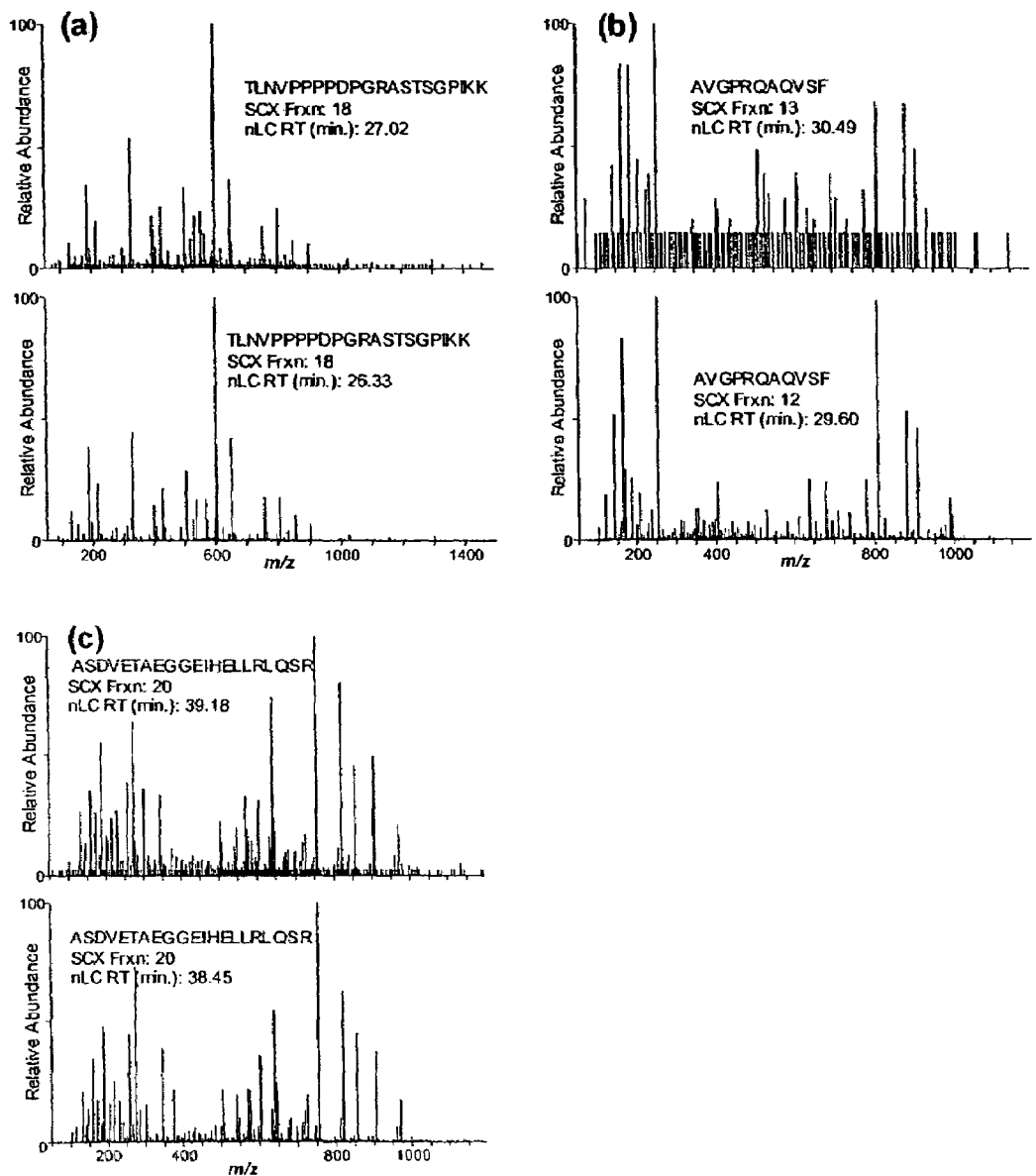
FIG. 12 is a comparison of four tandem mass spectra between naturally processed peptides (upper trace) and synthesized peptides (lower trace): 12A) SEQ ID NO:7 from measles phosphoprotein, 12B) SEQ ID NO:10 from measles nucleocapsid protein, and 12C) SEQ ID NO:4 from measles phosphoprotein.

FIG. 12 compares MS/MS spectra from four naturally processed peptides (upper traces) to their synthesized counterparts (lower traces) and summarizes comparison of their supporting chromatographic data to demonstrate the validation process. FIG. 12a compares a spectrum from the naturally processed peptide (upper trace) to the synthesized peptide having SEQ ID NO:7 from phosphoprotein (lower trace). FIG. 12b illustrates the validation of a peptide having SEQ ID NO:10 from the nucleocapsid protein. In this example, where the low signal-to-noise ratio of the naturally processed spectrum limits the comparison with the synthetic peptide to major fragment ions, the cation exchange fractions and nLC retention times are advantageous in supporting this identification of the naturally processed peptide. FIG. 12c compares spectra from a naturally processed peptide vs the synthetic peptide having SEQ ID NO:4 from measles phosphoprotein, an extension of the peptide having SEQ ID NO:2 identified previously (Ovsyannikova, et al., supra, 2003). FIG. 12d illustrates an example where the validation process is capable of detecting false positive results. In this case, the precursor ion was 1 mass unit less than predicted by the sequence and the MOWSE score was low, but the SCX fraction, and reversed phase retention time of the synthetic peptide relative to the naturally processed peptide were very similar. The two spectra clearly demonstrate that the naturally processed peptide is not SEQ ID NO:17 from measles virus phosphoprotein.

CONCLUSIONS

This work has reported the application of rigorous 2D-LC-MS/MS analyses to the complex pool of class II peptides isolated from B-cells infected with measles virus, to allow more exhaustive MS/MS sampling of the presented peptides, thereby identifying 11 new peptides from measles virus presented by B-cells infected with measles virus. The total of 13 peptides observed represent three HLA core sequences from the measles phosphoprotein, four HLA core sequences from the measles nucleocapsid protein, and one core sequence from the measles hemagglutinin protein. It is noteworthy that even with the increased chromatographic separation, MS/MS data could not be collected for all of the molecular species observed in the survey scans. Continued advances in the analytical methodology will allow additional discovery and insight into the molecular processes that comprise the immune response to measles virus and other pathogens. In turn, identification of such HLA-presented immunogenic peptides will facilitate the directed design of new peptide-based vaccines against human pathogens.

I claim:

1. A preparation of an isolated HLA class II binding peptide consisting of SEQ ID NO:13.

2. The preparation of claim 1, further comprising at least one additional peptide selected from the group consisting of SEQ ID NOs:1-12.

3. The preparation of claim 1, further comprising at least two additional peptides selected from the group consisting of SEQ ID NOs:1-12.

4. The preparation of claim 1, further comprising at least four additional peptides selected from the group consisting of SEQ ID NOs:1-12.

5. A method of diagnosing measles virus infection or immunity to measles virus in a human patient comprising analyzing a biological sample taken from the patient for the presence of the peptide SEQ ID NO:13, or an antibody to the peptide of SEQ ID NO:13, wherein the detection of the peptide, or the antibody to the peptide, proves the presence of measles virus infection or immunity to measles virus in the patient.

6. The method of claim 5, further comprising analyzing for the presence of the peptide of SEQ ID NO:1 or an antibody to the peptide of SEQ ID NO:1.

7. The method of claim 5, further comprising analyzing for the presence of the peptide of SEQ ID NO:2 or an antibody to the peptide of SEQ ID NO:2.

8. The method of claim 5, further comprising analyzing for the presence of the peptide selected from SEQ ID Nos: 3 or 6, or an antibody to the peptide of SEQ ID Nos:3 or 6.

* * * * *

UNITED STATES PATENT AND TRADEMARK OFFICE
CERTIFICATE OF CORRECTION

PATENT NO. : 7,579,004 B2  
APPLICATION NO. : 11/266957  
DATED : November 4, 2005  
INVENTOR(S) : Gregory A. Poland Page 1 of 1

It is certified that error appears in the above-identified patent and that said Letters Patent is hereby corrected as shown below:

Title page, item (*) Notice: should read as follows: Subject to any disclaimer, the term of this patent is extended or adjusted under 35 U.S.C. 154(b) by 570 days.
Column 20, line 57, "fray" should be -- tray --
Column 21, line 26, "(100 U/mL) supplemented" should be -- (100 U/mL) and supplemented --
Column 49, line 26, "Wobum" should be -- Woburn --

Signed and Sealed this

Fifteenth Day of June, 2010

David J. Kappos
*Director of the United States Patent and Trademark Office*

SEQUENCE LISTING

```
<160> NUMBER OF SEQ ID NOS: 17

<210> SEQ ID NO 1
<211> LENGTH: 14
<212> TYPE: PRT
<213> ORGANISM: Measles virus

<400> SEQUENCE: 1

Ser Ala Gly Lys Val Ser Ser Thr Leu Ala Ser Glu Leu Gly
1               5                   10

<210> SEQ ID NO 2
<211> LENGTH: 19
<212> TYPE: PRT
<213> ORGANISM: Measles virus

<400> SEQUENCE: 2

Ala Ser Asp Val Glu Thr Ala Glu Gly Gly Glu Ile His Glu Leu Leu
1               5                   10                  15

Arg Leu Gln

<210> SEQ ID NO 3
<211> LENGTH: 17
<212> TYPE: PRT
<213> ORGANISM: Measles virus

<400> SEQUENCE: 3

Ala Ser Asp Val Glu Thr Ala Glu Gly Gly Glu Ile His Glu Leu Leu
1               5                   10                  15

Arg

<210> SEQ ID NO 4
<211> LENGTH: 21
<212> TYPE: PRT
<213> ORGANISM: Measles virus

<400> SEQUENCE: 4

Ala Ser Asp Val Glu Thr Ala Glu Gly Gly Glu Ile His Glu Leu Leu
1               5                   10                  15

Arg Leu Gln Ser Arg
            20

<210> SEQ ID NO 5
<211> LENGTH: 22
<212> TYPE: PRT
<213> ORGANISM: Measles virus

<400> SEQUENCE: 5

Gly Phe Arg Ala Ser Asp Val Glu Thr Ala Glu Gly Gly Glu Ile His
1               5                   10                  15

Glu Leu Leu Arg Leu Gln
            20
```

```
<210> SEQ ID NO 6
<211> LENGTH: 12
<212> TYPE: PRT
<213> ORGANISM: Measles virus

<400> SEQUENCE: 6

Thr Leu Asn Val Pro Pro Pro Asp Pro Gly Arg
1               5                   10

<210> SEQ ID NO 7
<211> LENGTH: 22
<212> TYPE: PRT
<213> ORGANISM: Measles virus

<400> SEQUENCE: 7

Thr Leu Asn Val Pro Pro Pro Asp Pro Gly Arg Ala Ser Thr Ser
1               5                   10                  15

Gly Thr Pro Ile Lys Lys
            20

<210> SEQ ID NO 8
<211> LENGTH: 17
<212> TYPE: PRT
<213> ORGANISM: Measles virus

<400> SEQUENCE: 8

Lys Met Ser Ser Ala Val Gly Phe Val Pro Asp Thr Gly Pro Ala Ser
1               5                   10                  15

Arg

<210> SEQ ID NO 9
<211> LENGTH: 24
<212> TYPE: PRT
<213> ORGANISM: Measles virus

<400> SEQUENCE: 9

Ser Ala Gly Lys Val Ser Ser Thr Leu Ala Ser Glu Leu Gly Ile Thr
1               5                   10                  15

Ala Glu Asp Ala Arg Leu Val Ser
            20

<210> SEQ ID NO 10
<211> LENGTH: 11
<212> TYPE: PRT
<213> ORGANISM: Measles virus

<400> SEQUENCE: 10

Ala Val Gly Pro Arg Gln Ala Gln Val Ser Phe
1               5                   10

<210> SEQ ID NO 11
<211> LENGTH: 19
<212> TYPE: PRT
<213> ORGANISM: Measles virus

<400> SEQUENCE: 11

Leu Leu Glu Val Val Gln Ser Asp Gln Ser Gln Ser Gly Leu Thr Phe
1               5                   10                  15

Ala Ser Arg

<210> SEQ ID NO 12
<211> LENGTH: 24
<212> TYPE: PRT
<213> ORGANISM: Measles virus
```

```
<400> SEQUENCE: 12

His Leu Pro Thr Gly Thr Pro Leu Asp Ile Asp Thr Ala Thr Glu Ser
1               5                   10                  15

Ser Gln Asp Pro Gln Asp Ser Arg
            20

<210> SEQ ID NO 13
<211> LENGTH: 25
<212> TYPE: PRT
<213> ORGANISM: Measles virus

<400> SEQUENCE: 13

Ser Leu Ser Thr Asn Leu Asp Val Thr Asn Ser Ile Glu His Gln Val
1               5                   10                  15

Lys Asp Val Leu Thr Pro Leu Phe Lys
            20                  25

<210> SEQ ID NO 14
<211> LENGTH: 19
<212> TYPE: PRT
<213> ORGANISM: Measles virus

<400> SEQUENCE: 14

Ala Ser Asp Val Glu Thr Ala Glu Gly Gly Glu Ile His Lys Leu Leu
1               5                   10                  15

Arg Leu Gln

<210> SEQ ID NO 15
<211> LENGTH: 14
<212> TYPE: PRT
<213> ORGANISM: Artificial
<220> FEATURE:
<223> OTHER INFORMATION: Synthetic peptide

<400> SEQUENCE: 15

Pro Leu Arg His Gln Ala Thr Thr Ala Ser Ser Thr Lys Pro
1               5                   10

<210> SEQ ID NO 16
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Oxidized methionine

<400> SEQUENCE: 16

Met Ser Ser Ala Val Gly Phe Val Pro Asp Thr Gly Pro Ala Ser Arg
1               5                   10                  15

<210> SEQ ID NO 17
<211> LENGTH: 16
<212> TYPE: PRT
<213> ORGANISM: Artificial
<220> FEATURE:
<223> OTHER INFORMATION: Synthetic peptide

<400> SEQUENCE: 17

Leu Gly Lys Asp Pro Asn Asp Leu Thr Ala Asp Val Glu Ile Asn Pro
1               5                   10                  15
```